US007196119B2

(12) United States Patent
Scanlan et al.

(10) Patent No.: US 7,196,119 B2
(45) Date of Patent: Mar. 27, 2007

(54) DEVELOPMENT OF NEW SELECTIVE ESTROGEN RECEPTOR MODULATORS

(75) Inventors: Thomas S. Scanlan, San Francisco, CA (US); Martin J. Kelly, Portland, OR (US); Jian Qiu, Portland, OR (US); Sandra Tobias, San Francisco, CA (US); Oline K. Ronnekleiv, Portland, OR (US)

(73) Assignees: The Regents of the University of California, Oakland, CA (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 10/970,242

(22) Filed: Oct. 20, 2004

(65) Prior Publication Data

US 2005/0113453 A1 May 26, 2005

Related U.S. Application Data

(60) Provisional application No. 60/513,235, filed on Oct. 21, 2003.

(51) Int. Cl.
*A61K 31/167* (2006.01)
*C07C 233/01* (2006.01)

(52) U.S. Cl. ............... 514/627; 564/207; 564/204; 564/192; 564/171; 564/95; 564/84; 560/129; 514/570; 514/605

(58) Field of Classification Search ............. 514/627, 514/605, 570; 564/207, 204, 192, 171, 95, 564/84; 560/129; 568/840
See application file for complete search history.

(56) References Cited

U.S. PATENT DOCUMENTS

| 4,038,415 A | 7/1977 | Rajadhyaksha et al. ...... 424/317 |
| 6,444,420 B2 | 9/2002 | Mobley et al. ............... 435/4 |
| 2003/0171412 A1 | 9/2003 | Malamas et al. ............ 514/367 |
| 2003/0181519 A1 | 9/2003 | Mewshaw et al. ........... 514/520 |

OTHER PUBLICATIONS

Mittal, S. et al.: Structure-Activity relationship of estrogens, receptor affinity and estrogen antagonist activity of certain (E) and (Z)-1,2,3-triaryl-2-propen-1-ones. J. Med. Chem. vol. 28, pp. 492-497, 1985.*
Iyer, R. N. et al.: Anti-implantation effect of 2,3-diphenylacrylophenones. Indian J. of Exp. Biol. vol. 5, pp. 169-170, 1967.*
Durani, N. et al.: Structure-Activity relationship of antiestrogens: A study using triarylbutenone, benzofuran, and triarylfuran analogues as models for triarylethylenes and triarylpropenones. J. Med. Chem. vol. 32, pp. 1700-1707, 1989.*

Akema, T., et al., "On the relationship between noradrenergic stimulatory and GABAergic inhibitory systems in the control of luteinizing hormone secretion in female rats," *Neuroendocrinology*, 1990, 52, 566-572.
Akhter, S.A., et al., "Targeting the receptor-$G_q$ interface to inhibit in vivo pressure overload myocardial hypertrophy," *Science*, 1998, 280, 574-577.
Barkhem, T., et al., "Differential response of estrogen receptor α and estrogen receptor β to partial estrogen agonists/antagonists," *Molecular Pharmacology*, 1998, 54, 105-112.
Battaini, F., "Protein kinase C isoforms as therapeutic targets in nervous system disease states," *Pharmacological Res.*, 2001, 44(5), 353-361.
Berendsen, H.H.G., et al., "Effect of tibolone and raloxifene on the tail temperature of oestrogen-deficient rats," *European J. of Pharmacology*, 2001, 419, 47-54.
Björklund, A., et al., "Dopamine-containing systems in the CNS," *Elsevier Science Publishers B.V.*, 1984, Chapter 3, 55-122.
Carr, D.B., et al., "Serotonin receptor activation inhibits sodium current and dendritic excitability in prefrontal cortex via a protein kinase C-dependent mechanism," *J. of Neuroscience*, 2002, 22(16), 6846-6855.
Chamberlain, M.C., et al., "Treatment of leptomeningeal metastasis with intraventricular administration of depot cytarabine (DTC 101)-A Phase I study," *Arch Neurol.*, 1993, 50, 261-264.
Chambliss, K.L., et al., "Estrogen modulation of endothelial nitric oxide synthase," *Endocrine Reviews*, 2002, 23(5), 665-686.
Dave, J.R., et al., "Evidence that β-endorphin binds to specific receptors in rat peripheral tissues and stimulates the adenylate cyclase-adenosine 3', 5'-monophosphate system," *Endocrinology*, 1985, 117(4), 1389-1396.
Demotes-Mainard, J., et al., "Estrogens modulate the responsiveness of in vivo recorded striatal neurons to Iontophoretic application of dopamine in rats: role of $D_1$ and $D_2$ receptor activation," *J. of Neuroendocrinology*, 1990, 2(6), 825-832.
Doolan, C.M., et al., "Rapid non-genomic activation of cytosolic cyclic AMP-dependent protein kinase activity and $[Ca^{2+}]I$ by 17β-oestradiol in female rat distal colon," *British J. of Pharmacology*, 2000, 129, 1375-1386.
Dubal, D.B., et al., "Estradiol modulates bcl-2 in cerebral ischemia: a potential role for estrogen receptors," *J. of Neuroscience*, 1999, 19(15), 6385-6393.
Dubal, D.B., et al., Estrogen receptor α, not β, is a critical link in estrodiol-mediated protection against brain injury, *PNAS*, 2001, 98(4), 1952-1957.
Dutar, P., et al., "Pre- and postsynaptic $GABA_B$ receptors in the hippocampus have different pharmacological properties," *Neuron*, 1988, 1, 585-591.
Ferin, M., et al., "The hypothalamic control of the menstrual cycle and the role of endogenous pioid peptides," *Recent Progress in Hormone Research*, 1984, 40, 441-485.

(Continued)

*Primary Examiner*—Charanjit S. Aulakh
(74) *Attorney, Agent, or Firm*—Woodcock Washburn LLP

(57) ABSTRACT

The present disclosure concerns a new class of selective estrogen receptor modulators (SERMs). The disclosure also includes the identification of a previously unknown membrane associated estrogen receptor. Methods for making and using the disclosed SERMs are disclosed, including pharmaceutical formulations of the disclosed novel compounds in useful compositions.

28 Claims, 16 Drawing Sheets

OTHER PUBLICATIONS

Fitzpatrick, J.L., et al., "Estrogen-mediated neuroprotection against β-amyloid toxicity requires expression of estrogen receptor α or β and activation of the MAPK pathway," *J. of Neurochemistry*, 2002, 82, 674-682.

Gu, Q., et al., "17β-estradiol potentiates kainite-induced currents via activation of the cAMP cascade," *J. of Neuroscience*, 1996, 16(11), 3620-3629.

Gu, Q., et al., "Novel mechanism for non-genomic action of 17β-oestradiol on kainite-induced currents in isolated rat CA1 hippocampal neurons," *J. of Physiology*, 1998, 506(3), 745-754.

Harrison, N.L., et al., "Structure-activity relationships for steroid interaction with the γ-aminobutyric acid$_A$ receptor complex," *J. of Pharmacology & Experimental Therapeutics*, 1987, 241(1), 346-353.

Herbison, A.E., "Estrogen regulation of GABA transmission in rate preoptic area," *Brain Research Bulletin*, 1997, 44(4), 321-326.

Herbison, A.E., et al., "Distribution of estrogen receptor-immunoreactive cells in monkey hypothalamus: relationship to neurons containing luteinizing hormone-releasing hormone and tyrosine hydroxylase," *Neuroendocrinology*, 1995, 61, 1-10.

Herbison, A.E., et al., "Erratum-Lack of detection of estrogen receptor-α transcripts in mouse gonadotropin-releasing hormone neurons," *Endocrinology*, 2001, 142(1), 1 page.

Hökfelt, T., et al., "Distributional maps of tyrosine-hydroxylase-immunoreactive neurons in the rat brain," *Handbook of Chemical Neuroanatomy, Elsevier Science Publishers B.V.*, 1984, vol. 2, Chapter VI, 277-379.

Howell, S.B., et al., "Clinical applications of a novel sustained-release injectable drug delivery system: depoFoam™ technology," *The Cancer Journal*, 2001, 7(3), 219-227.

Jacobowitz, O., et al., "Stimulation of specific types of $G_s$-stimulated adenylyl cyclases by phorbol ester treatment," *J. of Biological Chemistry*, 1993, 268(6), 3829-3832.

Jarry, H., et al., "The inhibitory effect of β-endophin on LH release in ovariectomized rats does not involve the preoptic GABAergic system," *Experimental & Clinical Endocrinology & Diabetes*, 1995, 103, 317-323.

Katre, N.V., et al., "Multivesicular liposome (DepoFoam) technology for the sustained delivery of insulin-like growth factor-1 (IGF-1)," *J. of Pharmaceutical Sciences,*, 1998, 87(11), 1341-1346.

Katzenellenbogen, J.A., et al., "Facile geometric isomerization of phenolic non-steroidal estrogens and antiestrogens: limitations to the interpretation of experiments characterizing the activity of individual isomers," *J. Steroid Biochem.*, 1985, 22(5), 589-596.

Kelly, M.J., et al., "Identification of estrogen-responsive LHRH neurons in guinea pig hypothalamus," *Brain Research Bulletin*, 1984, 12, 399-407.

Kelly, M.J., et al., "Opioids hyperpolarize β-endorphin neurons via μ-receptor activation of a potassium conductance," *Neuoendocrinology*, 1990, 52, 268-275.

Kelly, M.J., et al., "Rapid effects of estrogen to modulate G protein-coupled receptors via activation of protein kinase A and protein kinase C pathways," *Steroids*, 1999, 64, 64-75.

Kelly, M.J., et al., "Electrophysiological analysis of neuroendocrine neuronal activity in hypothalamic slices," *Methods in Neurosciences*, 1994, 20, 47-67.

Kelly, M.J., et al., "Estrogen suppresses μ-opioid-and GABA$_B$-mediated hyperpolarization of hypothalamic arcuate neurons," *J. of Neuroscience*, 1992, 12(7), 2745-2750.

Kelly, M.J., et al., "Estrogen modulation of G-protein-coupled receptors," *TEM*, 1999, 10(9), 369-374.

Lagrange, A.H., et al., "Modulation of G-protein-coupled receptors by an estrogen receptor that activates protein kinase A," *Molecular Pharmacology*, 1997, 51, 605-612.

Lagrange, A.H., et al., "The potency of μ-opioid hyperpolarization of hypothalamic arcuate neurons is rapidly attenuated by 17β-estradiol," *J. of Neuroscience*, 1994, 14(10), 6196-6204.

Lagrange, A.H., et al., "Estrogen rapidly attenuates a GABA$_B$, response in hypothalamic neurons," *Neuroendocrinology*, 1996, 64, 114-123.

Langrange, A.H., et al., "Estradiol-17β and μ-opioid peptides rapidly hyperpolarize GnRH neurons: a cellular mechanism of negative feedback?," *Endocrinology*, 1995, 136(5), 2341-2344.

Lambert, J.J., et al., "Neurosteroids and GABA$_A$ receptor function," *TiPS*, 1995, 16, 295-303.

Leranth, C., et al., "Transmitter content and afferent connections of estrogen-sensitive progestin receptor-containing neurons in the primate hypothalamus," *Neuroendocrinology*, 1992, 55, 667-682.

Levin, E.R., et al., "Genome and Hormones: gender differences in physiology invited review: cell localization, physiology, and nongenomic actions of estrogen receptors," *J.Appl. Physiol.*, 2001, 1860-1867.

Lin, W.-W., et al., "Distinct PKC isoforms mediate the activation of cPLA$_2$ and adenylyl cyclase by phorbol ester in RAW264.7 macrophages," *British J. of Pharmacology*, 1998, 125, 1601-1609.

Loose, M.D., et al., "Membrane properties and response to opioids of identified dopamine neurons in the guinea pig hypothalamus," *J. of Neuroscience*, 1990, 10(11), 3627-3634.

Loose, M.D., et al., "Neurons in the rat arcuate nucleus are hyperpolarized by GABA$_B$ and μ-opioid receptor agonists: evidence for convergence at a ligand-gated potassium conductance," *Neuroendocrinology*, 1991, 54, 537-544.

Martiny-Baron, G., et al., "Selective inhibition of protein kinase C isozymes by the indolocarbazole Gö 6976," *J. of Biological Chemistry*, 1993, 268(13), 9194-9197.

McEwen, B.S., "Genome and Hormones: gender differences in physiology invited review: estrogens effects on the brain: multiple sites and molecular mechanisms," *J. Appl. Physiol.*, 2001, 91, 2785-2801.

Merchenthaler, I., et al., "The effect of estrogens and antiestrogens in a rat model for hot flush," *Maturitas-The European Menopause Journal*, 1998, 30, 307-316.

Mermelstein, P.G., et al., "Estradiol reduces calcium currents in rat neostriatal neurons via a membrane receptor," *J. of Neuroscience*, 1996, 16(2), 595-604.

Mitsushima, D., et al., "Role of glutamic acid decarboxylase in the prepubertal inhition of the luteinizing ormone releasing hormone release in femal rhesus monkeys," *J. of Neuroscience*, 1996, 16(8), 2563-2573.

Mittal, S., et al., "Structure-activity relationship of estrogens: receptor affinity and estrogen antagonist activity of certain (E)-and (Z)-1,2,3-triaryl-2-propen-1-ones[1,2]," *J. Med. Chem.*, 1985, 28, 492-497.

Mons, N., et al., "Immunological assessment of the distribution of type VII adenylyl cyclase in brain," *Brain Research*, 1998, 788, 251-261.

Morrell, J.I., et al., "A subset of β-endorphin-or dynorphin-containing neurons in the medial basal hypothalamus accumulates estradiol," *Neuroendocrinology*, 1985, 41, 417-426.

Neill, J.D., "Neuroendocrine regulation of prolactin secretion," *Frontiers in Neuroendocrinology*, 1980, 6, Chapter 5, 129-155.

Nelson, E.J., et al., "Ethanol-induced phosphorylation and potentiation of the activity of type 7 adenylyl cyclase," *J. of Biological Chemistry*, 2003, 278(7), 4552-4560.

Pan, Y., et al., "A comparison of oral micronized estradiol with soy phytoestrogen effects on tail skin temperatures of ovariectomized rats," *J. of the North American Menopause Society*, 2001, 8(3), 171-174.

Paradiso, K., et al., "The C terminus of the human nicotinic α4β2 receptor forms abinding site required for potentiation by an estrogenic steroid," *J. Neuroscience*, 2901, 21(17), 6561-6568.

Pieroni, J.P., et al., "Singal recognition and integration by $G_s$-stimulated adenylyl cyclases," *Current Opinion in Neurobiology*, 1993, 3, 345-351.

Polanczyk, M., et al., "The protective effect of 17 β-estradiol on experimental autoimmune encephalomyelitis is mediated through estrogen receptor-α," *Am. J. of Pathology*, 2003, 163(4), 1599-1605.

Prokai, L., et al., "Synthesis and biological evaluation of 17β-alkoxyestra-1,3,5(10)-trienes as potential neuroprotectants against oxidative stress," *J. Med. Chem.*, 2001, 44, 110-114.

Qiu, J., et al., "Rapid signaling of estrogen in hypothalamic neurons involves a novel G-protein-coupled estrogen receptor that activates protein kinase C," *J. of Neuroscience*, 2003, 23(29), 9529-9540.

Razandi, M., et al., "Cell membrane and nuclear estrogen receptors (ERs) originate from a single transcript: studies of ERα and ERβ expressed in Chinese hamster ovary cells," *Molecular Endocrinology*, 1999, 307-319.

Rupprecht, R., et al., "Neuroactive steroids; mechanisms of action and neuropsychopharmacological," *TINS*, 1999, 22(9), 410-416.

Seltzer, A.M., et al., "Restraining action of GABA on estradiol-induced LH surge in the rat: GABA activity in brain nuclei and effects of GABA mimetics in the medial preoptic nucleus," *Neuroendocrinology*, 1992, 55, 28-34.

Sherwin, B.B., "Estrogen and cognitive functioning in women," *Endocrine Reviews*, 2003, 24(2), 133-151.

Simonian, S.X., et al., "Identification and characterization of estrogen receptor α-containing neurons projecting to the vicinity of the gonadotropin-releasing hormone perikarya in the rostral preoptic area of the rat," *J. of Comparative Neurology*, 1999, 411, 346-358.

Simpkins, J.W., et al., "Role of nonfeminizing estrogens in brain protection from cerebral ischemia: An animal model of Alzheimer's Disease neuropathology," *Ann. N.Y. Acad. Sci.*, 2005, 1052, 233-242.

Singh, M., et al., "Estrogen-induced activation of mitogen-activated protein kinase in cerebral cortical explants: convergence of estrogen and neurotrophin signaling pathways," *J. of Neuroscience*, 1999, 19(4), 1179-1188.

Singh, M., "Estrogen-induced activation of the mitogen-activated protein kinase cascade in the cerebral cortex of estrogen receptor-α knock-out mice," *J. of Neuroscience*, 2000, 20(5), 1694-1700.

Stackman, R.W., et al., "Small conductance $Ca^{2+}$-activated $K^+$ channels modulate synaptic plasticity and memory encoding," *J. of Neuroscience*, 2002, 22(23), 10163-10171.

Sterns, V., et al., "Hot flashes," *The Lancet*, 2002, 360, 1851-1861.

Sullivan, K.A., et al., "Gonadotropin-releasing hormone neurons in the rhesus macaque are not immunoreactive for the estrogen receptor," *Brain Research*, 1995, 198-200.

Takano, K., et al., "Activation of G protein-coupled $K^+$ channels by dopamine in human GH-producing cells," *American Physiological Society*, 1994, E318-E325.

Tanaka, C., et al., "The protein kinase C family for neuronal signaling," *Annu. Rev. Neruosci.*, 1994, 17, 551-567.

Taniyama, K., et al., "Activation of protein kinase C suppresses the γ-aminobutyric $acid_B$ receptor-mediated inhibition of the vesicular release of noradrenaline and acetylcholine," *Journal of Neurochemistry*, 1992, 1239-1245.

Toran-Allerand, C.D., et al., "ER-X: a novel, plasma membrane-associated, putative estrogen receptor that is regulated during development and after ischemic brain injury," *J. of Neuroscience*, 2002, 22(19), 8391-8401.

Valverde, M.A., et al., "Acute activation of maxi-K channels (hSlo) by estradiol binding to the β subunit," *Science*, 1999, 285, 1929-1931.

Vogel, P., et al., "Improved resuscitation after cardiac arrest in rats expressing the baculovirus caspase inhibitor protein p35 in central neurons," *Anesthesiology*, 2003, 99, 112-121.

Wade, C.B., et al., "Estrogen receptor (ER)α and ERβ exhibit unique pharmacologic properties when coupled to activation of the mitogen-activated protein kinase pathway," *Endocrinology*, 2001, 142(6), 2336-2342.

Wagner, E.J., et al., "Neurochemical evidence that estrogen-induced suppression of kappa-opioid-receptor-mediated regulation of tuberoinfundibular dipaminergic neurons is prolactin-independent," *Neuroendocrinology*, 1994, 59, 197-201.

Wagner, E.J., et al., "The role of intrinsic and agonist-activated conductances in determining the firing patterns of preoptic area neurons in the guinea pig," *Brain Research*, 2000, 879, 29-41.

Wagner, E.J., et al., "A powerful $GABA_B$ receptor-mediated inhibition of GABAergic neurons in arcuate nucleus," *NeuroReport*, 1999, 10, 2681-2687.

Wagner, E.J., et al., "Estrogen biphasically modifies hypothalamic GABAergic function concomitantly with negative and positive control of luteinizing hormone release," *J. of Neuroscience*, 2001, 21(6), 2085-2093.

Watson, R.E., Jr., et al., "Further evidence that most luteinizing hormone-releasing hormone neurons are not directly estrogen-responsive: simultaneous localization of luteinizing hormone-releasing hormone and estrogen receptor immunoreactivity in the guinea-pig brain," *J. of Neuroendocrinology*, 1992, 4(3), 311-317.

Watters, J.J., et al., "Rapid membrane effects of steroids in neuroblastoma cells: effects of estrogen on mitogen activated protein kinase signaling cascade and c-fos immediate early gene transcription," *Endocrinology*, 1997, 138(9), 4030-4033.

Way, K.J., et al., "Identification of PKC-isoform-specific biological actions using pharmacological approaches," *Trends Pharmacol. Sci.*, 2000, 21, 181-187.

Weatherman, R.V., et al., "Differential SERM activation of the estrogen receptors (ERα and ERβ) at AP-1 sites," *Chemistry & Biology*, 2001, 8, 427-436.

Wetzel, C.H.R., et al., "Functional antagonism of gonadal steroids at the 5-hydroxytryptamine type 3 receptor," *Molecular Endocrinology*, 1998, 1441-1451.

Ye, Q., et al., "DepoFoam™ technology: a vehicle for controlled delivery of protein and peptide drugs," *J. of Controlled Release*, 2000, 64, 155-166.

Yoshimura, M., et al., "Type-specific stimulation of adenylylcyclase by protein kinase C," *J. of Biological Chemistry*, 1993, 268(7), 4604-4607.

Zaulyanov, L.L., et al., "Glutamate receptor requirement for neuronal death from anoxia-reoxygenation: an *invitro* model for assessment of the neuroprotective effects of estrogens," *Cellular & Molecular Neurobiology*, 1999, 19(6), 705-718.

Zhu, Y., et al., "Cloning, expression, and characterization of a membrane progestin receptor and evidence it is an intermediary in meiotic maturation of fish oocytes," *PNAS*, 2003, 100(5), 2231-2236.

\* cited by examiner

SEQUENCE LISTING

<160> NUMBER OF SEQ ID NOS: 16

<210> SEQ ID NO 1
<211> LENGTH: 18
<212> TYPE: DNA
<213> ORGANISM: Cavia

<400> SEQUENCE: 1
ggctctggtg atggaata                                         18

<210> SEQ ID NO 2
<211> LENGTH: 19
<212> TYPE: DNA
<213> ORGANISM: Cavia

<400> SEQUENCE: 2
cagaatcacg ctgtctgtt                                        19

<210> SEQ ID NO 3
<211> LENGTH: 20
<212> TYPE: DNA
<213> ORGANISM: Cavia

<400> SEQUENCE: 3
tccacgttat actggttcac                                       20

<210> SEQ ID NO 4
<211> LENGTH: 19
<212> TYPE: DNA
<213> ORGANISM: Cavia

<400> SEQUENCE: 4
ttgcatcact gaagctctc                                        19

<210> SEQ ID NO 5
<211> LENGTH: 20
<212> TYPE: DNA
<213> ORGANISM: Cavia

<400> SEQUENCE: 5
tgtttgtgcc aaagctcatc                                       20

```
<210> SEQ ID NO 6
<211> LENGTH: 20
<212> TYPE: DNA
<213> ORGANISM: Cavia

<400> SEQUENCE: 6
gtgtcttgca gttgcatagt                                           20

<210> SEQ ID NO 7
<211> LENGTH: 20
<212> TYPE: DNA
<213> ORGANISM: Cavia
<300> PUBLICATION INFORMATION:
<308> DATABASE ACCESSION NUMBER: S78260
<309> DATABASE ENTRY DATE: 2000-08-14
<313> RELEVANT RESIDUES: (40)..(59)

<400> SEQUENCE: 7
ctggccttgc tgcttcagat                                           20

<210> SEQ ID NO 8
<211> LENGTH: 20
<212> TYPE: DNA
<213> ORGANISM: Cavia
<300> PUBLICATION INFORMATION:
<308> DATABASE ACCESSION NUMBER: S78260
<309> DATABASE ENTRY DATE: 2000-08-14
<313> RELEVANT RESIDUES: (363)..(382)

<400> SEQUENCE: 8
atggagtagg agcgcttgtc                                           20

<210> SEQ ID NO 9
<211> LENGTH: 20
<212> TYPE: DNA
<213> ORGANISM: Cavia porcellus

<400> SEQUENCE: 9
catccactgg tgctgccaag                                           20

<210> SEQ ID NO 10
<211> LENGTH: 20
<212> TYPE: DNA
<213> ORGANISM: Cavia porcellus

<400> SEQUENCE: 10
gtcctcggtg tagcccaaga                                           20

<210> SEQ ID NO 11
<211> LENGTH: 20
<212> TYPE: DNA
<213> ORGANISM: Homo sapiens
<300> PUBLICATION INFORMATION:
<308> DATABASE ACCESSION NUMBER: L07861
<309> DATABASE ENTRY DATE: 1993-11-02
<313> RELEVANT RESIDUES: (1127)..(1146)
```

```
<400> SEQUENCE: 11
aaaggcagct tcgggaaggt                                               20

<210> SEQ ID NO 12
<211> LENGTH: 20
<212> TYPE: DNA
<213> ORGANISM: Homo sapiens
<300> PUBLICATION INFORMATION:
<308> DATABASE ACCESSION NUMBER: L07861
<309> DATABASE ENTRY DATE: 1993-11-02
<313> RELEVANT RESIDUES: (1357)..(1376)

<400> SEQUENCE: 12
tggatgtggt acatcaggtc                                               20

<210> SEQ ID NO 13
<211> LENGTH: 21
<212> TYPE: DNA
<213> ORGANISM: Cavia

<400> SEQUENCE: 13
ctgttcggca agtttgacca g                                             21

<210> SEQ ID NO 14
<211> LENGTH: 19
<212> TYPE: DNA
<213> ORGANISM: Cavia

<400> SEQUENCE: 14
tgacgccaca cagcacatt                                                19

<210> SEQ ID NO 15
<211> LENGTH: 11
<212> TYPE: PRT
<213> ORGANISM: Artificial
<220> FEATURE:
<223> OTHER INFORMATION: Synthetic Construct

<400> SEQUENCE: 15

Leu Gly Leu Asn Leu Lys Glu Tyr Asn Leu Val
1               5                   10

<210> SEQ ID NO 16
<211> LENGTH: 11
<212> TYPE: PRT
<213> ORGANISM: Artificial
<220> FEATURE:
<223> OTHER INFORMATION: Synthetic Construct

<400> SEQUENCE: 16

Cys Arg Met His Leu Arg Gln Tyr Glu Leu Leu
1               5                   10
```

DEVELOPMENT OF NEW SELECTIVE ESTROGEN RECEPTOR MODULATORS

CROSS-REFERENCE TO RELATED APPLICATION

This application claims benefit under 35 USC 119(e) of U.S. Provisional Application No. 60/513,235, filed Oct. 21, 2003, the entirety of which is herein incorporated by reference.

ACKNOWLEDGEMENT OF GOVERNMENT SUPPORT

This invention was made with Government support under Grant Nos. NS 35944, NS 38809, DA 05158, DA 10703, and DK 57574. The Government has certain rights in this invention.

FIELD

This disclosure concerns novel compounds and methods for their use, including selective estrogen receptor modulators and methods for making such selective estrogen receptor modulators.

BACKGROUND

Estrogens are an important class of steroidal hormones that stimulates the development and maintenance of fundamental sexual characteristics in humans. In addition, estrogens have been demonstrated to affect a variety of diverse biological processes. Many of the incidental effects of estrogens are positive, including the maintenance of bone density, central nervous system function and preservation of memory. However, estrogens also have been demonstrated to have serious negative effects, including promoting the development of breast and endometrial cancers.

Based upon a life expectancy of nearly eighty years in the United States, a woman can expect to spend about a third of her lifetime in a post-menopausal state. A woman's estrogen levels drop dramatically during menopause and menopausal women often experience many side affects associated with the reduction in estrogen production. To treat these conditions, physicians often prescribe hormone replacement therapy, which primarily consists of the administration of estrogen in combination with progestin.

In light of the more serious side effects associated with current hormone replacement therapy, including increased risk of ischemic stroke, myocardial infarction, thromboembolism, cerebrovascular disease, and endometrial carcinoma, a significant amount of research has been carried out to identify effective nonsteroidal estrogen and antiestrogenic compounds.

A large number of compounds have been described that either mimic or block the effects of the most potent estrogen, 17β-estradiol. Compounds that bind to an estrogen receptor and stimulate many of the same biological effects as 17β-estradiol are termed "estrogen receptor agonists." Compounds that inhibit the binding of 17β-estradiol to an estrogen receptor or interfere with the effects of 17β-estradiol binding to an estrogen receptor are referred to as "estrogen receptor antagonists." Compounds that affect different estrogen receptors with different potencies are typically referred to as selective estrogen receptor modulators (SERMs). SERMs may act as either agonists or antagonists to selectively modulate one or more estrogen receptors. Certain SERM compounds have mixed estrogenic and anti-estrogenic activities and act as estrogen receptor agonists in some tissues and as estrogen receptor antagonists in other tissues.

Estrogens, such as 17β-estradiol, have been thought to exert their effects by binding to one of two nuclear estrogen receptors, (ER)α or (ER)β. Because (ER)α and (ER)β are found in different tissues and have been demonstrated to have different biological roles, researchers have focused on the development of SERMs that effect a response by selectively binding to either (ER)α or (ER)β.

Two examples of nonsteroidal SERMs that exhibit different activities towards (ER)α and (ER)β are tamoxifen and raloxifene. Tamoxifen and raloxifene have been developed for the treatment and/or prevention of osteoporosis, cardiovascular disease and breast cancer in addition to the treatment and/or prevention of a variety of other disease states. Both compounds have been shown to exhibit an osteoprotective effect on bone mineral density combined with a positive effect on plasma cholesterol levels and a greatly reduced incidence of certain types of cancer. Unfortunately, tamoxifen and raloxifene both induce side effects such as hot flushes and tamoxifen promotes life-threatening disorders, such as endometrial cancer.

The present disclosure includes novel nonsteroidal SERMs that elicit the desired effects of hormone replacement therapy without inducing the negative effects of hormone replacement therapy or those of known selective estrogen receptor modulators.

SUMMARY

The present disclosure includes novel compounds, compositions and methods for making and using the compounds and compositions. Generally, the disclosed compounds function as selective estrogen receptor modulators (SERMs). In one aspect, the compounds have Formula 1 and include hydrates and pharmaceutically acceptable prodrugs and salts thereof. Moreover, all chiral, diastereomeric and geometric isomeric forms of the disclosed Formulas are intended.

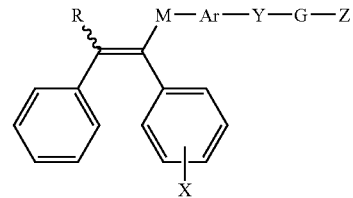

Formula 1

With reference to Formula 1, R can be E or Z with respect to M and R represents a hydrogen or a lower aliphatic group; X is an ortho, meta or para positioned hydrogen, hydroxyl, protected hydroxy, alkoxy, sulfhydryl, thioether, amino (—NR$^2$R$^3$ wherein R$^2$ and R$^3$ are independently hydrogen or lower alkyl) or a halogen; M comprises a ketone, amide or sulfonamide group. Ar represents an aromatic group and can be any aromatic group, including, without limitation, phenyl, biphenyl, 1-napthyl, 2-napthyl, and including heteroaryl groups, such as, by way of example, furan, thiophene, pyrrole, imidazole, oxazole, thiazole, pyridine, and quinoline groups. Y can be attached at any position, such as at the ortho, meta or para position relative to M. In one aspect, Y is a heteroatom, such as a nitrogen or oxygen. In certain embodiments of the disclosed SERMs according to Formula 2 Y represents a phenyl group.

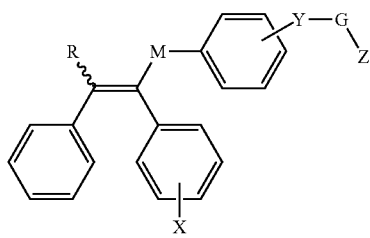

Formula 2

With continued reference to Formulas 1 and 2, G includes a linker group, such as a lower alkyl group, a hydrocarbon chain, an oligoethylene glycol chain or the like. In one embodiment of Formula 2 wherein G includes a lower alkyl group, G is an ethyl group. Z typically includes a heteroatom. In certain embodiments Z includes a charged moiety, for example an anionic group, such as a boronate, sulfate, sulfonate, phosphate, phosphonate or a carboxy group. In examples wherein Z includes a cationic group, the cationic group can be an amino group, such as a dimethylamino or piperidino group. In other examples Z includes a hydroxyl group. Examples of groups represented by the formula Y-G-Z include those wherein Y is a heteroatom, such as oxygen and the formula -G-Z represents, without limitation, one of the following:

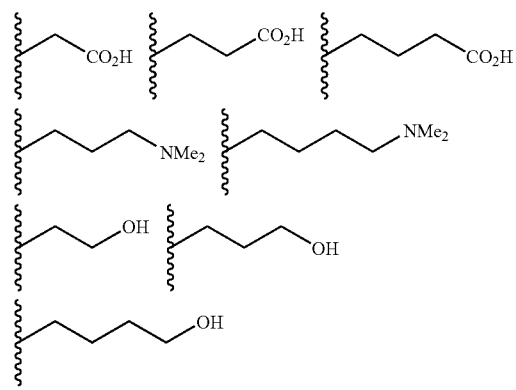

With reference to Formulas 1 and 2, M typically is one of an amide ketone or a sulfonamide group and more typically represents one of —C(O)—; —C(O)—NR$^1$—; or —SO$_2$NR$^1$—; wherein R$^1$ is hydrogen, a lower alkyl group or aralkyl group. Thus, examples of such compounds can be represented by Formula 3 wherein Q typically forms an amide or sulfonamide linkage (Q represents —SO$_2$— or CO).

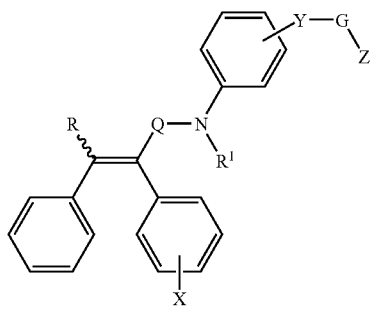

Formula 3

Thus, compounds according to Formula 3 can have, for example, Formula 4 or 5. With respect to Formulas 4 and 5, R, X, R$^1$, and Y are defined as above with respect to Formula 1.

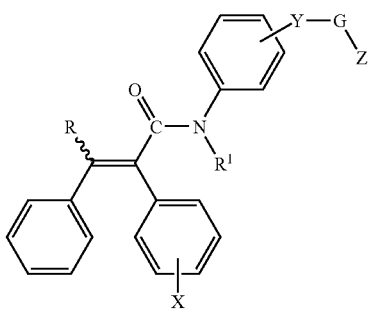

Formula 4

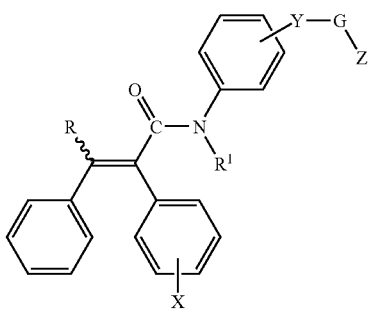

Formula 5

As indicated in the formulas above, the disclosed compounds include vinyl ketone derivatives, acrylamide derivatives and vinyl sulfonamide derivatives. Moreover, as illustrated in the structures above, the configuration about the vinyl group can be E or Z.

One aspect of the disclosure includes methods for synthesizing novel selective estrogen receptor modulators. In another embodiment, the method includes providing a starting material according to Formula 6, wherein G is a carboxy group, an activated carboxy group, a sulfonic acid group or an activated sulfonic acid group. The activated carboxy and sulfonic acid groups include any groups that can react with an amine or amine equivalent to form an amide or sulfonamide according to Formula 3 or Formula 4. Typically activated carboxy groups include acyl halides and activated esters. In particular examples, Y is a carboxy group, which has been activated for reaction with nucleophiles in situ. Similarly, typical activated sulfonic acid groups include sulfonyl halides, such as sulfonyl chlorides. Such activated sulfonic acid groups can be used to acylate a variety of amines, including primary and secondary amines.

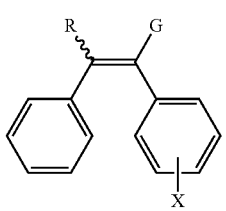

Formula 6

For example, one embodiment of a method for synthesizing novel estrogen receptor modulators is illustrated in Scheme 1. With reference to Scheme 1, Formula 7, variable Y indicates an anion or anion equivalent, such as a halogen, which can be subjected to lithium-halogen exchange conditions to give the corresponding carbanion. The carbanion can be used to introduce a carboxy group as illustrated in Formula 8. The carboxy group can be introduced, for example, as a protected carboxy equivalent, such as a protected chloroformate derivative. One example of such a reagent is allyl chloroformate, which can be used to introduce the carboxy group of Formula 8. Compounds according to Formula 8 are versatile synthetic intermediates because such compounds can be coupled with any primary or secondary amine to provide compounds according to Formula 9. Thus, compounds according to Formula 9, wherein $R^1$ and $R^2$ independently are selected from hydrogen, aliphatic, aryl or aralkyl groups, can be prepared by reacting compounds according to Formula 8 with the corresponding primary or secondary amine having the formula: $R^1R^2NH$. Typically at least one of $R^1$ and $R^2$ includes an aryl group, and examples of suitable amines including aryl groups include those wherein at least one of $R^1$ and $R^2$ is a phenyl group or a phenyl derivative.

Generally, the conversion of a compound having Formula 8 to a compound having Formula 9 according to the presently disclosed method includes using a coupling reagent to activate the carboxy group for reaction. Examples of such coupling reagents include, without limitation, carbodiimides, uronium salts, phosphonium salts, and the like. Examples of carbodiimides include, without limitation, dicyclohexylcarbodiimide, diisopropylcarbodiimide and 1-(3-dimethyl-aminopropyl)-3-ethylcarbodiimide hydrochloride (EDCI). Examples of uronium salts include 2-(1H-benzotriazole-1-yl)-1,1,3,3-tetramethyluronium hexafluorophosphate (HBTU) and 2-(1H-benzotriazole-1-yl)-1,1,3,3-tetramethyluronium tetrafluoroborate (TBTU). Examples of phosphonium salts include benzotriazole-1-yl-oxy-tris-pyrrolidino-phosphonium hexafluorophosphate (PyBop) and bromo-tris-pyrrolidino-phosphonium hexafluorophosphate (PyBrop). The conversion also optionally can employ additives, such as 4-dimethylaminopyridine (DMAP) and/or N-hydroxybenzotriazole (HOBt). In one embodiment, the disclosed synthesis, HBTU can be used in the presence of DMAP to couple amines to compounds having Formula 8.

Another aspect of the method is illustrated in Scheme 2. With reference to Scheme 2, the method includes providing a vinyl sulfonic acid according to Formula 11 and coupling a primary or secondary amine ($R^1R^2NH$) to provide a sulfonamide according to Formula 12. The coupling reaction can be accomplished in the presence of, for example, DCC, DIC, EDCI, HBTU, TBTU, PyBop or PyBrop. The conversion also optionally can employ additives, such as DMAP and/or HOBt.

Particular novel compounds included in the present disclosure bind to a previously unidentified, membrane associated estrogen receptor. Moreover, specific examples of these compounds selectively bind to the membrane associated estrogen receptor with greater affinity than they bind to the classical nuclear receptors, (ER)α and (ER)β. Therefore, one aspect of the disclosure includes a method for providing a selective agonist or antagonist of a membrane associated estrogen receptor.

The disclosure also includes methods and compositions for treating a variety of disorders, particularly those characterized by an estrogen deficiency such as those associated with ovarectomy, ovarian failure or menopause. Such conditions and disorders include, generally, those described as autonomic dysfunctions, cognitive decline, motor dysfunctions, mood disorders, eating disorders and cardiovascular diseases, as well as different types of disorders. In one aspect, the disclosed compounds exert prophylactic effects against certain types of injuries. For example, the compounds can be used as neuroprotectants. Indeed, compounds that agonize the membrane-associated estrogen receptor identified herein act as neuroprotectants to reduce neuronal cell death in response to ischemic stroke and inhibit reperfusion injury.

Particular compositions include at least one compound according Formula 1 as well as a second therapeutic compound. The second compound also can bind to an estrogen receptor. For example, in one embodiment the second compound is a SERM and in another embodiment the second compound is an estrogen, such as 17β-estradiol, or a progesterone, such as progestin.

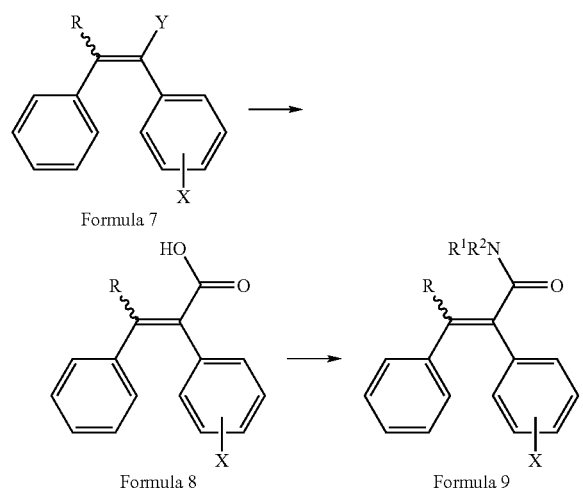

Figure 3A:
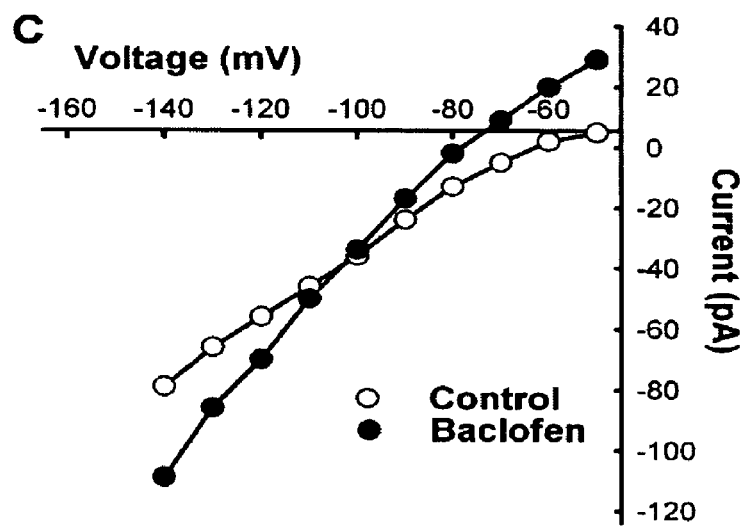
FIG. 3A is a graph illustrating the pre- and post-baclofen (5 μM) I/V relationships from a dopamine neuron.
Figure 3B:
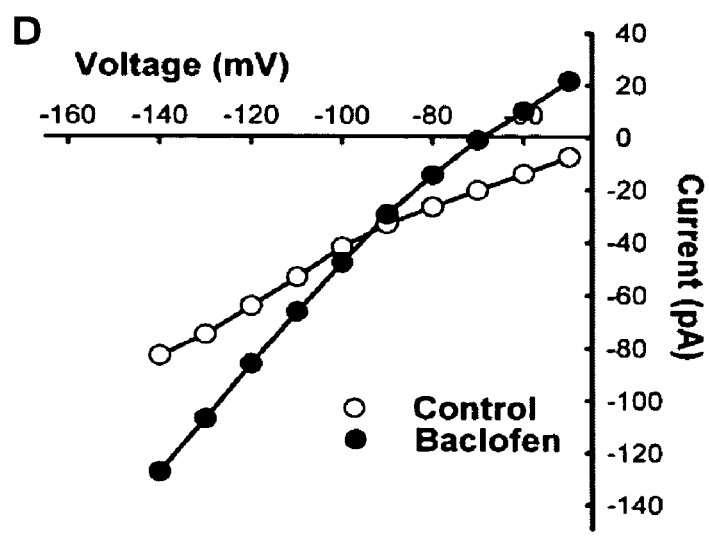

FIG. 3B is a graph of the pre- and post-baclofen I/V relationships following 17β-estradiol treatment in another cell illustrating the same reversal potential for the baclofen response.

Figure 4A:

FIG. 4A is an image showing the biocytin-streptavidin-Cy2 labeling of fusiform arcuate dopamine neuron that responded to estrogen.

Figure 4B:
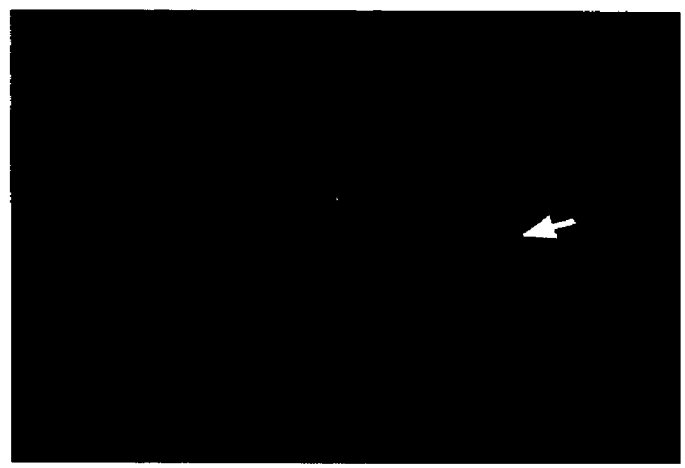

FIG. 4B is an image showing the immunocytochemical staining of tyrosine hydroxylase (TH) in the neuron imaged in FIG. 4A.

Figure 4C:
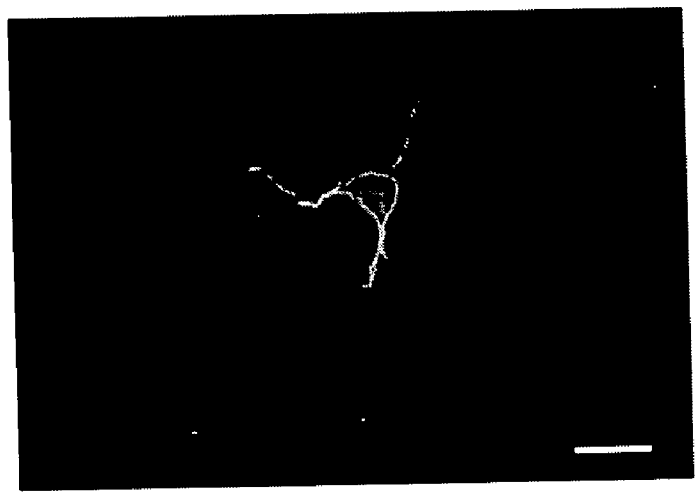

FIG. 4C is an image showing the biocytin-streptavidin-Cy2 labeling of a small pyramidal arcuate POMC neuron.

Figure 4D:

FIG. 4D is an image showing the immunocytochemical staining of β-endorphin in the neuron imaged in FIG. 4C.

Figure 5:
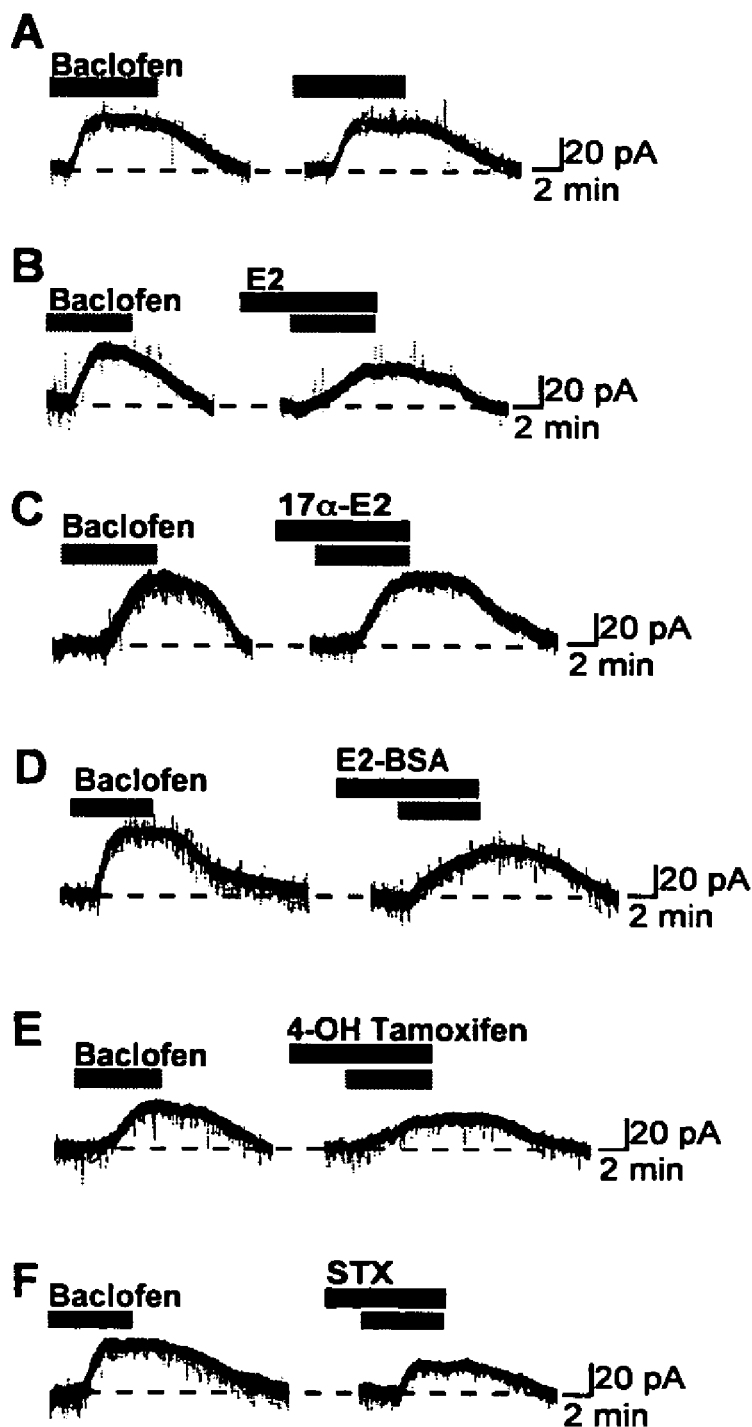

FIG. 5 includes representative traces of the $GABA_B$ responses before and after steroid treatment.

Figure 6:
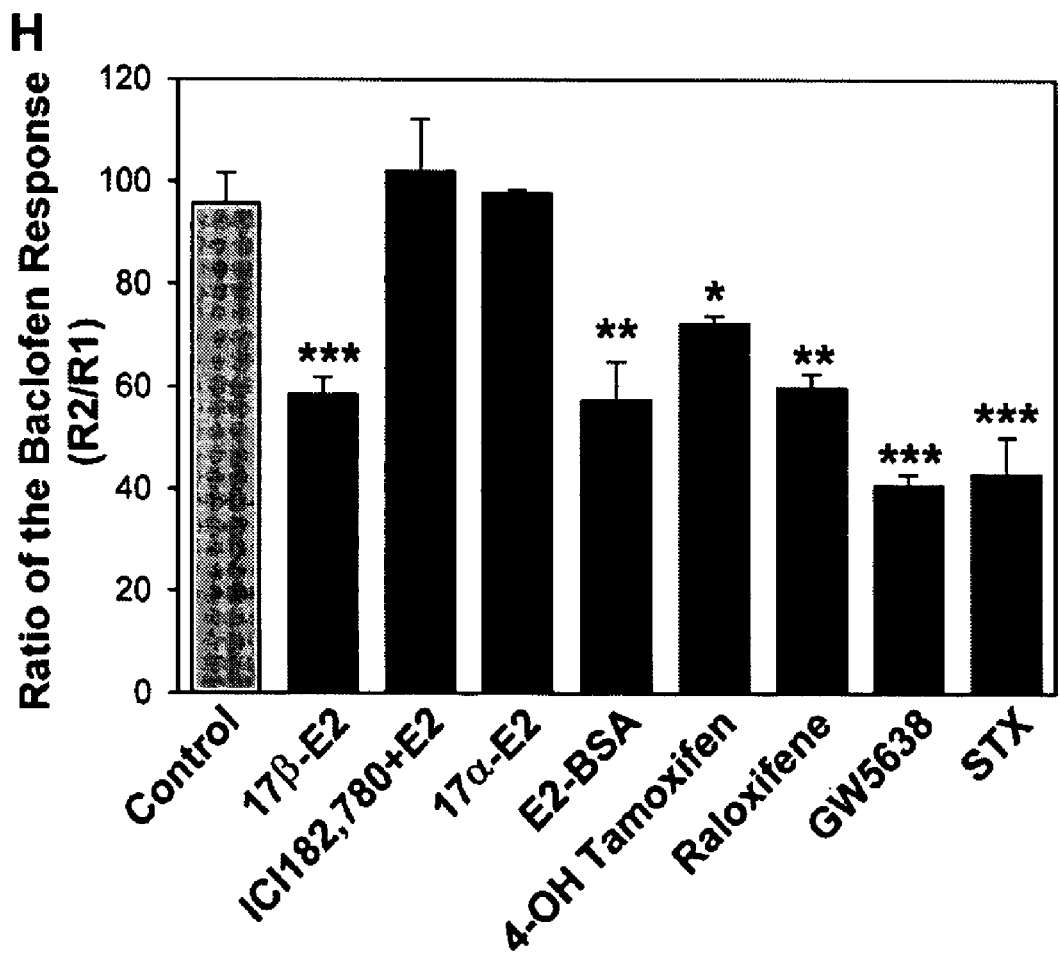

FIG. 6 includes bar graphs summarizing the effects of 17β-estradiol and SERMs on the baclofen response.

Figure 7A:
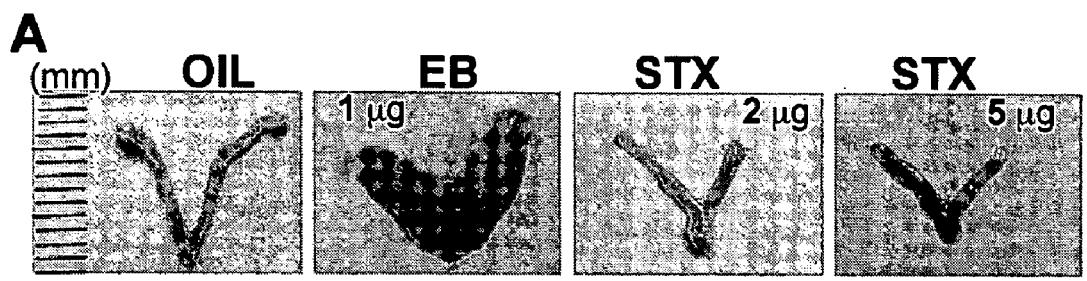

FIG. 7A compares uteri size following treatment with 17β-estradiol versus an exemplary SERM disclosed herein and shows that in 17β-estradiol-treated mice, there was a noticeable increase in uterine size after estradiol benzoate (EB), compared with oil-vehicle treatment or treatment with an exemplary SERM disclosed herein.

Figure 7B:
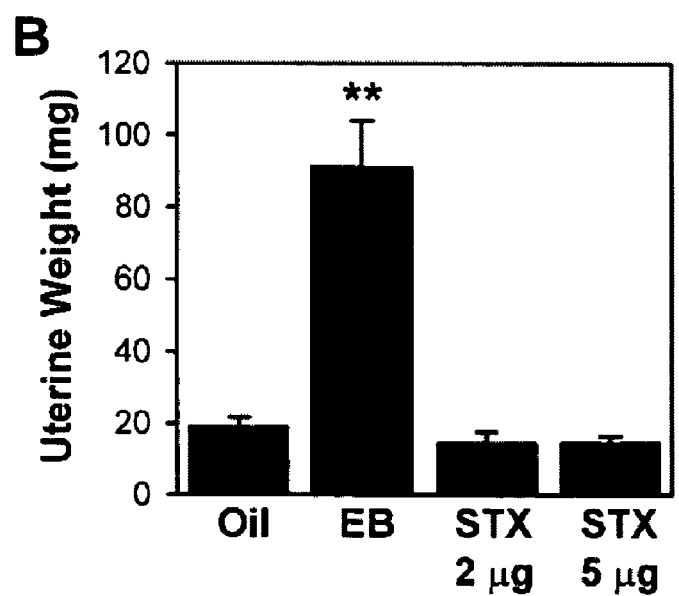

FIG. 7B is a bar graph recording the uterine weights for EB treated mice versus oil and SERM treated mice (n=3–5 mice/group).

Figure 8:
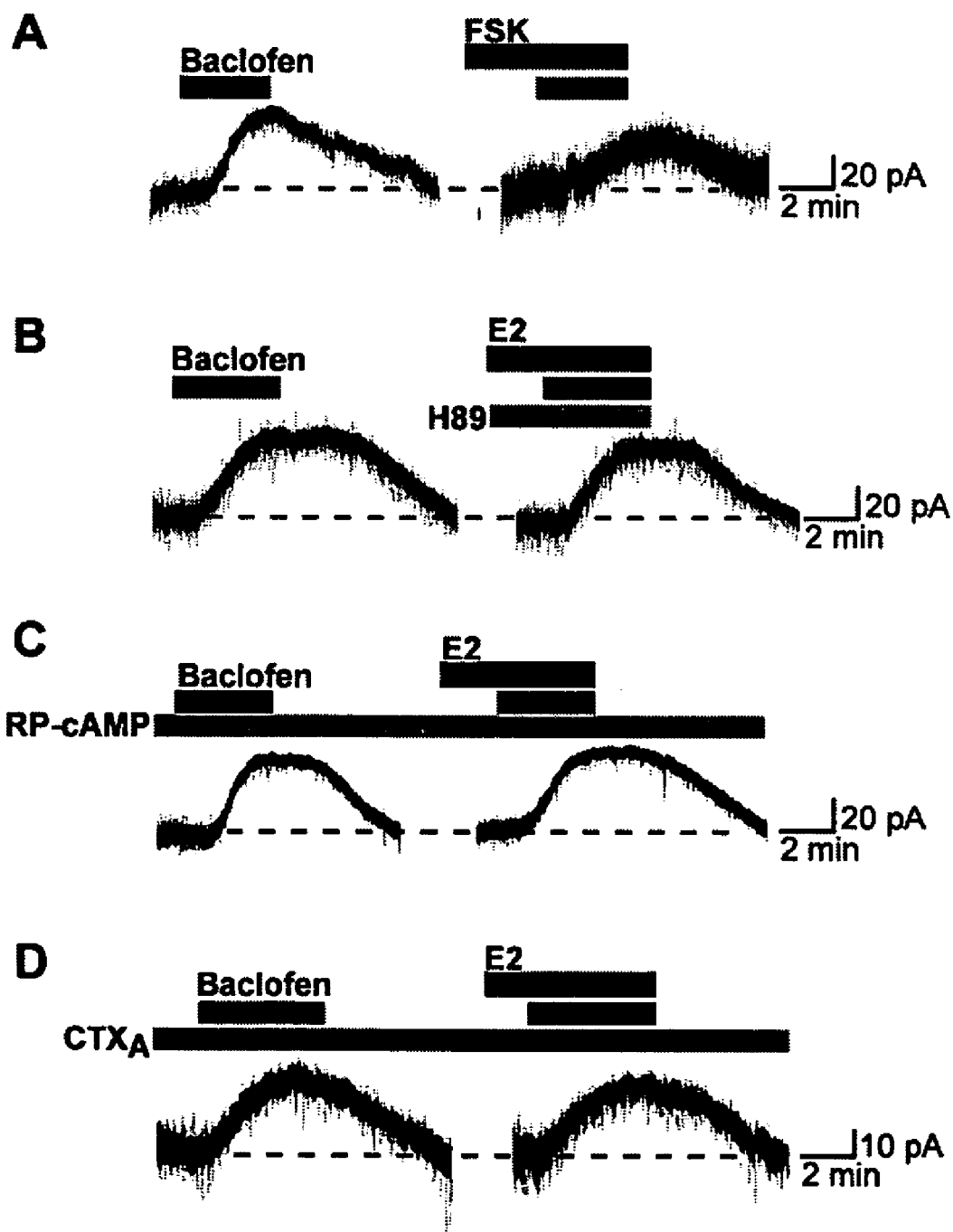

FIG. 8 includes representative traces of the baclofen responses in the presence of PKA activators or inhibitors and demonstrates that 17β-estradiol attenuation of the $GABA_B$ response involves protein kinase A.

Figure 9:
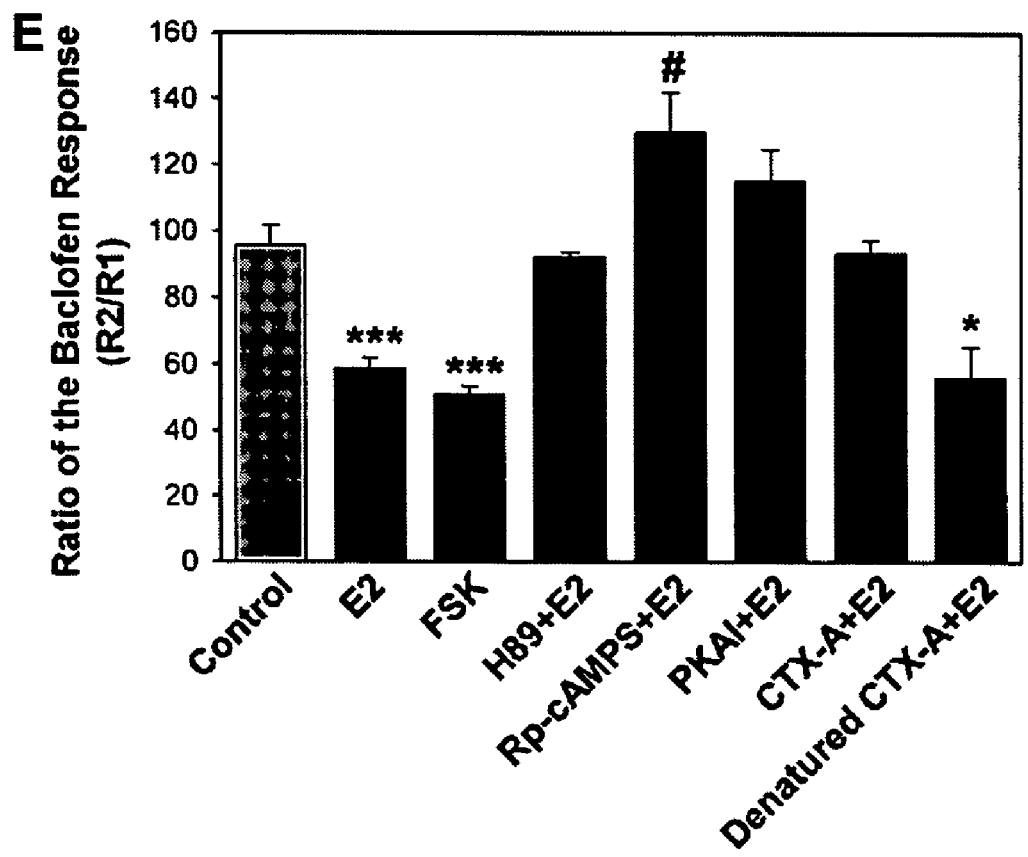

FIG. 9 is a bar graph summarizing the effects of protein kinase A (PKA) drugs on the baclofen response.

Figure 10:
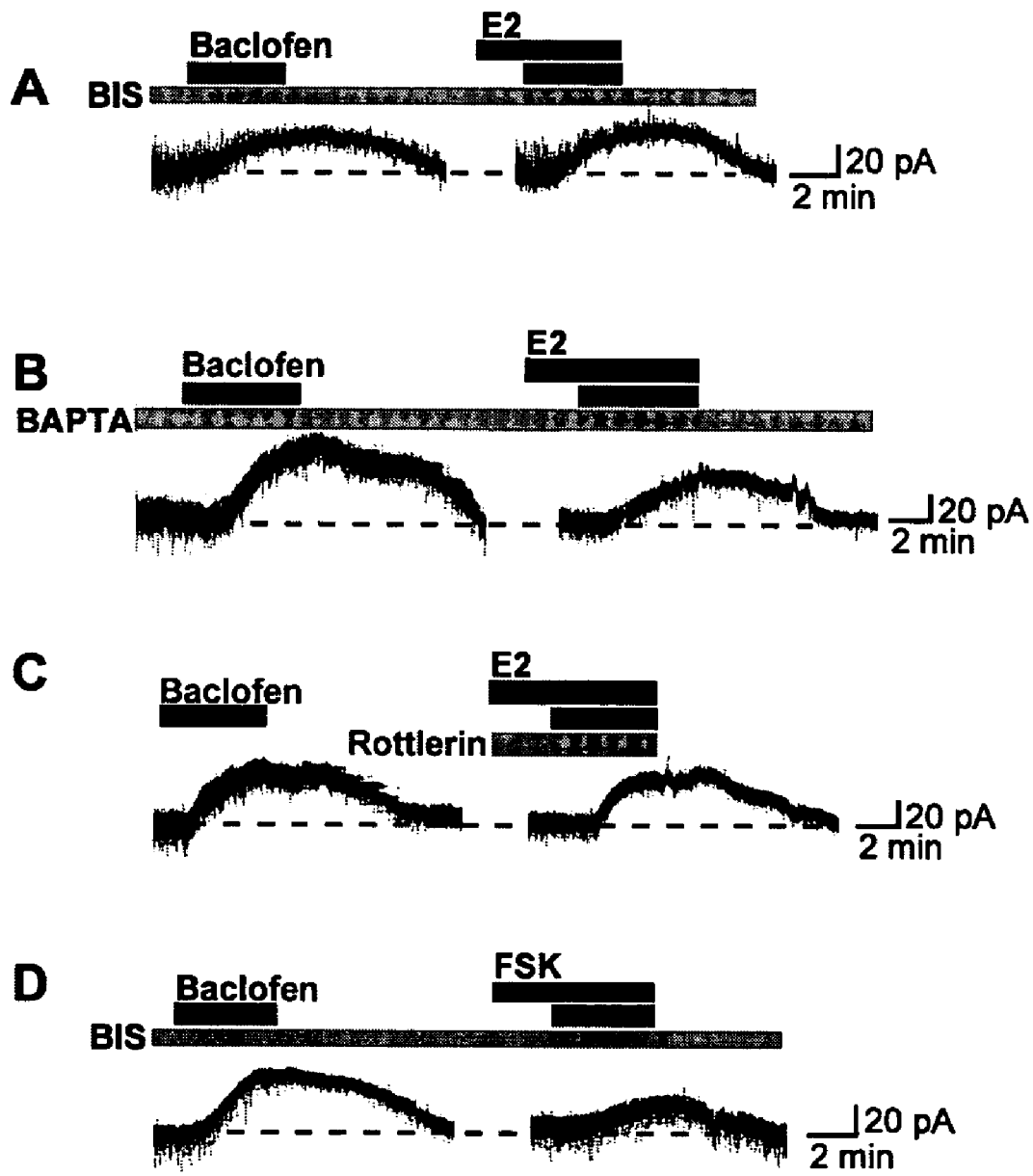

FIG. 10 includes representative traces of the baclofen responses in the presence of PKC inhibitors.

Figure 11:
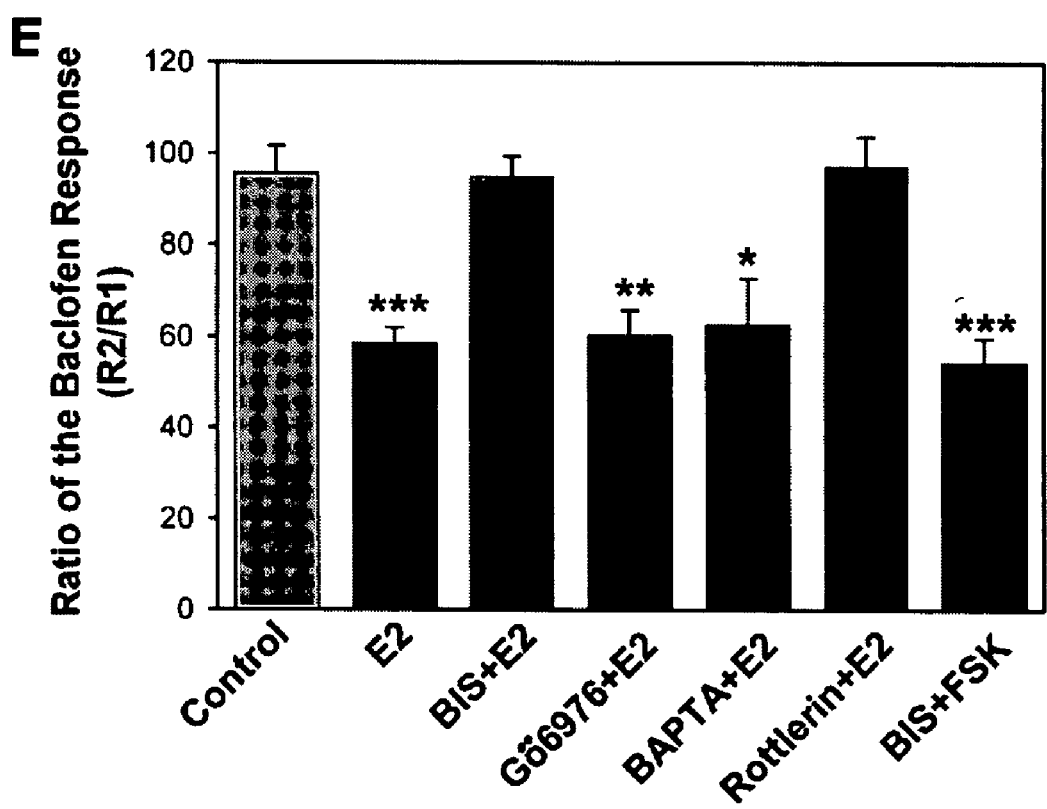

FIG. 11 is a bar graph summarizing the effects of protein kinase C (PKC) inhibitors on the baclofen response.

Figure 12:
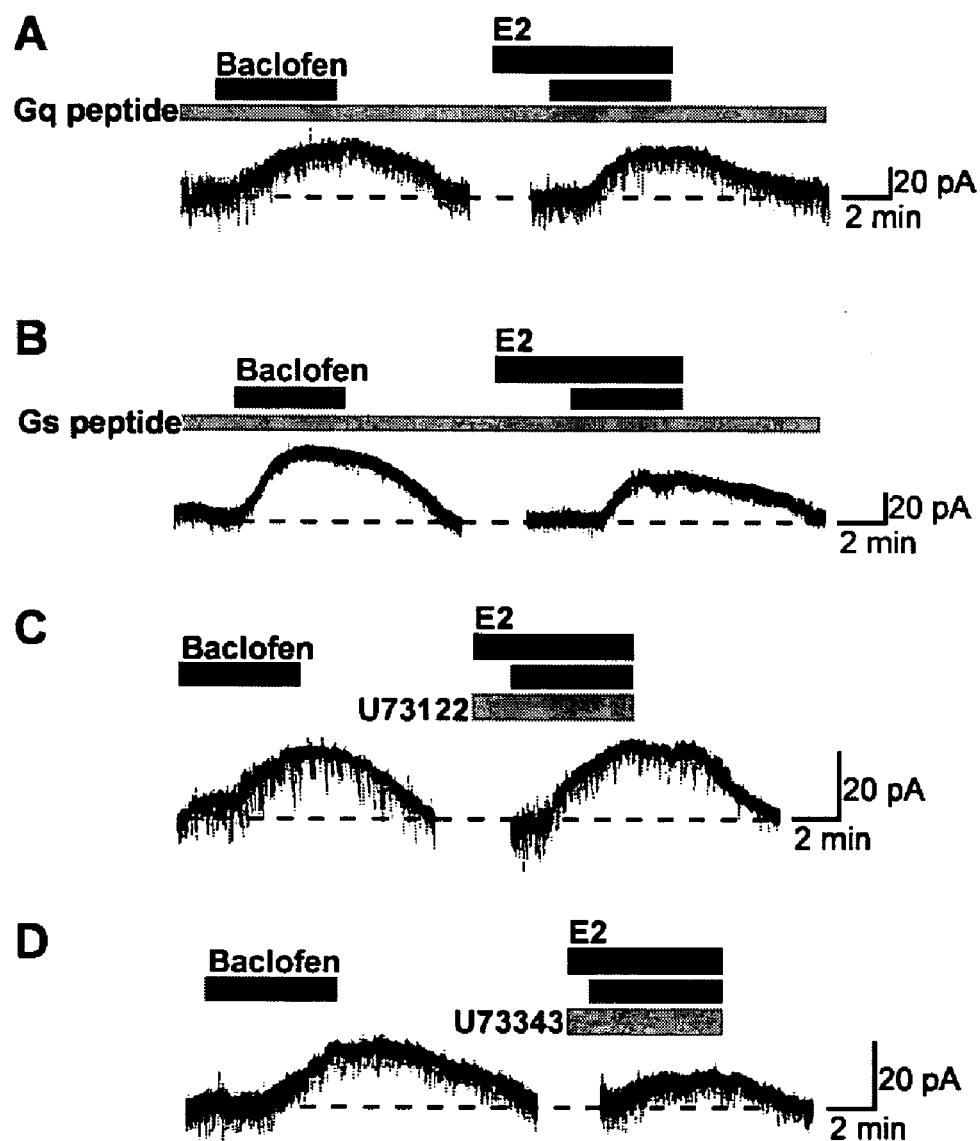

FIG. 12 includes representative traces of the baclofen responses in the presence of phospholipase C (PLC) and $G\alpha_q$ inhibitors.

Figure 13:
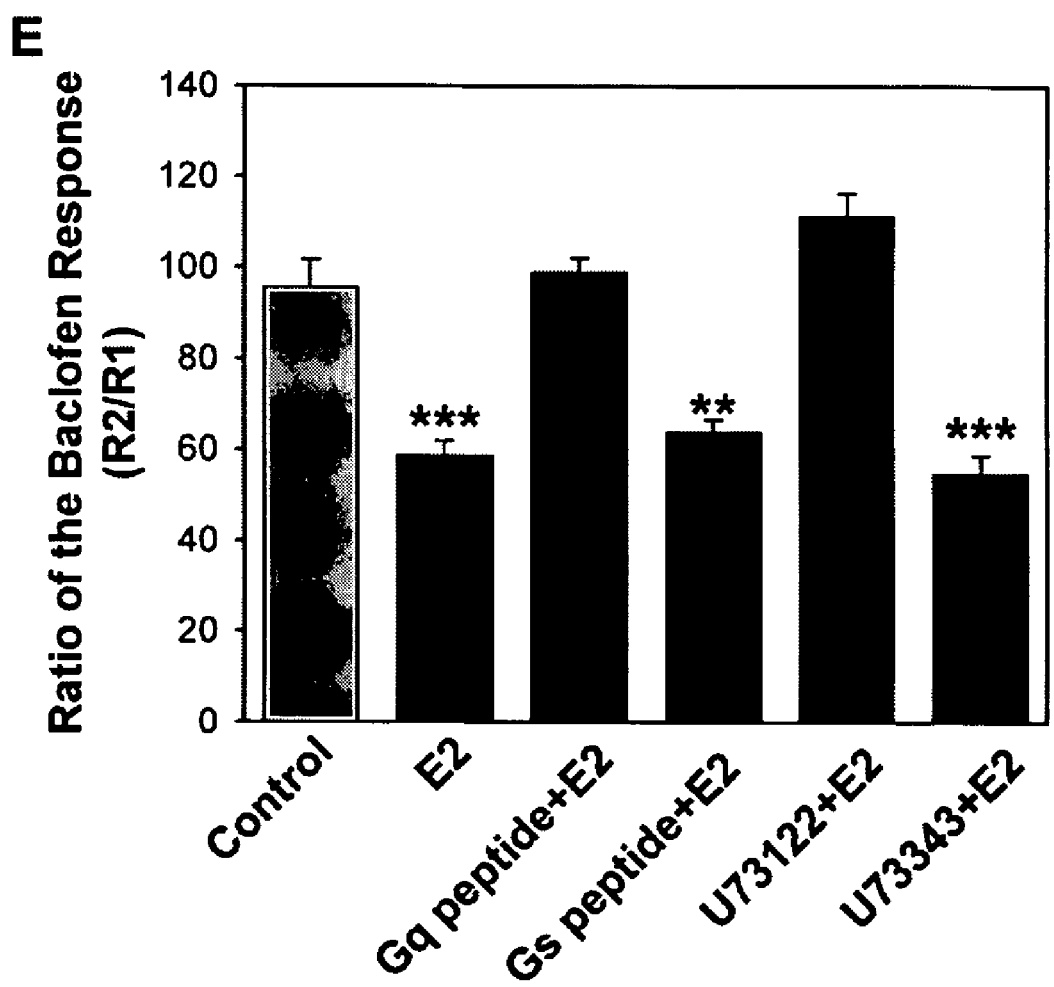

FIG. 13 is a bar graph summarizing the effects of the PLC and $G\alpha_q$ inhibitors.

Figure 14A:
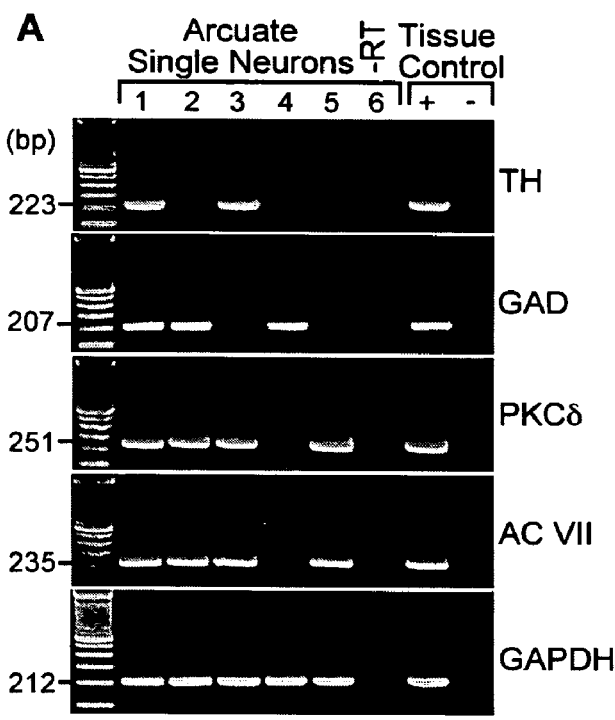

FIG. 14A is a representative gel illustrating that single arcuate neurons express mRNA for TH, GAD, PKCδ, AC VII and GAPDH.

Figure 14B:
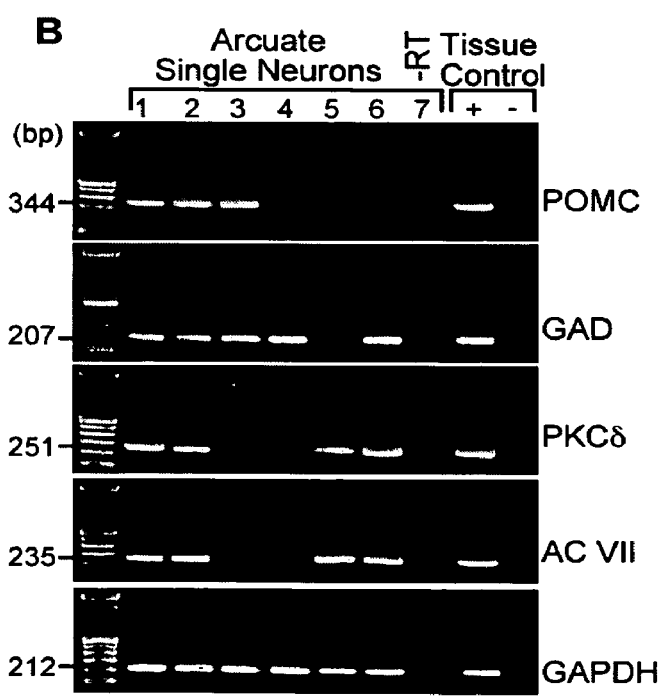

FIG. 14B is a representative gel illustrating that single arcuate neurons express mRNA for POMC, GAD, PKCδ, AC VII and GAPDH.

Figure 15:
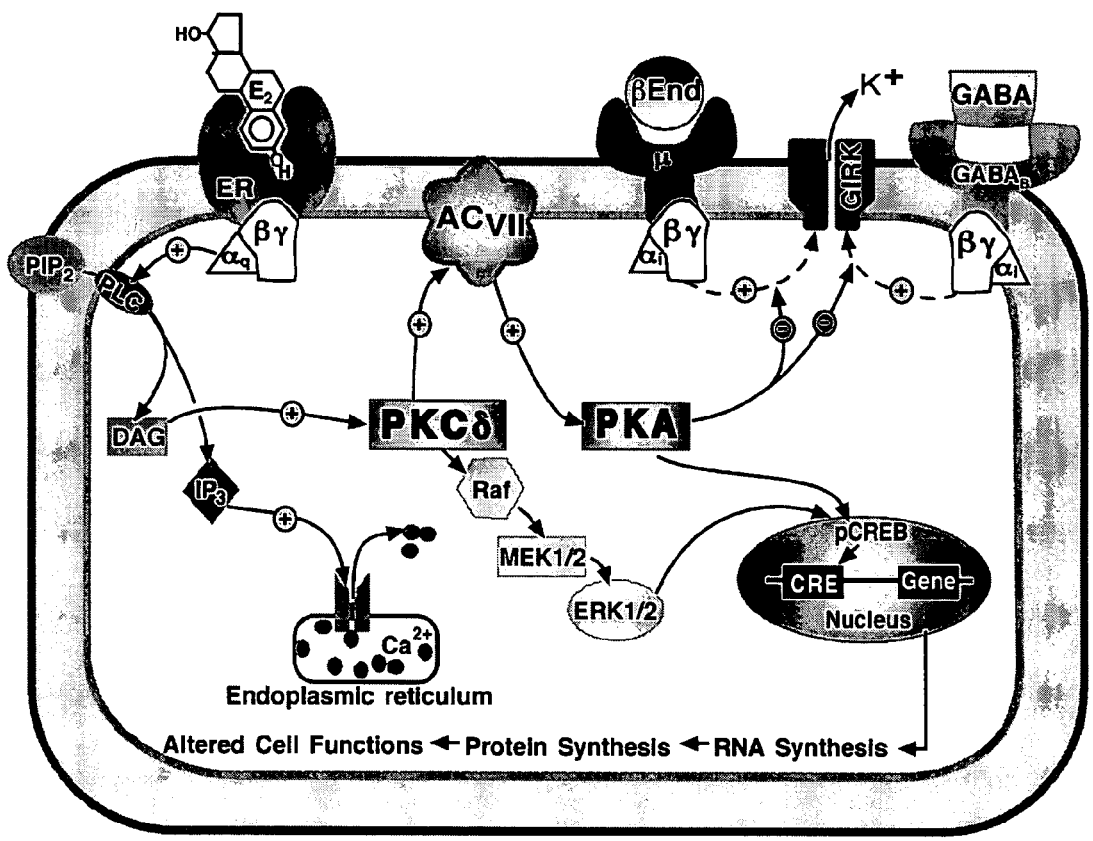

FIG. 15 is a schematic overview showing the rapid versus delayed estrogen receptor mediated modulation of neurotransmitter regulated, G protein-coupled receptors via a membrane-associated estrogen receptor in hypothalamic neurons.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

The specification includes the following acronyms and abbreviations:

BAPTA: 1,2-bis-(o-aminophenoxyethane)-N,N,N',N'-tetraacetic acid

CTX: cholera toxin
DAG: diacylglycerol
DCM: dichloromethane
dd$H_2$O: deionized distilled water
DMF: N,N-dimethylformamide
EGTA: ethylene glycol tetraacetic acid
EtOAc: ethyl acetate
ERK: extracellular-signal related kinase
GIRK: G protein-coupled, inwardly-rectifying $K^+$ channel
Hex: hexanes
MAPK or MAP kinase: mitogen activated protein kinase
PLC: phospholipase C
PKA: protein kinase A
PKC: protein kinase C
POMC: proopiomelanocortin
SERM: selective estrogen receptor modulator
TTX: tetrodotoxin Ranges can be expressed herein as from "about" one particular value, and/or to "about" another particular value. When such a range is expressed, another embodiment includes from the one particular value and/or to the other particular value. Similarly, when values are expressed as approximations, by use of the qualifier "about," it will be understood that the particular value forms another embodiment. It will be further understood that the endpoints of each of the ranges are significant both in relation to the other endpoint, and independently of the other endpoint.

The disclosed compounds include chiral compounds, such as those that contain an asymmetrically tetrasubstituted carbon atom. Such compounds can be isolated in racemic or in optically active forms. It is known to those of ordinary skill in the art how to synthesize compounds in optically active form. It also is well known how to prepare optically active compounds by resolution of racemic mixtures of compounds. All chiral, diastereomeric and geometric isomeric forms of the disclosed structures are intended unless specifically indicated otherwise.

In this specification and in the claims which follow, reference will be made to a number of terms which shall be understood to have the following meanings:

"Optional" or "optionally" means that the subsequently described event or circumstance can but need not occur, and that the description includes instances wherein said event or circumstance occurs and instances wherein it does not.

Variables, such as R, G, M, Q, X, Y and Z, used throughout the disclosure are the same variables as previously defined unless stated to the contrary.

The term "estrogen receptor agonist" refers to a compound that acts at an estrogen receptor and has at least some of the same biological effects as 17β-estradiol. Compounds that act at an estrogen receptor to block the effects of 17β-estradiol are called "estrogen receptor antagonists." Typically, the compounds disclosed herein are partial agonists or antagonists, which means that they mimic or block some of the effects of 17β-estradiol, but not others. In some cases the compounds exhibit mixed agonist/antagonist activity, wherein the compounds act as an estrogen receptor agonist in certain tissues, but act as an estrogen receptor antagonist in other tissues. Examples of such compounds disclosed herein exhibit partial agonist activity by binding selectively to one estrogen receptor with higher affinity than to other estrogen receptors. Compounds exhibiting such selectivity are termed "selective estrogen receptor modulators" or "SERMs."

"Hormone replacement therapy" refers to treatment given in response to reduced or insufficient estrogen production in a subject, for example as seen in menopause. Hormone replacement therapy often is undertaken in response to aging, ovarectomy or premature ovarian failure. Hormone replacement therapy is often used to help treat one or more of the secondary effects associated with estrogen insufficiency, such as osteoporosis, heart disease, hot flushes and mood disorders.

"Derivative" refers to a compound or portion of a compound that is derived from or is theoretically derivable from a parent compound.

The term "alkyl group" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkenyl group" refers to a hydrocarbon group of 2 to 24 carbon atoms and structural formula containing at least one carbon-carbon double bond.

The term "alkynyl group" refers to a hydrocarbon group of 2 to 24 carbon atoms and a structural formula containing at least one carbon-carbon triple bond.

The term "halogenated alkyl group" refers to an alkyl group as described above with one or more hydrogen atoms present on these groups substituted with a halogen (F, Cl, Br, I).

The term "cycloalkyl group" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as described above wherein at least one of the carbon atoms of the ring is substituted with a heteroatom such as, but not limited to, nitrogen, oxygen, sulfur, or phosphorous.

The term "ethylene glycol chain" or "oligoethylene glycol chain" refers to a group having a repeating ethylene glycol unit. The ethylene glycol chain can be any length, however typically it includes from 2 to about 100 and more typically from 2 to about 70 ethylene glycol units. Most typically an oligoethylene glycol chain includes from about 2 to about 20 ethylene glycol units.

The term "aliphatic group" includes alkyl, alkenyl, alkynyl, halogenated alkyl and cycloalkyl groups as described above. A "lower aliphatic" group is a branched or unbranched structure having from 1 to 10 carbon atoms.

The term "aryl group" refers to any carbon-based aromatic group including, but not limited to, benzene, naphthalene, etc. The term "aromatic" also includes "heteroaryl group," which refers to an aromatic group that has at least one heteroatom incorporated within the ring of the aromatic group. Examples of such heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "aralkyl" refers to an aryl group having an alkyl group, as described above, attached to the aryl group. An example of an aralkyl group is a benzyl group.

The term "alkyl amino" includes alkyl groups as described above wherein at least one hydrogen atom is replaced with an amino group.

The term "heteroatom" is understood by those of ordinary skill in the art to refer to an atom other than a carbon atom. Examples of heteroatoms include, without limitation, boron, nitrogen, oxygen, phosphorus and sulfur.

The term "hydrocarbon chain" as used herein therefore typically refers to a chain of carbon atoms, typically comprising from 2 to about 22 carbon atoms. The chain can comprise aliphatic and aryl groups and can comprise straight chain, branched chain and/or cyclic groups.

The term "hydroxyl group" is represented by the formula —OH. The term "alkoxy group" is represented by the formula —OR, wherein R can be an alkyl group, optionally substituted with an alkenyl, alkynyl, aryl, aralkyl, cycloalkyl, halogenated alkyl, or heterocycloalkyl group as described above.

The term "hydroxyalkyl group" refers to an alkyl group that has at least one hydrogen atom substituted with a hydroxyl group. The term "alkoxyalkyl group" refers to an alkyl group that has at least one hydrogen atom substituted with an alkoxy group described above. Where applicable, the alkyl portion of a hydroxyalkyl group or an alkoxyalkyl group can have aryl, aralkyl, halogen, hydroxy, alkoxy The term "amine group" is represented by the formula —NRR', wherein R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', wherein R and R' independently can be a hydrogen, alkyl, alkenyl, alkynyl, aryl, aralkyl, cycloalkyl, halogenated alkyl, or heterocycloalkyl group described above.

The term "ester" is represented by the formula —OC(O)R, wherein R can be an alkyl, alkenyl, alkynyl, aryl, aralkyl, cycloalkyl, halogenated alkyl, or heterocycloalkyl group described above.

The term "carbonate group" is represented by the formula —OC(O)OR, wherein R can be an alkyl, alkenyl, alkynyl, aryl, aralkyl, cycloalkyl, halogenated alkyl, or heterocycloalkyl group described above.

The term "carboxylic acid" is represented by the formula —C(O)OH.

The term "aldehyde" is represented by the formula —C(O)H.

The term "keto group" is represented by the formula —C(O)R, wherein R is an alkyl, alkenyl, alkynyl, aryl, aralkyl, cycloalkyl, halogenated alkyl, or heterocycloalkyl group described above.

The term "carbonyl group" is represented by the formula C=O.

"Cationic group" or "cationic moiety" refers to a group that is positively charged or can be positively charged. For example, a cationic group can be an amine that is capable of being protonated at a physiologically relevant pH. A second example of a cationic group is a positively charged quaternary amine.

The disclosed compounds also encompass salts including, if several salt-forming groups are present, mixed salts and/or internal salts. The salts are generally pharmaceutically-acceptable salts that are non-toxic. Examples of salt-forming acidic groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Particular compounds possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 2-phenoxybenzoic acid, 2-acetoxybenzoic acid, embonic acid, nicotinic acid or isonicotinic acid, and in addition, with amino acids, for example with a-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

The term "ether group" is represented by the formula R(O)R', wherein R and R' can be, independently, an alkyl, alkenyl, alkynyl, aryl, aralkyl, cycloalkyl, halogenated alkyl, or heterocycloalkyl group described above.

The term "halide" refers to F, Cl, Br, or I.

The terms "urethane" and carbamate are represented by the formula—OC(O)NRR', wherein R and R' can be, independently, hydrogen, an alkyl, alkenyl, alkynyl, aryl, aralkyl, cycloalkyl, halogenated alkyl, or heterocycloalkyl group described above.

The groups described above can be optionally substituted with one or more substituents. The definition of any substituent or variable at a particular location in a molecule is independent of its definitions elsewhere in that molecule. Examples of suitable substituents include but are not limited to alkyl, alkenyl, alkynyl, aryl, halo, trifluoromethyl, trifluoromethoxy, hydroxy, alkoxy, oxo, alkanoyl, alkanoyloxy, aryloxy, amino, amido, alkanoylamino, aroylamino, aralkanoylamino, substituted alkanoylamino, aroylamino, aralkanoylamino, substituted alkanoylamino, substituted arylamino, substituted aralkanoylamino, thiol, sulfide, thiono, sulfonyl, sulfonamide, nitro, cyano, carboxy, carbamyl, substituted carbamyl and the like.

The term "prodrug" is intended to include any covalently bonded carriers that release an active parent drug of the present invention in vivo when the prodrug is administered to a subject. Since prodrugs are known to enhance the properties of pharmaceuticals, such as, solubility and bioavailability, the compounds disclosed herein can be delivered in prodrug form. Thus, also contemplated are methods of delivering of the presently claimed compounds, methods of delivering prodrugs and compositions containing such prodrugs. Prodrugs of the disclosed compounds typically are prepared by modifying functional groups present in the compound in such a way that the modifications are cleaved, either in routine manipulation or in vivo, to yield the parent compound. Prodrugs include compounds having a hydroxy, amino, or sulfhydryl group functionalized with any group that is cleaved to yield the corresponding hydroxyl, free amino, or free sulfhydryl group, respectively. Examples of prodrugs include, without limitation, compounds having a hydroxy, amino and/or sulfhydryl group acylated with an acetate, formate, and/or benzoate group.

Protected derivatives of the disclosed compound also are contemplated. A variety of suitable for use with the disclosed compounds is disclosed in Greene and Wuts *Protective Groups in Organic Synthesis;* 3rd Ed.; John Wiley & Sons, New York 1999.

It is understood that substituents and substitution patterns of the compound described herein can be selected by one of ordinary skill in the art to provide compounds that are chemically stable and that can be readily synthesized by techniques known in the art and further by the methods set forth in this disclosure. Reference will now be made in detail to the present preferred embodiments.

I. Selection of Preferred Compounds

Preferred compounds for modulating an estrogen receptor typically are selected for their potency and selectivity in agonizing or antagonizing one or more estrogen receptors. Typically the disclosed compounds selectively bind to a membrane associated estrogen receptor and bind to the nuclear estrogen receptors (ER)α and (ER)β with lower affinity, if at all. As described in the Methods and Examples section below, and as is generally known, efficacy of particular compounds against a target estrogen receptor can be determined in vitro, and the disclosed in vitro methods can be used to screen and identify novel SERMs. Moreover, particular compounds are provided for treating or protecting against various conditions and disorders, including conditions that are associated with menopause or other conditions characterized by estrogen insufficiency, such as those associated with ovarectomy, ovarian failure or menopause. Examples of such conditions include, without limitation, hot flushes, cognitive decline, osteoporosis, depression, ischemic brain damage and atherosclerosis.

The ability of the disclosed compounds to inhibit or ameliorate hot flushes can be determined, for example, in a standard assay that measures the ability of an agent to blunt the increase in tail skin temperature that occurs when morphine-addicted rats undergo acute withdrawal from morphine using naloxone. See, Merchenthaler, et al. The effect of estrogens and antiestrogens in a rat model for hot flush. *Maturitas* 1998, 30, 307–316, which is incorporated herein by reference. See also, Berendsen et al. Effect of tibolone and raloxifene on the tail temperature of oestrogen-deficient rats. *Eur. J. Pharmacol.* 2001, 419, 47–54; and Pan et al. A comparison of oral micronized estradiol with soy phytoestrogen effects on tail skin temperatures of ovariectomized rats. *Menopause* 2001, 8, 171–174. Both the Berendsen and Pan publications are incorporated herein by reference.

Certain disclosed compounds are useful for the treatment of multiple sclerosis. Preferred compounds for treating or suppressing the symptoms of multiple sclerosis can be selected by using the experimental autoimmune encephalomyelitis mouse model described by Polanczyk et al. *Am. J. Pathol.* 2003, 163, 1599–1605. The Polanczyk publication is incorporated herein by reference.

Disclosed compounds that are useful for treating eating disorders, such as anorexia nervosa and/or bulimia nervosa can be identified using a simple feeding assay as is known to those of ordinary skill in the art.

The effect of the disclosed compounds on learning and memory can be assessed using the Morris water maze and object recognition assays according to the protocols described by Stackman et al. *J. Neuroscience* 2002, 22, 10163–10171. The Stackman et al. publication is incorporated herein by reference.

The neuroprotective activity of the disclosed compounds also can be evaluated, for example, in a standard in vitro pharmacological assay using glutamate challenge. See, Zaulyanov, et al. *Cellular & Molecular Neurobiology* 1999, 19: 705–718; and Prokai, et al. *Journal of Medicinal Chemistry* 2001, 44, 110–114. Both the Zaulyanov et al. and Prokai et al. publications are incorporated herein by reference.

The disclosed compounds also can be evaluated for their ability to protect neurons from damage associated with global cerebral ischemia. Compounds can be evaluated for their ability to reduce such damage using the cardiac arrest and cardiopulmonary resuscitation assay described by Vogel et al. Anesthesiology 2003, 99, 112–121. In one aspect, the compounds can reduce the damage to neurons even when administered after resuscitation. The Vogel et al. publication is incorporated herein by reference.

Neuroprotection also can be evaluated using a middle cerebral artery occlusion procedure in mice according to the protocol described by Dubal et al. in *Proc. Natl. Acad. Sci. U.S.A.* 2001, 98, 1952–1957; and in *J. Neurosci.* 1999, 6385–6393. Additional assays for evaluating the disclosed compounds in different models of disorders characterized by estrogen insufficiency are described in the Methods and Examples section below.

Use of the compounds is not necessarily limited to conditions involving estrogen insufficiency. Techniques and assays for characterizing the efficacy of therapeutics for treating or preventing such conditions and disorders are well known and are described, for example, by Malamas et al. and Mewshaw et al. in U.S. patent publication Nos. 2003/0171412 A1 and 2003/0181519 A1, respectively. Both the Malamas et al. and Mewshaw et al. publications are incorporated herein by reference.

II. Pharmaceutical Compositions

Another aspect of the disclosure includes pharmaceutical compositions prepared for administration to a subject and which include a therapeutically effective amount of one or more of the currently disclosed compounds. The therapeutically effective amount of a disclosed compound will depend on the route of administration, the type of mammal that is the subject and the physical characteristics of the subject being treated. Specific factors that can be taken into account include disease severity and stage, weight, diet and concurrent medications. The relationship of these factors to determining a therapeutically effective amount of the disclosed compounds is understood by those of ordinary skill in the art.

The therapeutically effective amount of the compound or compounds administered can vary depending upon the desired effects and the factors noted above. Typically, dosages will be between about 0.01 mg/kg and 100 mg/kg of the subject's body weight, and more typically between about 0.01 mg/kg and 10 mg/kg of the subject's body weight. In one aspect the therapeutically effective amount can be selected to achieve an in vivo concentration of the therapeutic agent in a target tissue of a subject of about the concentration found to be effective in vitro.

In one embodiment, the disclosed SERM is used in combination with additional compounds disclosed herein and/or other therapeutic agents, such as other SERMs, anti-cancer agents or anti-proliferative agents. For example the disclosed compounds may be used with chemotherapeutic agents, such as tamoxifen, taxol, epothilones, methotrexate, and the like. In one aspect, a disclosed SERM is used in combination with a steroid hormone, such as an estrogen, including 17β-estradiol, a progesterone or the like. The estrogen or progesterone can be a naturally occurring or synthetic estrogen or progesterone. When different therapeutic agents are used in combination, the therapeutic agents can be administered together or separately. The therapeutic agents can be administered alone, but more typically are administered with a pharmaceutical carrier selected on the basis of the chosen route of administration and standard pharmaceutical practice.

Any of the SERMs described herein can be combined with a pharmaceutically acceptable carrier to form a pharmaceutical composition. Pharmaceutical carriers are known to those skilled in the art. These most typically would be standard carriers for administration of compositions to humans, including solutions such as sterile water, saline, and buffered solutions at physiological pH. The compositions could also be administered intramuscularly, subcutaneously, or in an aerosol form. Other compounds will be administered according to standard procedures used by those skilled in the art.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, sustained release of the pharmaceutical preparation that comprises an effective amount of a disclosed SERM can be beneficial. Slow-release formulations are known to those of ordinary skill in the art. By way of example, polymers such as bis(p-carboxyphenoxy)propane-sebacic-acid or lecithin suspensions can be used to provide sustained release.

It is specifically contemplated in some embodiments that SERM delivery is via an injected and/or implanted drug depot, for instance comprising multi-vesicular liposomes such as in DepoFoam (SkyePharma, Inc, San Diego, Calif.) (see, for instance, Chamberlain et al. *Arch. Neuro.* 1993, 50, 261–264; Katri et al. *J. Pharm. Sci.* 1998, 87, 1341–1346; Ye et al., *J. Control Release* 2000, 64, 155–166; and Howell, *Cancer J.* 2001, 7, 219–227).

III. Methods for Using the Disclosed Compounds

The disclosed compounds can be used to selectively modulate an estrogen receptor in a subject and thus are useful for treating a variety of disorders, including those characterized by an estrogen deficiency. Moreover, because certain disclosed compounds exhibit selectivity for one or more estrogen receptors, the compounds can be used to treat conditions including but not limited to those described as autonomic dysfunctions, cognitive decline, motor dysfunctions, mood disorders, eating disorders and cardiovascular disorders, as well as different types of disorders. Generally, the compounds are useful for hormone replacement therapy without inducing the same incidence of serious side effects associated with the steroidal hormones (such as estrogen or synthetic estrogens) used in current hormone replacement therapies. The disclosed compounds also avoid side effects such as hot flushes encountered in treatment with currently known SERMs, such as tamoxifen or raloxifene. More specifically, the disclosed compounds can be used to treat disorders including, without limitation, ischemia-induced neuronal death, head trauma, Alzheimer's disease, disorders of temperature regulation, such as hot flushes, sleep cycle disruptions, Parkinson's disease, tardive diskinesia, depression, schizophrenia, anorexia nervosa, bulimia nervosa, cardiovascular disease, atherosclerosis, long QTL syndromes, such as Romano-Ward or Torsades de Pointes syndromes, osteoporosis, rheumatoid arthritis, osteoarthritis, bone fractures and multiple sclerosis. In one embodiment particular compounds can be used to promote vasodilation by modulating fluid balance, such as by blocking epithelial transport of sodium or chloride. Without limitation to theory, the compounds appear to function by activating maxi-K channels. See, Valverde et al. *Science* 1999, 285, 1929–1931.

In another embodiment, the disclosed compounds can be used to treat autoimmune diseases, particularly autoimmune diseases that occur more frequently in women than in men. Examples of such diseases include, without limitation, multiple sclerosis, rheumatoid arthritis, Grave's disease, systemic lupus erythematosus and myasthenia gravis. In another embodiment the disclosed compounds function to maintain or enhance immune competency in a subject. Moreover, the disclosed compounds exert prophylactic effects against certain types of injuries. For example, the compounds can be used as neuroprotectants. Indeed, compounds that agonize the membrane-associated estrogen receptor identified herein act as neuroprotectants in response to ischemic stroke and inhibit reperfusion injury.

Moreover, because of the ability of the disclosed compounds to selectively modulate one or more specific types of estrogen receptor, they can be used to identify the contribution of different estrogen receptors that mediate different physiological effects. The disclosed compounds also can be used to bind to and identify the particular class of membrane bound receptors at which these agents act. Indeed, a working embodiment of the disclosed selective estrogen receptor modulators had a ten-fold higher potency than 17β-estradiol for the membrane-associated receptor and a million-fold lower affinity than 17β-estradiol for the nuclear estrogen receptors (ER)α and (ER)β.

Another application of the disclosed compounds is affinity chromatography. Because examples of the presently disclosed compounds bind to a novel, membrane-associated estrogen receptor, the compounds can be used to purify the receptor, or remove the receptor from a sample. To use the compounds, they typically are attached to a solid support as is known to those of ordinary skill in the art. The compounds can be attached directly or via a linker molecule. Exemplary affinity chromatography techniques suitable for use with the disclosed compounds are disclosed in Current Protocols in Protein Science, John Wiley & Sons (J. E. Coligan et al., Eds.).

IV. Synthesis

The compounds disclosed herein, as well as analogs of such compounds that will be readily apparent to those of ordinary skill in the art of medicinal chemistry upon consideration of this disclosure, can be prepared in a number ways using techniques well known to those of ordinary skill in the art. Exemplary methods for making particular compounds are described below. It is understood by those of ordinary skill in the art of organic synthesis that these methods are generalizable to the synthesis of compounds not explicitly described below upon consideration of the functionality of the molecule in view of the reagents and reactions disclosed. In view of the disclosed conditions, a person of ordinary skill in the art will recognize alternate methods for preparing analogous compounds that may have functional groups that are incompatible with the specific conditions disclosed herein.

Depending upon the functional groups present in a given transformation, protecting groups for various groups may be preferred for masking the group during the transformation. Suitable protecting groups for various functionalities are described in Greene and Wuts *Protective Groups in Organic Synthesis;* 3rd Ed.; John Wiley & Sons, New York (1999).

One embodiment of a method for synthesizing the disclosed compounds is illustrated in Scheme 3, below. With reference to Scheme 3, the method includes providing a compound 2 and converting compound 2 to compound 4. Compound 2 was prepared according to the protocol reported by Weatherman et al. *Chemistry & Biology* 2001, 8, 427–436. In working examples compound 2 was subjected to lithium-halogen exchange conditions, followed by reaction with allyl chloroformate to give compound 4. Compound 6 was prepared via palladium-catalyzed cleavage of the allyl ester group. In working examples, catalytic $Pd(PPh_3)_4$ was used along with $PhSiH_3$ to produce compound 6. Compound 6 is a versatile intermediate that can be used to prepare a variety of N-substituted acrylamide derivatives. For example, any primary or secondary amine can be incorporated via an amide bond forming reaction with compound 6. The method illustrated in Scheme 3 produces both the E and Z isomers, compounds 8 and 9, respectively.

Scheme 3

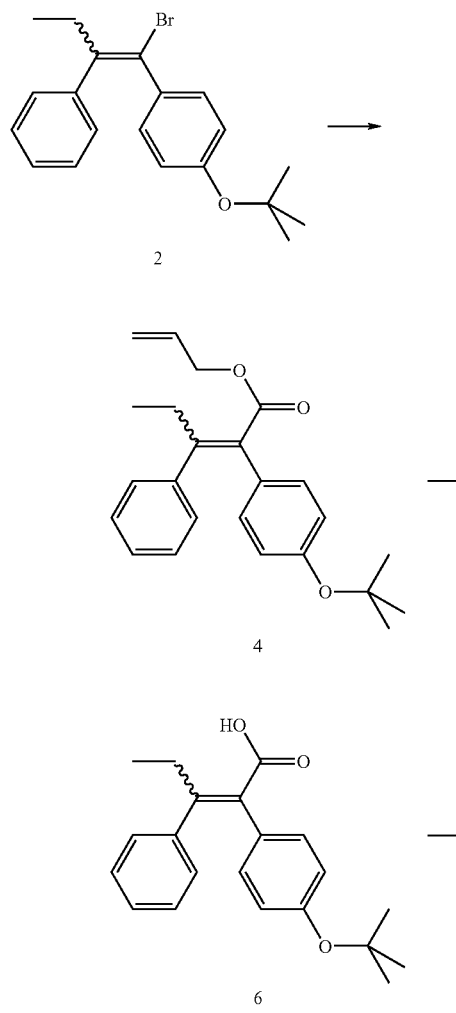

Scheme 4

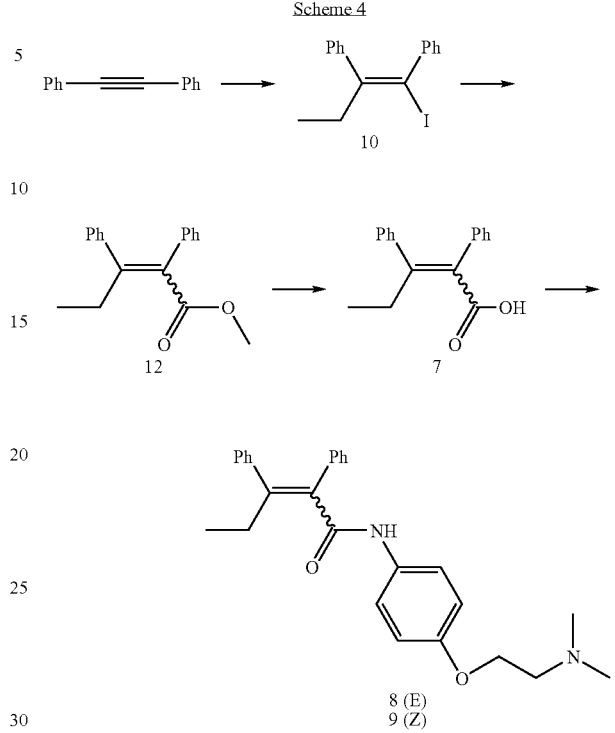

Disubstituted acrylamide derivatives can be prepared according to the method illustrated in Scheme 5. With reference to Scheme 5, bis-allylation of 18 yields 20. Aldol reaction of 20 with benzaldehyde yields 22, which undergoes elimination to yield 24, as a mixture of E and Z isomers. Cleavage of the allyl protecting groups yields 26, followed by amide bond formation to form E and Z isomers, 28 and 30, respectively.

Scheme 5

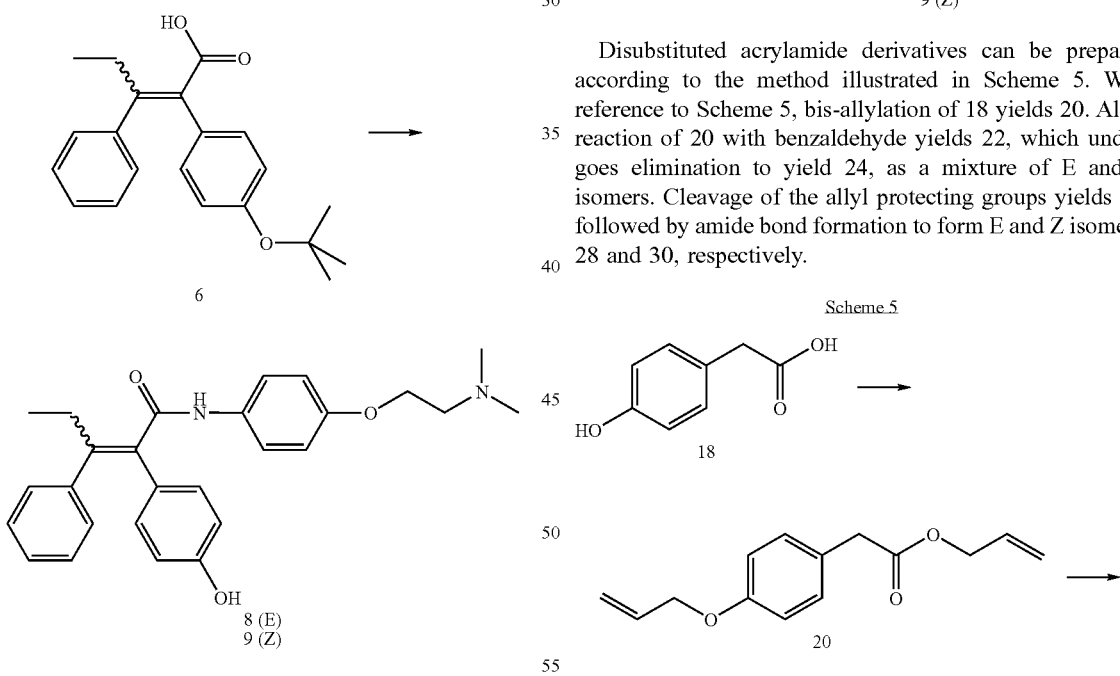

Additional SERMs can be prepared according to Scheme 4. With reference to Scheme 4, compound 10 can be prepared from diphenylacetylene. A variety of alkyl groups (in addition to ethyl) can be introduced in this step by various techniques. The iodo group introduced in compound 10 can be used to introduce a carboxy group, such as the carboxy methyl ester 12, which is readily converted to the corresponding carboxylic acid 7. Carboxylic acid 7 can be reacted with a variety of primary and secondary amines to yield the corresponding amides, such as 8 and the corresponding Z isomer 9.

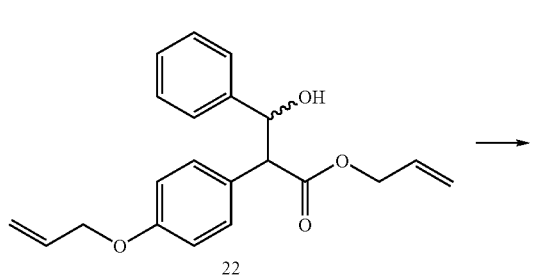

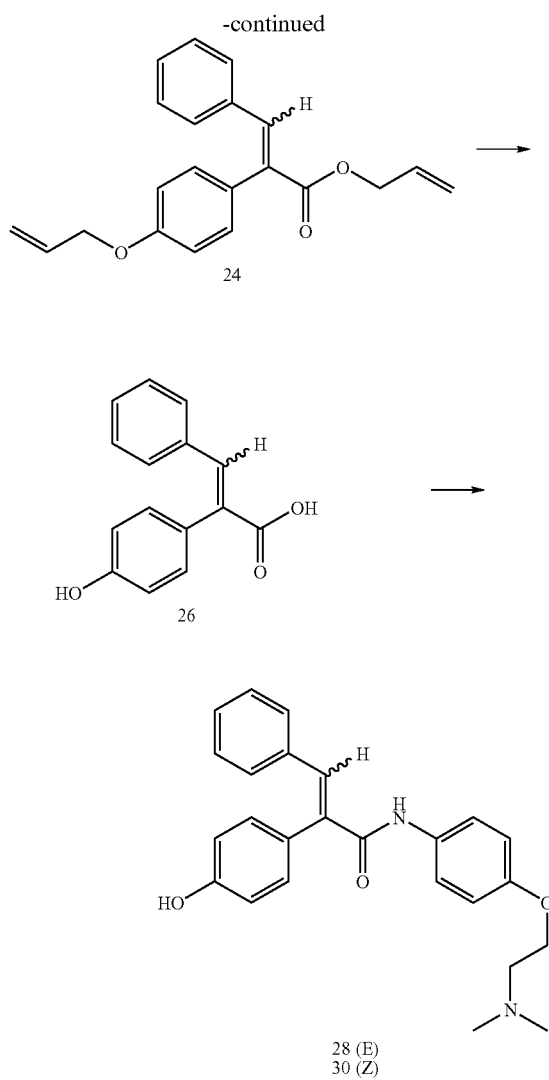

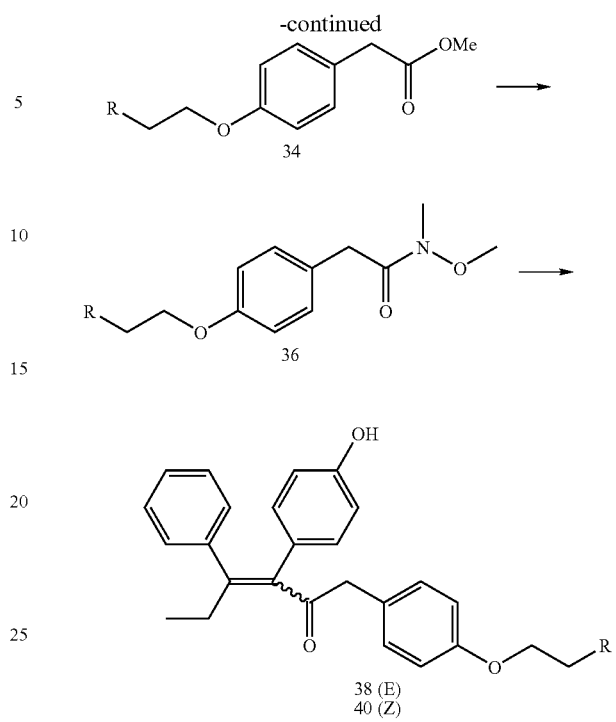

Scheme 6 depicts an embodiment of a method for synthesizing vinyl ketone derived SERMs. With reference to Scheme 6, alkylation of compound 32 is a versatile reaction that can be used to introduce a variety of groups. For example, R can include, with limitation, a hydroxy group, a protected hydroxy group, a carboxy group, a protected carboxy group, an amine or a protected amino group. In working examples R was a dimethyl amino group or a piperidino group. Intermediate 34 is reacted with the lithium anion of compound prepared from compound 2 (Scheme 3), to yield, after deprotection, E and Z isomers 38 and 40, respectively.

Scheme 6

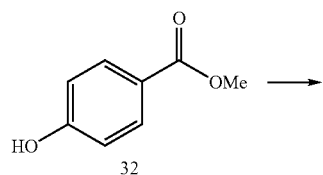

V. METHODS AND EXAMPLES

The foregoing disclosure is further explained by the following non-limiting examples.

Example 1

This example describes the synthesis of 2-(4-tert-butoxyphenyl)-3-phenylpent-2-enoic acid allyl ester, 4.

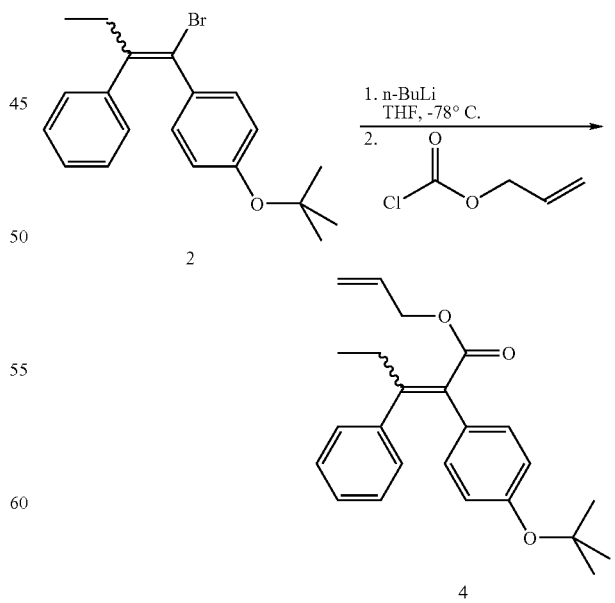

n-Butyl lithium (6.68 mL, 16.7 mmol; 2.5 M) was added dropwise to a solution of vinyl bromide 2 (3.00 g, 8.35 mmol) in anhydrous THF (75 mL) that was cooled to −78° C. After stirring for 15 min, allyl chloroformate (4.43 mL, 41.8 mmol) was added neat and dropwise. This was allowed to stir from −78° C. to room temperature over 4 h. Saturated sodium bicarbonate was added, extracted with ethyl acetate, dried over anhydrous magnesium sulfate, filtered and concentrated under reduced pressure to give a yellow oil. The crude product was purified by column chromatography (5% EtOAc/Hex) to give 4 as a light yellow oil (1.80 g, 4.94 mmol) in 59% yield. $R_f$ of E-isomer=0.20 and of Z-isomer=0.14 (5% EtOAc/Hex). $^1$H NMR (CDCl$_3$): δ E-isomer: 1.01 (t, 3H); 1.25 (s, 9H); 2.68 (q, 2H); 4.72 (d, 2H); 5.25 (m, 2H); 5.94 (m, 1H); 6.69 (d, 2H); 6.87 (d, 2H); 7.00 (m, 2H); 7.11 (m, 3H). δ Z-isomer: 0.82 (t, 3H); 1.35 (s, 9H); 2.37 (q, 2H); 4.27 (d, 2H); 4.96 (m, 2H); 5.43 (m, 1H); 7.00 (d, 2H); 7.26 (m, 7H). HRMS (EI) mass calculated for C$_{24}$H$_{28}$O$_3$: 364.2038. found: 364.2038. $^{13}$C NMR (CDCl$_3$): δ Z-isomer: 12.71, 14.10, 23.32, 25.66, 27.98, 28.87, 38.98, 65.12, 74.35, 78.57, 117.82, 123.73, 127.36, 127.64, 128.06, 129.60, 131.74, 131.80, 131.90, 141.17, 149.25, 154.93, 169.18.

Example 2

This example describes the synthesis of 2-(4-tert-butoxyphenyl)-3-phenylpent-2-enoic acid, 6.

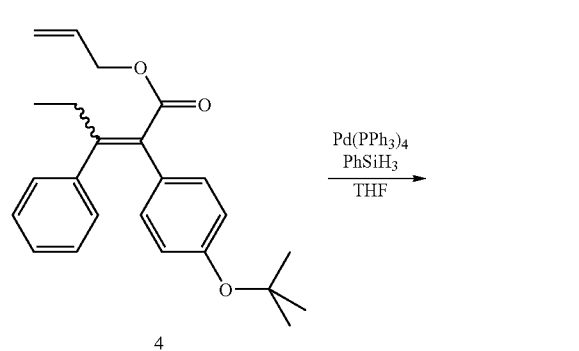

To a solution of compound 4 (0.16 g, 0.439 mmol) in 10 mL of anhydrous dichloromethane, was added PhSiH$_3$ (0.11 mL, 0.878 mmol) followed by Pd(PPh$_3$)$_4$ (10 mg, 8.78 μmol). The reaction was stirred at room temperature under argon for 30 min. It was then quenched with ddH$_2$O, the pH was decreased to 2 with 1M HCl, extracted with dichloromethane, dried over magnesium sulfate, filtered and concentrated under reduced pressure. The crude yellow oil was purified by column chromatography (35% EtOAc/Hex) to give a white solid (0.14 g, 0.432 mmol) in 99% yield.

$R_f$ of E-isomer=0.33 and of Z-isomer=0.49 (10% MeOH/CHCl$_3$). $^1$H NMR (CDCl$_3$): δ E-isomer: 1.02 (t, 3H); 2.80 (q, 2H); 6.70 (d, 2H); 6.90 (d, 2H); 6.98 (m, 3H); 7.10 (m, 2H). δ Z-isomer: 0.84 (t, 3H); 2.35 (q, 2H); 7.00 (d, 2H); 7.22 (d, 2H); 7.27 (m, 7H). HRMS (EI) mass calculated for C$_{21}$H$_{24}$O$_3$: 324.1725. found: 324.1570.

Example 3

This example describes the synthesis of 2-(4-tert-butoxyphenyl)-3-phenylpent-2-enoic acid [4-(2-dimethylamino ethoxy) phenylamide, 7.

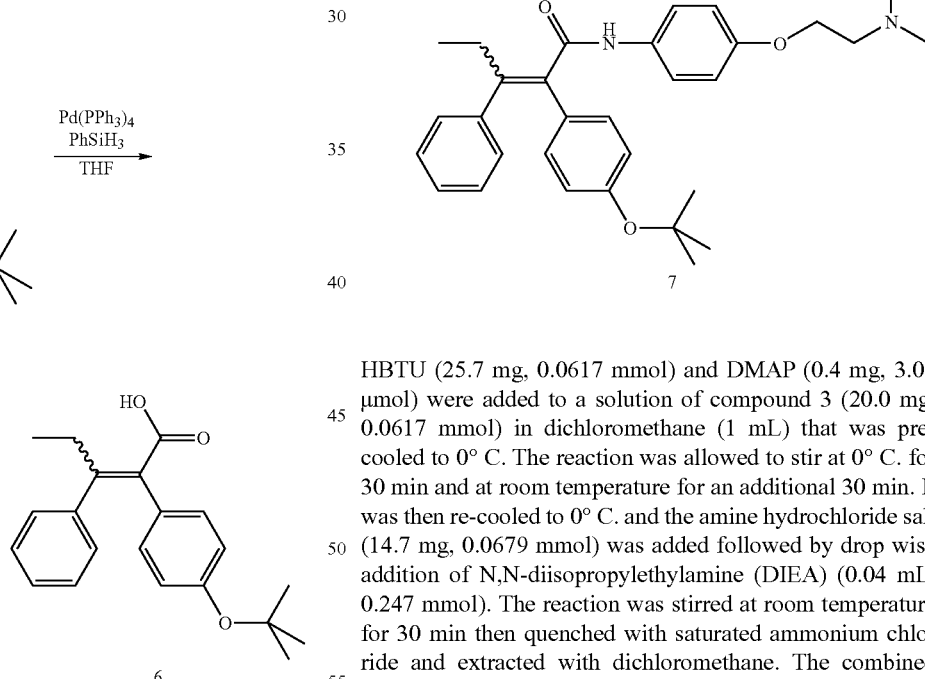

HBTU (25.7 mg, 0.0617 mmol) and DMAP (0.4 mg, 3.09 μmol) were added to a solution of compound 3 (20.0 mg, 0.0617 mmol) in dichloromethane (1 mL) that was pre-cooled to 0° C. The reaction was allowed to stir at 0° C. for 30 min and at room temperature for an additional 30 min. It was then re-cooled to 0° C. and the amine hydrochloride salt (14.7 mg, 0.0679 mmol) was added followed by drop wise addition of N,N-diisopropylethylamine (DIEA) (0.04 mL, 0.247 mmol). The reaction was stirred at room temperature for 30 min then quenched with saturated ammonium chloride and extracted with dichloromethane. The combined organic layers were washed 1× with saturated sodium bicarbonate, dried over magnesium sulfate, filtered and concentrated under reduced pressure. The crude product was purified by column chromatography (10% MeOH/CHCl$_3$) to give a white foam (25.4 mg, 0.519 mmol) in 84% yield. $R_f$ of E-isomer=0.15 and of Z-isomer=0.33 (10% MeOH/CHCl$_3$). $^1$H NMR (CDCl$_3$): δ E-isomer: 1.02 (t, 3H); 1.25 (s,9H); 2.35 (s, 6H); 2.82 (t, 2H); 2.79 (q, 2H); 4.02 (t, 2H); 6.72 (d, 2H); 6.85 (d, 2H); 6.92 (d, 2H); 7.01 (m, 3H); 7.10 (m, 3H); 7.38 (d, 2H). δ Z-isomer: 0.91 (t, 3H); 1.38 (s, 9H); 2.40 (s,6H); 2.45 (q, 2H); 2.82 (t, 2H); 3.96 (t, 2H); 6.63 (d, 2H); 6.82 (m, 3H); 7.01 (d, 2H); 7.30 (m, 6H).

Example 4

This example describes the synthesis of (E,Z)-2-(4-hydroxyphenyl)-3-phenylpent-2-enoic acid [4-(2-dimethylaminoethoxy)-phenyl]amide (8 and 9).

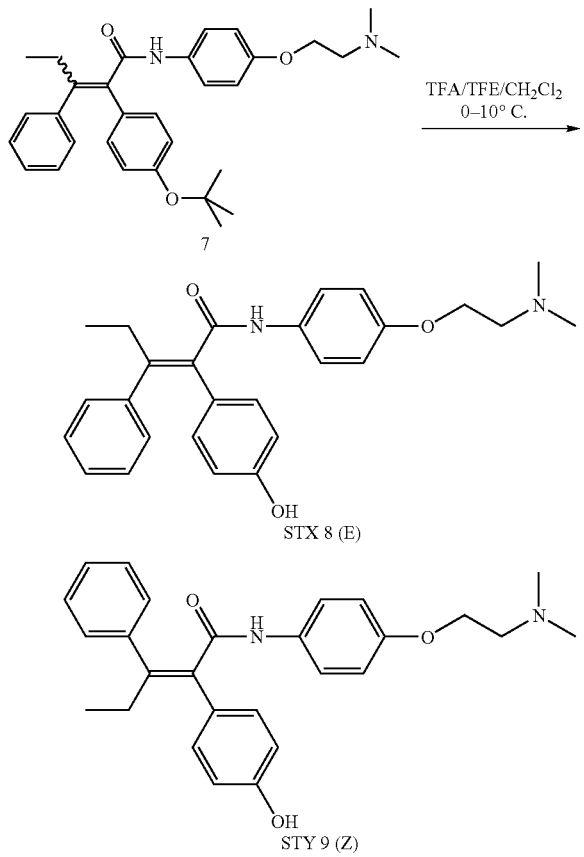

Compound 7 (25.3 mg, 0.0514 mmol) was dissolved in anhydrous dichloromethane (0.47 mL) and cooled to 0° C. 2,2,2-Trifluoroethanol (0.37 mL) and trifluoroacetic acid (0.74 mL) were added and the reaction mixture was stirred from 0° C. to 10° C. over 1.5 h. After this time, the solution was poured into 1M HCl, extracted with $CH_2Cl_2$, dried over magnesium sulfate, filtered and the solvent was removed under reduced pressure. The crude product was purified by column chromatography (15% MeOH/$CHCl_3$) to yield a white foam (21.5 mg, 0.499 mmol) in 97% yield. $R_f$ of E-isomer 8=0.18 and of Z-isomer 9=0.22 (15% MeOH/$CHCl_3$). $^1$H NMR (MeOD): δ E-isomer: 0.90 (t, 3H); 2.49 (s,6H); 2.58 (q, 2H); 2.95 (t, 2H); 4.10 (t, 2H); 6.43 (d, 2H); 6.86 (m,4H); 7.10 (m, 5H); 7.47 (d, 2H). $^{13}$C NMR (MeOD): 13.20, 30.40, 45.18, 58.66, 65.68, 115.69, 115.82, 123.41, 127.93, 129.11, 130.42, 171.77, 133.29, 136.06, 141.48, 143.52, 156.74, 157.57, 171.96. $^1$H NMR (MeOD): δ Z-isomer: 0.90 (t, 3H); 2.49 (s,6H); 2.50 (q, 2H); 2.92 (t, 2H); 4.05 (t, 2H); 6.75 (d, 2H); 6.83 (d,2H); 7.01 (d, 2H); 7.27 (m, 6H); 7.39 (d, 2H). $^{13}$C NMR (MeOD): 13.21, 28.22, 45.35, 58.75, 65.78, 117.2, 116.5, 123.8, 128.5, 129.2, 129.5, 131.2, 132.5, 137.2, 142.2, 147.8, 156.5, 158.4, 171.8. HRMS (EI) mass calculated for $C_{27}H_{30}N_2O_3$: 430.2256. found: 430.2263.

Example 5

This example describes the synthesis of 1-iodo-1,2-diphenylbut-1-ene, 10.

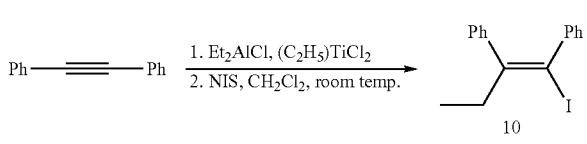

Diethyl aluminum chloride (9.78 g, 0.0393 mol) was added to a solution of bis(cyclopentadienyl)titanium dichloride (21.8 mL, 0.0393 mol; 1.8M) in anhydrous dichloromethane (200 mL) and the mixture was allowed to stir at room temperature for 10 min under an atmosphere of argon. Diphenylacetylene (5.0 g, 0.0281 mol) was added slowly and stirred for 5 h. The reaction mixture was cooled to −78° C. and diluted with 70 mL of dichloromethane. N-Iodosuccinimide (NIS) (14.5 g, 0.0645 mol) was added slowly so that the temperature remained at −78° C., after addition, the reaction was stirred at room temperature overnight. The next day, it was poured into hexanes (100 mL), 5% $Na_2SO_3$ in 3N NaOH (200 mL) was added and filtered. After filtration, the two layers were separated, the organic layer was washed with 5% $Na_2SO_3$ (200 mL), followed by 3N HCl (200 mL) and saturated $NaHCO_3$ (100 mL). The organic layer was dried over magnesium sulfate, filtered and concentrated under reduced pressure. The crude product was purified by column chromatography in hexanes to give 10 as a light brown oil (7.15 g, 0.0214 mol) in 76% yield. $^1$H NMR ($CDCl_3$) δ: 1.03 (t, 3H); 2.82 (q, 2H); 7.05 (m, 9H). $^{13}$C NMR ($CDCl_3$): δ 11.77, 38.58, 98.89, 126.58, 126.92, 127.50, 127.78, 128.22, 128.32, 129.05, 129.88, 131.59, 139.60, 144.51, 150.24.

Example 6

This example describes the synthesis of 2,3-Diphenylpent-2-enoic acid methyl ester, 12.

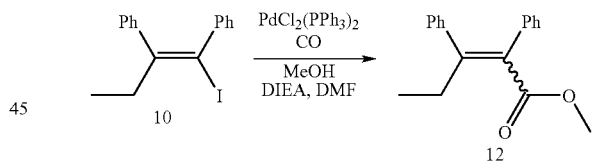

Methanol (5 mL), DIEA (0.17 mL, 0.987 mmol) and $PdCl_2(PPh_3)_2$ (107 mg, 0.153 mmol) were added to vinyl iodide 10 (300 mg, 0.898 mmol) that was dissolved in anhydrous DMF. Carbon monoxide was bubbled for 5 min and the reaction mixture was allowed to stir at 80° C. under atmosphere of CO for 3 days. The cooled reaction mixture was diluted with ethyl acetate, washed with dd$H_2O$, the layers were separated, and the organic layer was dried over magnesium sulfate, and filtered and concentrated under reduced pressure. The crude product was purified by column chromatography in chloroform to give the product (198 mg, 0.743 mmol) in 83% yield. $R_f$ of E-isomer=0.47 and of Z-isomer=0.53 ($CHCl_3$). $^1$H NMR ($CDCl_3$) δ: 0.86 (t, 2H, Z-isomer); 1.01 (t, 3H, E-isomer); 2.38 (q, 1H, Z-isomer); 2.69 (q, 2H, E-isomer); 3.38 (s, 1H, Z-isomer); 3.78 (s, 3H, E-isomer); 7.07 (m, 7H); 7.36 (m, 4H). $^{13}$C NMR ($CDCl_3$) δ: 12.72, 12.80, 27.99, 29.96, 51.57, 51.94, 126.75, 126.97, 127.45, 127.57, 127.73, 127.84, 128.08, 128.37, 128.93, 128.99, 129.75, 130.19, 132.20, 137.05, 140.07, 149.91.

Example 7

This example describes the synthesis of 2,3-diphenylpent-2-enoic acid, 14.

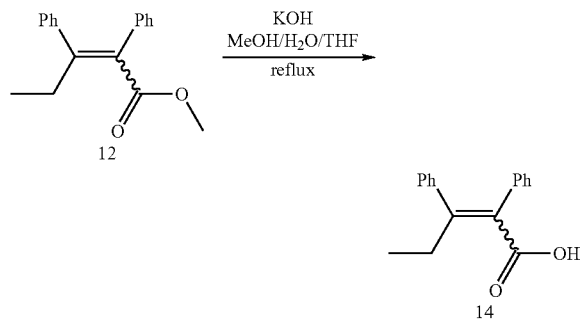

To a solution of compound 12 (50 mg, 0.188 mmol) in methanol (4 mL) and THF (9 mL), a 0.2M solution of KOH (9.4 mL, 1.88 mmol) was added drop wise. The reaction was then heated to reflux for 2 days. Next day it was poured into 10 mL of 1N HCl, stirred for 10 min, extracted with CHCl$_3$, dried organic layer over magnesium sulfate, filtered and concentrated under reduced pressure. The crude product was purified by column chromatography (5% MeOH/CHCl$_3$) to yield a white solid (32 mg, 0.127 mmol) in 68% yield. R$_f$ of E-isomer=0.33 and of Z-isomer=0.47 (5% MeOH/CHCl$_3$). $^1$H NMR (CDCl$_3$) δ: E-isomer 1.02 (t, 3H); 2.80 (q, 2H); 7.02 (m, 4H); 7.11 (m, 6H). Z-isomer 0.84 (t, 3H); 2.33 (q, 2H); 7.04 (d, 2H); 7.33 (m, 8H).

Example 8

This example describes the synthesis of E and Z 2,3-Diphenylpent-2-enoic acid [4-(2-dimethylaminoethoxy)-phenyl]amide, 16 and 17.

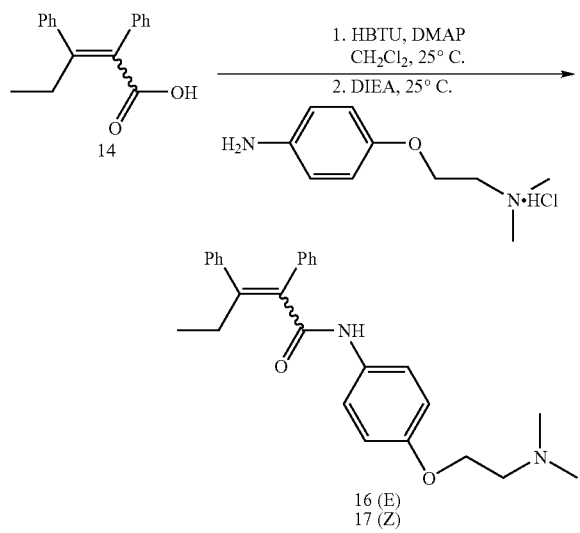

Compounds 16 and 17 were synthesized as described for compounds 8 and 9 (Example 4) using compound 14 (as a mixture of E and Z isomers) (29 mg, 0.115 mmol), HBTU (48 mg, 0.126 mmol), DMAP (0.7 mg, 5.7 µmol), amine hydrochloride (27 mg, 0.126 mmol) and DIEA (0.08 mL, 0.459 mmol) to give the desired product 17 (19 mg, 0.0488 mmol) in 32% yield and 16 (29 mg, 0.070 mmol) in 60% yield. R$_f$ of E-isomer=0.15 16 and of Z-isomer 17=0.10 (5% MeOH/CHCl$_3$). E-isomer $^1$H NMR (CDCl$_3$) δ: 1.05 (t, 3H); 2.32 (s, 6H); 2.70 (t, 2H); 2.82 (q, 2H); 4.05 (t, 2H); 6.85 (d, 2H); 7.10 (m, 8H); 7.42 (m, 4H). $^{13}$C NMR (CDCl$_3$) δ: 13.09, 18.01, 29.69, 45.77, 58.17, 66.16, 114.86, 121.59, 126.93, 127.14, 127.92, 128.17, 128.99, 129.97, 131.07, 137.23, 140.50, 148.77, 155.66, 167.72. E-isomer $^1$H NMR (CDCl$_3$) δ: 0.90 (t, 3H); 2.39 (s, 6H); 2.41 (q, 2H); 2.81 (t, 2H); 4.00 (t, 2H); 6.62 (d, 2H); 6.82 (d, 2H); 7.39 (m, 10H).

Example 9

This example describes the synthesis of (4-allyloxyphenyl) acetic acid allyl ester, 20.

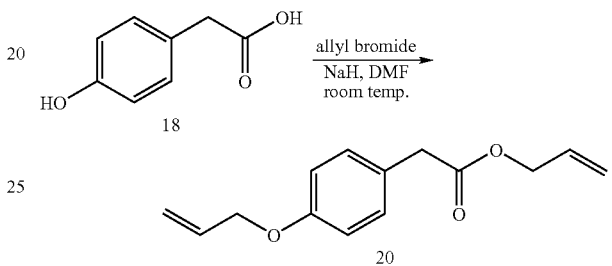

Sodium hydride (1.90 g, 0.0789 mmol) was suspended in anhydrous DMF (70 mL) and cooled to 0° C. 4-Hydroxy phenyl acetic acid 18 (5.00 g, 0.329 mmol) was dissolved in DMF (30 mL), added to the cooled sodium hydride suspension and allowed to stir at room temperature for 2 h. After this time, the reaction was re-cooled to 0° C. and allyl bromide (11.3 mL, 0.131 mmol) was added. After stirring for 4.5 h at room temperature, it was poured into saturated brine, extracted with ether, washed organic layer with 10% KOH then brine. The organic layer was dried over magnesium sulfate, filtered and concentrated under reduced pressure. The crude product was purified by column chromatography (CHCl$_3$) to yield an oil (4.97 g, 0.0214 mmol) in 65% yield. R$_f$ 0.68 (CHCl$_3$). $^1$H NMR (CDCl$_3$) δ: 3.58 (s, 2H); 4.51 (d, 2H); 4.58 (d, 2H); 5.24 (m, 2H); 5.90 (m, 1H); 6.02 (m, 1H); 6.87 (d, 2H); 7.19 (d, 2H). $^{13}$C NMR (CDCl$_3$) δ: 40.39, 65.96, 68.80, 114.81, 117.60, 118.15, 126.16, 130.26, 132.05, 133.26, 157.72, 171.50. HRMS (EI) mass calculated for C$_{14}$H$_{16}$O$_3$: 232.1100. found (M+H): 232.1104.

Example 10

This example describes the synthesis of 2-(4-allyloxyphenyl)-3-hydroxy-3-phenyl propionic acid allyl ester, 22.

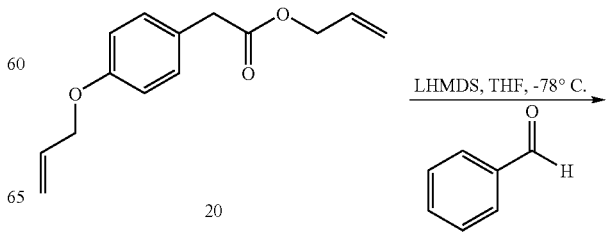

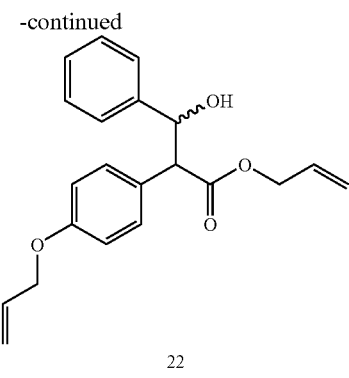

22

LHMDS (9.47 mL, 9.47 mmol) was added to a solution of 20 (2.00 g, 8.61 mmol) in anhydrous THF (120 mL) that was pre-cooled to −78° C. Benzaldehyde (0.88 mL, 8.61 mmol) was dissolved in THF and added to the cooled mixture. The reaction was warmed to −20° C. and stirred overnight. The next day it was quenched with saturated ammonium chloride, extracted aqueous layer with EtOAc, combined organic layers, dried over magnesium sulfate, filtered and concentrated under reduced pressure. The crude product was purified by column chromatography (10% EtOAc/Hex) to yield the compound 22 (2.01 g, 5.94 mmol) in 69% yield. $R_f$ 0.16 (10% EtOAc/Hex). $^1$H NMR (CDCl$_3$) δ: 3.07 (d, 1H); 3.84 (d, 1H); 4.44 (d, 2H); 4.64 (m, 2H); 5.24 (m, 4H); 5.85 (m, 1H); 6.01 (m, 1H); 6.71 (d, 2H); 6.99 (d, 2H); 7.09–7.18 (m, 5H).

Example 11

This example describes the synthesis of compound 2-(4-allyloxyphenyl)-3-phenylacrylic acid allyl ester, 24.

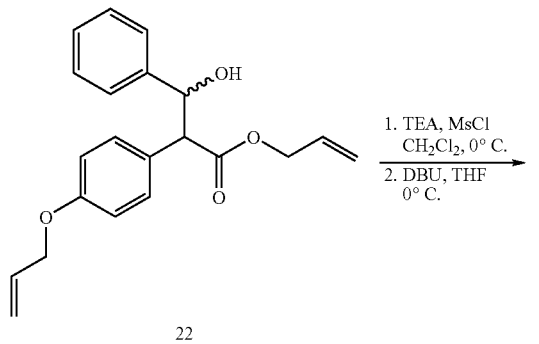

To a solution of 22 (1.00 g, 2.96 mmol) in dichloromethane (10 mL) that was cooled to 0° C., triethylamine (TEA) (1.2 mL, 8.87 mmol) was added followed by mesyl chloride (MsCl) (0.46 mL, 5.91 mmol). The reaction was stirred for 2 h, then diluted with ether, filtered through a plug of celite and concentrated under reduced pressure. The crude mesylate was diluted in anhydrous THF (40 mL), cooled to 0° C. and added 1,8-diazabicylco[5.4.0]undec-7-ene (DBU) (1.3 mL, 8.87 mmol). After stirred for 2 h at room temperature, added 10% HCl, extracted with chloroform, washed organic layer with saturated sodium bicarbonate, and brine then dried organic layer with magnesium sulfate, filtered and concentrated under reduced pressure. The crude product was purified by column chromatography (15% EtOAc/Hex) to yield 10 (0.90 g, 2.81 mmol) in 95% yield. $R_f$ 0.59 (15% EtOAc/Hex). $^1$H NMR (CDCl$_3$) δ: 4.53 (d, 2H); 4.69 (d, 2H); 5.28 (m, 4H); 5.93 (m, 1H); 5.07 (m, 1H); 6.90 (d, 2H); 7.13 (m, 7H); 7.81 (s, 1H). $^{13}$C NMR (CDCl$_3$) δ: 65.63, 68.76, 114.83, 117.72, 117.77, 128.03, 128.17, 128.90, 130.55, 131.01, 132.08, 132.24, 133.17, 134.81, 140.21, 158.22, 167.65. LRMS (+ESI) mass calculated for C$_{21}$H$_{20}$O$_3$: 320.1. found (M+H): 321.2.

Example 12

This example describes the synthesis of 2-(4-hydroxyphenyl)-3-phenyl acrylic acid, 26.

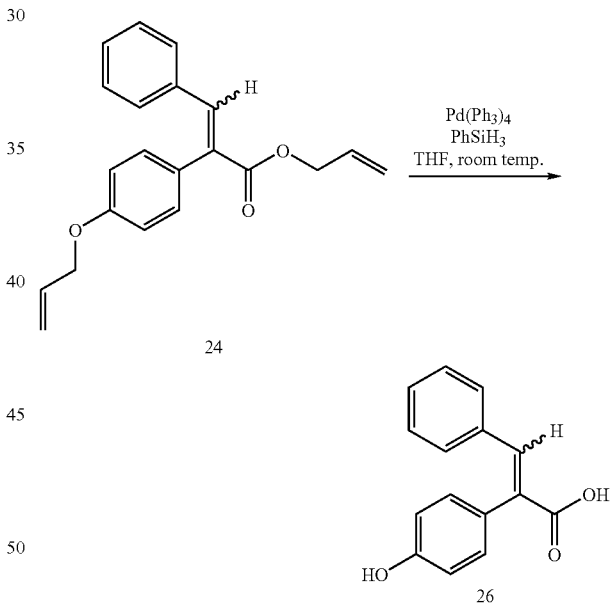

PhSiH$_3$ (0.78 mL, 6.24 mmol) was added to a solution of 24 in THF (35 mL) followed by the addition of Pd(PPh$_3$)$_4$ at room temperature. The reaction was stirred at room temperature under argon for 15 min. It was quenched by adding ddH$_2$O, added 1N HCl to decrease the pH to 2, extracted with dichloromethane, dried over magnesium sulfate, filtered and concentrated under reduced pressure. The crude mixture was purified by column chromatography (1:1 EtOAc/Hex) to yield 26 (266.9 mg, 1.11 mmol) in 71% yield. $R_f$ 0.33 (5% EtOAc/Hex). $^1$H NMR (MeOD) δ: 6.71 (d, 2H); 6.91 (d, 2H); 7.02 (m, 2H); 7.11 (m, 9H); 7.71 (s, 1H). LRMS (+ESI) mass calculated for C$_{15}$H$_{12}$O$_3$: 240.1. found (M+H): 241.0.

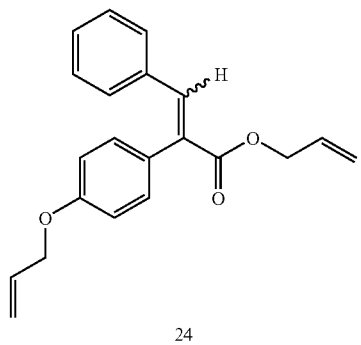

24

Example 13

This example describes the synthesis of E and Z N-[4-(2-Dimethylamino-ethoxy)-phenyl]-2-(4-hydroxy-phenyl)-3-phenyl-acrylamide, 28 and 30, respectively.

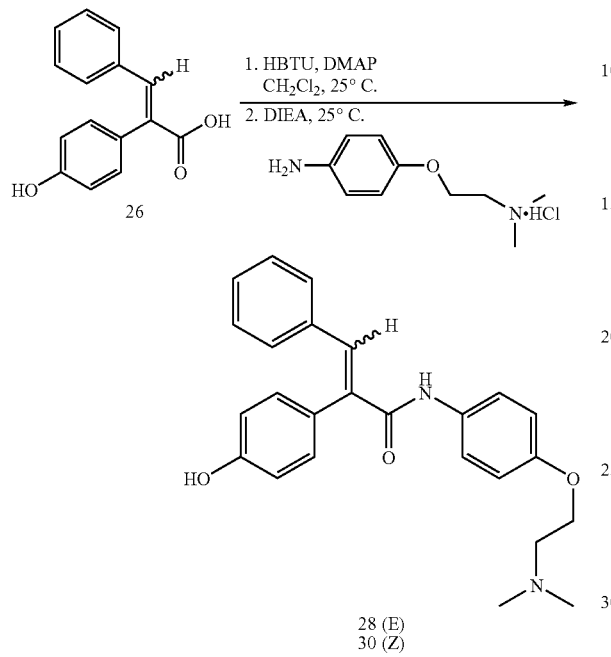

Compounds 28 and 30 were synthesized as described for compounds 8 and 9 (Example 4) using compound 26 (266 mg, 1.11 mmol), HBTU (462 mg, 1.22 mmol), DMAP (6.8 mg, 55.4 μmol), amine hydrochloride (264 mg, 1.22 mmol) and DIEA (0.77 mL, 4.43 mmol) to give the desired product (72 mg, 0.178 mmol) in 16% yield. $R_f$ 0.27 (10% MeOH/CHCl$_3$). $^1$H NMR (CDCl$_3$) δ: 2.36 (s, 6H); 2.77 (t, 2H); 4.06 (t, 2H); 6.80 (d, 2H); 6.86 (d, 2H); 7.19 (m, 10H); 7.80 (s, 1H); 8.06 (s, 1H). $^{13}$C NMR (CDCl$_3$) δ: 45.60, 58.03, 65.76, 114.74, 116.06, 121.82, 123.29, 126.71, 127.94, 128.62, 130.40, 130.82, 131.16, 133.74, 151.71, 155.92, 156.84, 166.63.

Example 14

This example describes the synthesis of 4-(2-dimethylaminoethoxy)benzoate, 42.

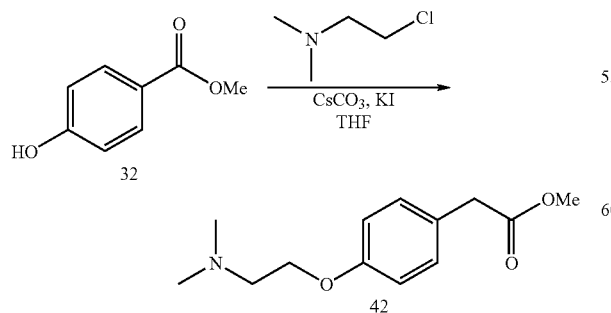

To a solution of methyl-4-hydroxybenzoate 32 (3.00 g, 19.7 mmol) in THF (80 mL), dimethylaminoethyl chloride (2.84 g, 19.7 mmol), cesium carbonate (34.78 g, 9.86 mmol), potassium iodide (65.5 mg, 0.394 mmol) were added and stirred with reflux overnight. After cooling to room temperature, ddH$_2$O was added, extracted with chloroform, dried over magnesium sulfate, filtered and concentrated under reduced pressure. The crude product was purified by column chromatography (10% MeOH/CHCl$_3$) to yield 12a (3.47 g, 15.5 mmol) in 79% yield. $R_f$ 0.31 (10% MeOH/CHCl$_3$). $^1$H NMR (CDCl$_3$) δ: 2.35 (s, 6H); 6.68 (t, 2H); 3.90 (s, 3H), 6.95 (d, 2H); 8.00 (d, 2H). $^{13}$C NMR (CDCl$_3$) δ: 45.90, 51.80, 58.11, 66.18, 114.12, 122.60, 131.51, 162.58, 166.28. LRMS (EI) mass calculated for C$_{12}$H$_{17}$NO$_3$: 223.1. found: 223.1.

Example 15

This example describes the synthesis of 4-(2-piperidin-1-ylethoxy)benzoate, 44.

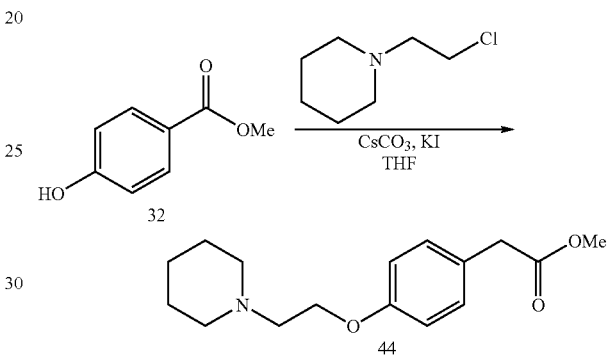

Procedure same as for compound 42 (example 14) using methyl-4-hydroxybenzoate (4.00 g, 2.62 mmol), 1-(2-chloroethyl) piperidine hydrochloride (4.76 g, 2.62 mmol), potassium carbonate (18.16 g, 13.14 mmol), potassium iodide (43.6 mg, 0.526 mmol) and DMF (100 mL). The crude product was purified by column chromatography (5% MeOH/CHCl$_3$) to yield compound 44 (5.54 g, 2.10 mmol) in 80% yield. $^1$H NMR (CDCl$_3$) δ: 1.45 (m, 2H); 1.62 (m, 4H); 2.50 (m, 4H); 2.80 (t, 2H); 3.84 (s, 3H); 4.19 (t, 2); 6.98 (d, 2H); 7.99 (d, 2H). $^{13}$C NMR (CDCl$_3$) δ: 24.15, 25.94, 51.82, 55.09, 57.75, 66.23, 114.16, 131.53.

Example 16

This example describes the synthesis of 4-(2-dimethylaminoethoxy)-N-methoxy-N-methylbenzamide, 46.

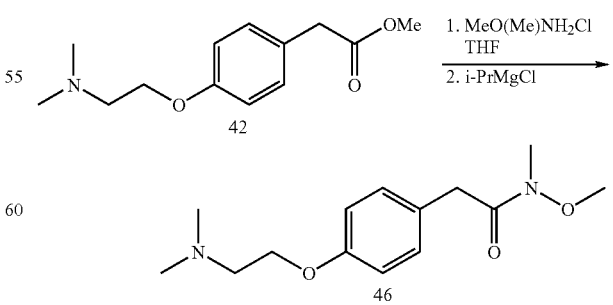

Compound 44 (2.69 g, 12.0 mmol) and methylmethoxy amine hydrochloride (1.82 g, 18.7 mmol) were suspended in anhydrous THF (100 mL) and cooled to −20° C. Isopropyl magnesium chloride (17.6 mL) was added dropwise while maintaining the temperature below −10° C. The reaction was warmed to room temperature and stirred overnight. Saturated ammonium chloride was added, extracted with ether, dried over magnesium sulfate, filtered and concentrated under reduced pressure. The crude product was purified by column chromatography (10% MeOH/CHCl$_3$) to yield compound 46 (2.04 g, 8.09 mmol) in 67% yield. R$_f$ 0.26 (10% MeOH/CHCl$_3$). $^1$H NMR (CDCl$_3$) δ: 2.35 (s, 6H); 2.78 (t, 2H); 3.35 (s, 3H); 3.58 (s, 3H); 4.10 (t, 2H); 6.90 (d, 2H); 7.70 (d, 2H). $^{13}$C NMR (CDCl$_3$) δ: 34.0, 46.0, 58.0, 61.2, 66.0, 114.0, 126.0, 130.0, 161.0, 169.0. LRMS (EI) mass calculated for C$_{13}$H$_{20}$N$_2$O$_3$: 252.1. found: 252.1.

Example 17

This example describes the synthesis of N-methoxy-N-methyl-4-(2-piperidin-1-ylethoxy)benzamide, 48.

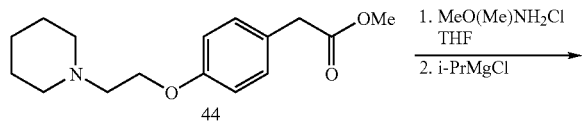

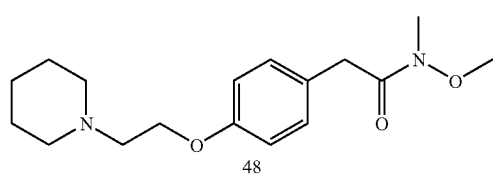

The procedure followed was the same as for compound 46, using compound 44 (2.00 g, 7.60 mmol), methyl-methoxyamine hydrochloride (1.15 g, 11.77 mmol), isopropyl magnesium chloride (11.36 mL, 2.0M THF) and THF (80 mL). The crude product was purified by column chromatography (10% MeOH/CHCl$_3$) to yield 48 (2.01 g, 6.88 mmol) in 91% yield. R$_f$ 0.41 (10% MeOH/CHCl$_3$). $^1$H NMR (CDCl$_3$) δ: 1.45 (m, 2H); 1.60 (m, 4H); 2.30 (m, 4H); 2.79 (t, 2H); 3.35 (s, 3H); 3.58 (s, 3H); 4.10 (t, 2H); 6.85 (d, 2H); 7.70 (d, 2H). $^{13}$C NMR (CDCl$_3$) δ: 24.16, 25.92, 55.07, 57.80, 60.86, 66.05, 113.84, 130.51, 160.10.

Example 18

This example describes the synthesis of 2-(4-tert-butoxyphenyl)-1-[4-(2-dimethylaminoethoxy)-phenyl]-3-phenyl-pent-2-en-1-one, 50.

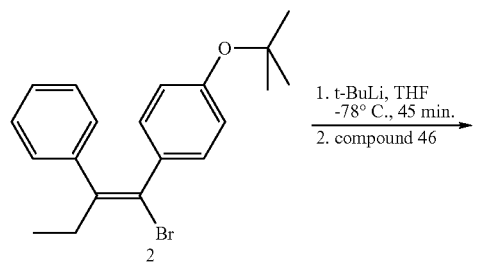

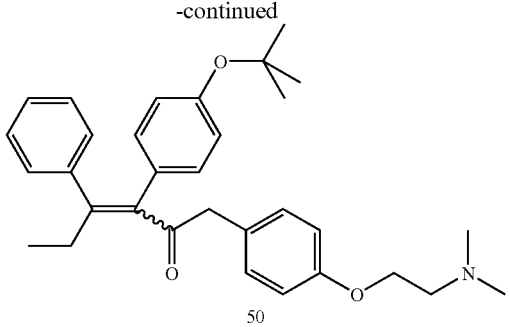

A solution of vinyl bromide 2 (200 mg, 0.556 mmol) in THF (10 mL) was cooled to −78° C. and t-butyl lithium (0.69 mL, 1.16 mmol) was added. After stirring for 45 min, compound 46 (140 mg, 0.556 mmol) was added and stirred from −78° C. to room temperature over 3 h. The reaction was quenched with saturated ammonium chloride, extracted with chloroform, dried over magnesium sulfate and concentrated under reduced pressure. The crude mixture was purified by column chromatography (10% MeOH/CHCl$_3$) to yield compound 50 (22 mg, 0.0466 mmol) as a mixture of isomers in 10% yield. R$_f$ 0.49 (10% MeOH/CHCl$_3$). $^1$H NMR (CDCl$_3$) δ: 0.85 (t, 3H); 0.92 (t, 2H); 1.25 (s, 6H); 1.35 (s, 9H); 2.29 (s, 3H); 2.31 (s, 6H); 2.37 (q, 2H); 2.54 (q, 1H); 2.69 (t, 1H); 2.74 (t, 2H); 4.00 (t, 1H): 4.09 (t, 2H); 6.63 (d, 2H); 7.71 (d, 1H); 6.92 (m, 4H); 7.12 (m, 8H); 7.73 (d, 1H); 7.99 (d, 1H). $^{13}$C NMR (CDCl$_3$) δ: 12.87, 13.22, 27.28, 28.74, 28.51, 29.23, 45.81, 58.01, 65.96, 66.14, 113.84, 114.39, 123.46, 123.99, 126.58, 126.83, 127.21, 128.14, 128.30, 128.53, 129.38, 129.48, 129.90, 130.03, 130.16, 131.75, 131.95, 132.17, 132.62, 136.97, 137.88, 139.86, 140.36, 142.85, 144.46, 154.15, 154.78, 162.26, 162.93, 197.11, 197.37.

Example 19

This example describes the synthesis of 2-(4-tert-butoxyphenyl)-3-phenyl-1-[4-(2-piperidin-1-ylethoxy)-phenyl]pent-2-en-1-one 52.

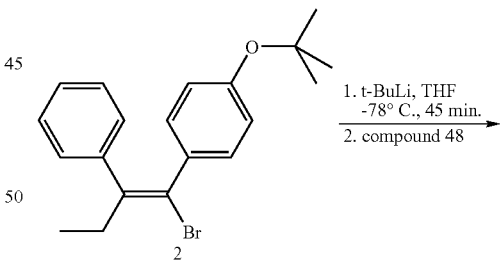

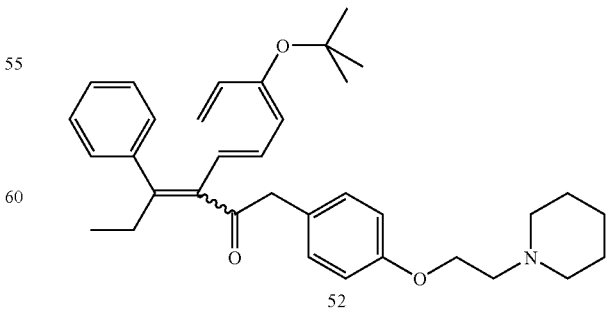

The procedure used to prepare compound 50 was followed, using vinyl bromide (200 mg, 0.556 mmol), THF (10 mL), t-butyl lithium (0.65 mL, 1.11 mmol) and compound 48 (163 mg, 0.556 mmol). The crude compound was purified by column chromatography (10% MeOH/CHCl$_3$) to yield compound 52 as a mixture of isomers in 10% yield. R$_f$ 0.44 (10% MeOH/CHCl$_3$). $^1$H NMR (CDCl$_3$) δ: 0.85 (t, 2H); 0.91 (t, 3H); 1.20 (s, 6H); 1.31 (s, 9H); 1.41 (m, 3H); 1.57 (m, 6H); 2.40 (q, 1H); 2.48 (m, 6H); 2.56 (q, 2H); 2.72 (t, 2H); 2.77 (t, 2H); 4.04 (t, 2H); 4.11 (t, 1H); 6.64 (d, 1H); 6.66 (d, 2H); 6.75 (d, 2H); 6.89 (dd, 2H); 7.04 (d, 2H); 7.12 (m, 9H); 7.61 (d, 1H), 7.72 (d, 2H); 7.98 (d, 1H). $^{13}$C NMR (CDCl$_3$) δ: 12.01, 13.22, 18.03, 23.97, 25.61, 27.29, 28.38, 28.85, 54.93, 57.58, 60.83, 65.76, 113.86, 114.35, 115.01, 123.46, 123.82, 127.22, 127.91, 128.56, 129.38, 129.48, 130.03, 130.74, 131.98, 132.19, 140.36, 144.46, 162.22. LRMS (+ESI) mass calculated for C$_{34}$H$_{41}$NO$_3$: 511.3. found (M+H): 512.0.

Example 20

This example describes the synthesis of 1-[4-(2-Dimethylaminoethoxy)-phenyl]-2-(4-hydroxyphenyl)-3-phenylpent-2-en-1-one, 54.

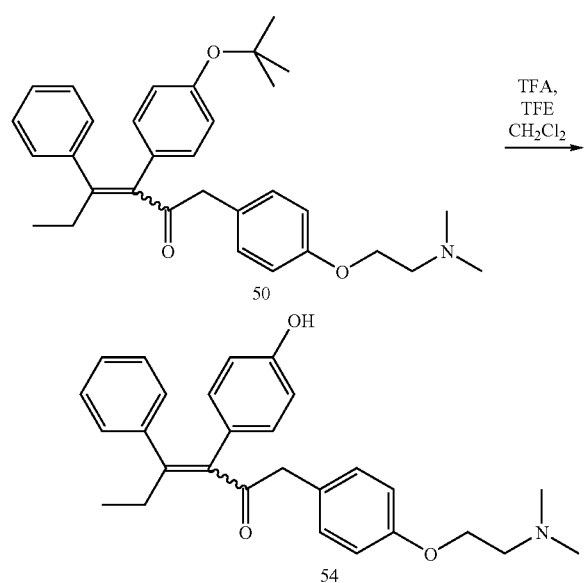

The same procedure was used for deprotection of 50 as was used to prepare 8 and 9 (example 4). The following amounts of reagents were used: 50 (22 mg, 0.0464 mmol), trifluoroethanol (0.34 mL), trifluoroacetic acid (0.66 mL), and dichloromethane (0.66 mL). The crude product was purified using preparatory TLC (10% MeOH/CHCl$_3$) to yield 54 as a mixture of isomers (11 mg, 0.265 mmol) in 58% yield. R$_f$ 0.26 (10% MeOH/CHCl$_3$). $^1$H NMR (CDCl$_3$) δ: 0.86 (t, 3H); 0.93 (t, 2H); 2.31 (s, 3H); 2.33 (s, 6H); 2.37 (q, 2H); 2.56 (q, 1H); 2.72 (t, 1H); 2.76 (t, 2H); 4.00 (t, 1H): 4.08 (t, 2H); 6.43 (d, 2H); 6.65 (d, 1H); 6.72 (d, 1H); 6.83 (dd, 3H); 7.15 (m, 8H); 7.71 (d, 1H); 7.94 (d, 1H). $^{13}$C NMR (CDCl$_3$) δ: 12.94, 13.27, 27.284, 29.35, 45.53, 57.80, 65.65, 113.84, 114.34, 115.23, 115.65, 126.81, 127.18, 127.92, 128.07, 128.32, 128.54, 129.21, 129.41, 129.87, 130.20, 130.78, 131.23, 13.99, 132.16, 136.89, 138.40, 140.03, 140.39, 140.43, 142.16, 144.30, 155.33, 155.98, 162.01, 162.63, 197.40, 198.82.

Example 21

This example describes the synthesis of 2-(4-hydroxyphenyl)-3-phenyl-1-[4-(2-piperidin-1-yl-ethoxy)-phenyl]-pent-2-en-1-one, 56.

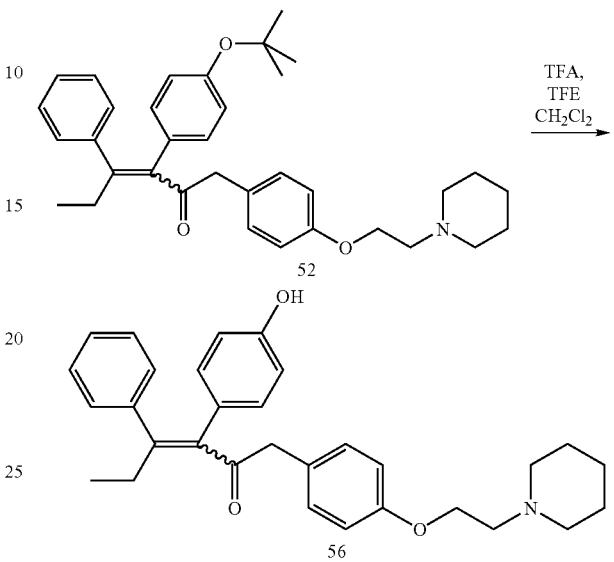

The same procedure was used for deprotection of 52 as was used to prepare 8 and 9 (example 4). The following amounts of reagents were used: 52 (28 mg, 0.0547 mmol), trifluoroethanol (0.40 mL), trifluoroacetic acid (0.78 mL), and dichloromethane (0.78 mL). The crude product was purified using prep TLC (10% MeOH/CHCl$_3$) to yield 56 as a mixture of isomers (13 mg, 0.286 mmol) in 54% yield. R$_f$ 0.11 (10% MeOH/CHCl$_3$). $^1$H NMR (CDCl$_3$) δ: 0.88 (t, 2H); 0.95 (t, 3H); 1.45 (m, 3H); 1.62 (m, 6H); 2.40 (q, 1H); 2.54 (m, 6H); 2.60 (q, 2H); 2.75 (t, 2H); 2.80 (t, 2H); 4.06 (t, 2H); 4.13 (t, 1H); 6.46 (d, 1H); 6.62 (d, 2H); 6.74 (d, 2H); 6.83 (t, 2H); 7.13 (m, 9H); 7.72 (d, 2H); 7.96 (d, 1H). $^{13}$C NMR (CDCl$_3$) δ: 12.92, 13.28, 23.85, 25.28, 27.28, 29.33, 54.89, 57.56, 65.30, 113.85, 114.36, 115.31, 115.71, 126.81, 127.18, 127.91, 128.06, 128.56, 129.31, 129.41, 129.81, 130.13, 130.18, 130.75, 132.02, 132.18, 137.91, 140.44, 144.26, 155.22, 162.06, 162.70, 197.52, 197.80.

Example 22

This example describes the identification and characterization of a previously unidentified membrane associated estrogen receptor and an assay for the identification and evaluation of SERMs.

General Methods for SERM Assays and Screening

Female Topeka guinea pigs (400–600 g), bred in the Oregon Health Sciences University institutional breeding facility and female multicolor guinea pigs (400–500 g, Elm Hill, Mass.) were used. The guinea pigs were maintained under constant temperature (26° C.) and light (on between 06:30–20:30 h). Animals were housed individually, with food and water provided ad libitum. They were ovariectomized under ketamine/xylazine anesthesia (33 mg/kg & 6 mg/kg, respectively; subcutaneous) 5–7 days prior to experimentation, and given sesame oil vehicle (0.1 mL subcutaneous) 24 h prior to experimentation. Serum estrogen concentrations were determined by radioimmunoassay (Wagner et al., 2001) from trunk blood collected on the day of experimentation and were less than 10 pg/mL. An additional group of animals (n=6) were ovariectomized and after one week injected with oil vehicle, estradiol benzoate (25 µg in oil) or compound 8 (example 4, 25 µg in oil) 24 h prior to sacrifice.

Wild-type C57BL/6 mice in these studies were obtained from Jackson laboratories. All animals were maintained under controlled temperature (25° C.) and photoperiod conditions (14-h light, 10-h dark; lights on between 0700 and 2100) with food and water ad libitum. Adult mice were ovariectomized under isoflurane anesthesia, and allowed to recover for 1 week. At this time the animals were injected daily for 2 days with oil vehicle, estradiol benzoate (EB; 1 µg) or compound 8 (2 or 5 µg), and anesthetized and killed by decapitation after 24 h. The uteri were collected, weighed and fixed in 4% paraformaldehyde for later histological analysis (data not shown).

Commercially Available Drugs:

Drugs were purchased from Calbiochem (LaJolla, Calif., USA) unless otherwise specified. Tetrodotoxin (TTX; Alomone, Jerusalem, Israel) was dissolved in Milli-Q $H_2O$ and further diluted with 0.1% acetic acid (final concentration 1 mM; pH 4–5). 17β-estradiol (17β-estradiol) was purchased from Steraloids (Wilton, N.H., USA), recrystallized to ensure purity and dissolved in 100% ethanol to a stock concentration of 1 mM. 17α-estradiol (1 mM, Steraloids), anti-estrogen: ICI 182, 780 (10 mM, Tocris Cookson, Ballwin, Mo.) and the selective estrogen receptor modulators 4-OH-tamoxifen (10 mM, Steraloids), raloxifene (10 mM, Eli Lilly, Indianapolis, Ind.) and compound 8 (10 mM) were also dissolved in 100% ethanol. 17β-estradiol 17-hemisuccinate: BSA (17β-estradiol-BSA, 1 mM, Steraloids) was dissolved in $H_2O$. The protein kinase A inhibitor, H-89 dihydrochloride (10 mM), the protein kinase A activator forskolin (50 mM), the protein kinase C inhibitors bisindolylmaleimide I hydrochloride (BIS, 100 µM), Gö6976 (2 mM) and rottlerin (10 mM), the phospholipase C inhibitor U73122 (20 mM), the less active analog U73343 (20 mM) and the MEK1 inhibitor PD98059 (50 mM) were dissolved in DMSO. Protein kinase A inhibitory peptide 6–22 Amide (1 mM), the protein kinase A inhibitor: Rp-cAMPS (50 mM) and Cholera toxin A subunit (1 µg/µL) were dissolved in $H_2O$. The Gq binding protein designed to mimic the C terminus of the Gq α subunit and Gs α binding protein designed to mimic the C terminus of the Gs a subunit were synthesized by PeptidoGenic Research (Livermore, Calif.). The peptide sequence for Gq peptide was Ac-LGLN-LKEYNLV-OH [SEQ ID NO: 15] and for Gs peptide was CRMHLRQYELL [SEQ ID NO: 16]. The peptides were also dissolved in $H_2O$. BAPTA tetrasodium salt (1,2-bis-(o-aminophenoxyethane)-N,N,N',N'-tetraacetic acid) was dissolved in the internal solution at a 10 mM concentration. Aliquots of the stock solutions were stored as appropriate until needed.

Statistical Analyses:

Statistical analyses for comparing between groups were performed using a one-way analysis of variance (with post hoc (Newman-Keuls) paired analysis). Differences were considered statistically significant if the probability of error was less than 5%.

Tissue Preparation:

On the day of experimentation the animal was decapitated, its brain removed from the skull and the hypothalamus dissected. The resultant hypothalamic block was mounted on a plastic cutting platform that was then secured in a vibratome well filled with ice-cold, oxygenated (95% $O_2$, 5% $CO_2$) artificial cerebrospinal fluid (aCSF, in mM: NaCl, 124; $NaHCO_3$ 26; dextrose, 10; HEPES, 10; KCl, 5; $NaH_2PO_4$, 2.6; $MgSO_4$, 2; $CaCl_2$, 1). Four coronal slices (350 µm) through the arcuate were cut. The slices were transferred to a multi-well auxiliary chamber containing oxygenated aCSF, and kept there until electrophysiological recording after approximately 2 h.

Electrophysiology:

Whole-cell patch recordings in voltage clamp were performed as previously described (Wagner et al., 2001). Briefly, slices were maintained in a chamber perfused with warmed (35° C.), oxygenated aCSF containing the same constituents and respective concentrations except for $CaCl_2$, which was raised to 2 mM. Artificial CSF (aCSF) and all drug solutions were perfused via a peristaltic pump at a rate of 1.5 mL/min. Drug solutions were prepared in 20 mL syringes by diluting the appropriate stock solution with aCSF, and the flow was controlled via a three-way stopcock.

Figure 1:
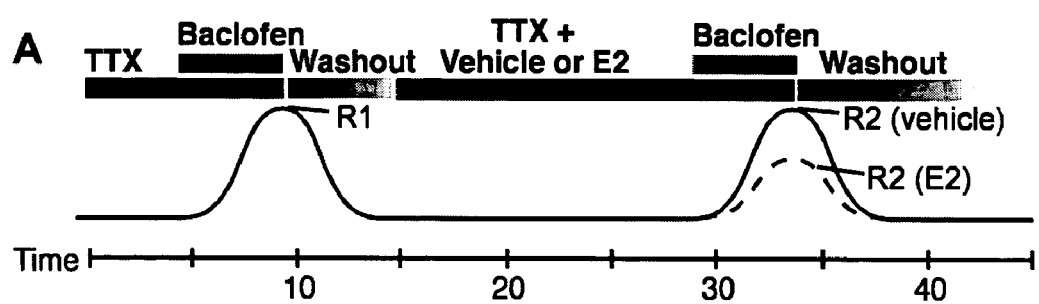
FIG. 1 is a schematic illustrating the protocol for drug administration in the whole-cell patch, voltage clamp studies.

For whole-cell recordings, electrodes were fabricated from borosilicate glass (World Precision Instruments, Inc., Sarasota, Fla., USA; 1.5 mm O.D.). Resultant electrodes were then filled with an internal solution containing 0.5% biocytin and consisting of the following in mM: $K^+$ gluconate, 128; NaCl, 10; $MgCl_2$, 1; EGTA, 11; HEPES, 10; ATP, 1.2; GTP, 0.4; the pH was adjusted to 7.3–7.4 with 1 N KOH; 272–315 mOsm. Voltage pulses were amplified and passed through the electrode using an Axopatch 1D preamplifier (Axon Instruments, Union City, Calif.). The resultant current deflections were monitored using a digital oscilloscope (Tektronix 2230, Beaverton, Oreg., USA). Upon the reduction of the current deflection, negative pressure was applied via a 5 mL syringe connected by polyethylene tubing to the electrode in order to form a seal (>1 GΩ). Following formation of a seal, intracellular access was achieved by suction, followed by perfusion with 1 µM TTX for at least 4–6 min to block spontaneous firing and synaptic potentials before applying the $GABA_B$ receptor agonist baclofen (FIG. 1). All the responses to baclofen were measured in voltage clamp as outward currents ($V_{hold}$=−60 mV), and only those cells that showed less than 10% change in access resistance (access resistances ranged from 20–30 MΩ) throughout the recording were included in this study. Membrane currents underwent analog-digital conversion via a Digidata 1200 interface coupled to pClamp 7.0 (Axon Instruments, Union City, Calif.). Low-pass filtering of the currents was conducted at a frequency of two KHz. The liquid junction potential was −10 mV, and was corrected for in subsequent data analysis.

Figure 2:
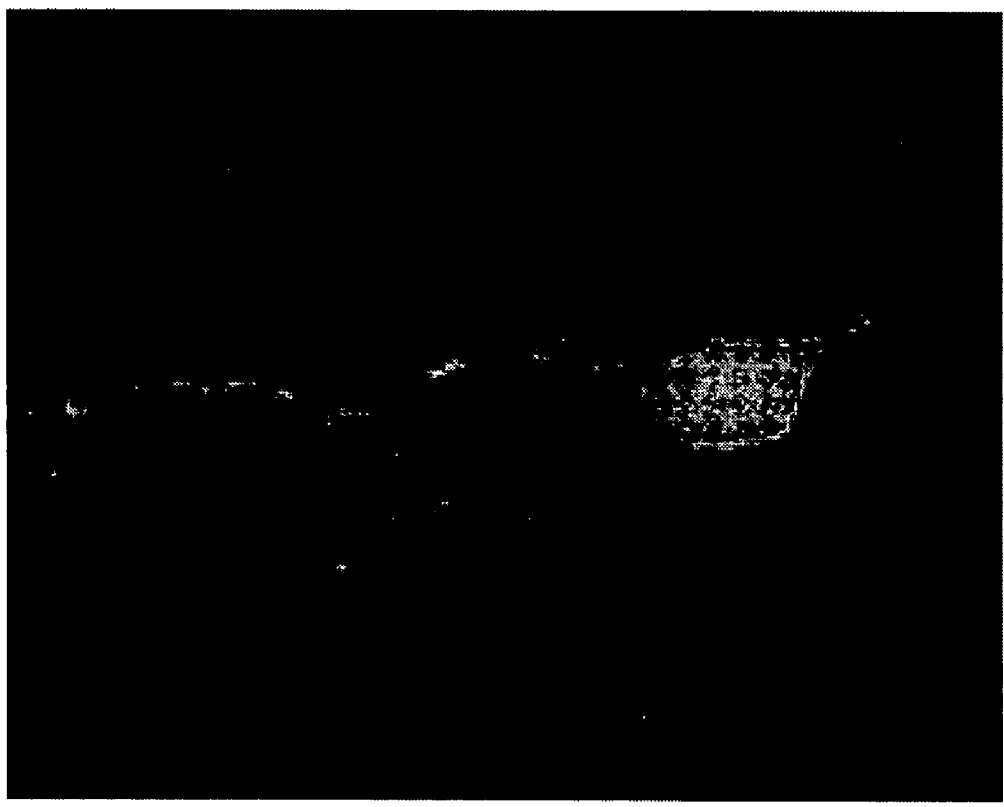
FIG. 2 is an image showing an example of a biocytin-filled neuron after whole-cell patch-clamp recording for 13 min illustrating the extent of the biocytin labeling.

Post-Hoc Identification of Hypothalamic Arcuate Neurons:

Following electrophysiological recording, the slices were fixed with 4% paraformaldehyde in Sorensen's phosphate buffer (pH 7.4) for 120 min, immersed overnight in 20% sucrose dissolved in Sorensen's buffer and then frozen in O.C.T. embedding medium and prepared for immunocytochemistry as previously described (Kelly and Rønnekleiv, 1994). Briefly, coronal sections (20 µm) were cut on a cryostat (Leitz Model 1720 Digital Cryostat) and mounted on Fisher SuperFrost Plus slides. Sections were washed for 5 min with 0.1 M sodium phosphate buffer (pH 7.4), and then streptavidin-Cy2 (Jackson ImmunoResearch Laboratories, Pa.) (1:1000) was applied for 2 h. The reaction was terminated by washing with buffer. The slices were scanned for the injected neuron with a Nikon Eclipse 800 fluorescence microscope (Nikon Instruments, Melville, N.Y.). After localization of the biocytin-filled neurons, the slides containing the appropriate sections were processed for the presence of tyrosine hydroxylase (TH) or β-endorphin using fluorescence immunohistochemistry as described previously (Kelly and Rønnekleiv, 1994). Briefly, the sections with the biocytin-identified neurons were incubated overnight with a monoclonal TH antibody at 1:10,000 (Diasorin, Stillwater, Minn.), or with a polyclonal β-endorphin antibody at 1:5,000 (Dave et al., 1985), washed in 0.1 M phosphate buffer followed by incubation with a goat anti-mouse IgG-Cy3 at 1:500 or donkey anti-rabbit IgG-Cy3 at 1:500, respectively (Jackson ImmunoResearch Laboratories, Pa.). The sections were washed with sodium phosphate buffer, and coverslips were applied using a glycerolglycine buffer containing 5% N-propylgallate. Immunostained cells were photographed using a Nikon microscope. See FIG. 2.

Estrogen Receptor Binding Assays:

The relative binding affinity of compounds for the estrogen receptors (ER)α and (ER)β was determined using a spin column assay with commercially available full-length forms of both (ER)α and (ER)β (Pan Vera Corp, Madison, Wis., USA). Receptor was added to a final concentration of 15 nM to a solution containing 10 mM Tris, pH 7.5, 10% glycerol, 2 mM DTT and 1 mg/mL BSA and 3 nM [2,4,6,7,16,17-$^3$H]estradiol at 4° C. 100 μL of the solution was added to 1 μL of the ligand in ethanol, mixed gently by pipetting and incubated at 4° C. overnight. The mixture was then applied to a micro spin column containing G-25 Sephadex (Harvard Apparatus Inc.) equilibrated in binding buffer (minus tritiated estradiol) according to the manufacturer's instructions. Bound estradiol was separated from free ligand by spinning at 2000×g for 4 min at room temperature. The filtrate was then added to 2.5 mL of scintillant and counted in a liquid scintillation counter. A binding curve was fitted using a single binding site competition model with the Prism (GraphPad Software, San Diego, Calif.) statistical analysis software package. The standard deviation was determined to be less than 0.2 log units from the $EC_{50}$ value. Percent relative binding affinity was then determined by dividing the $IC_{50}$ determined for unlabeled estradiol by the ligand $IC_{50}$ and multiplying by 100.

Dispersed Single-Cell RT-PCR:

Guinea pig 350 μm coronal hypothalamic slices were cut on a vibratome from caudal to rostral and placed in an auxiliary chamber containing oxygenated aCSF. The slices were allowed to recover for 1–2 h in the chamber before dispersion. The arcuate nucleus of the hypothalamus was microdissected and incubated in 2–3 mL of Hank's balanced salt solution (HBSS in mM; $CaCl_2$, 1.26; $MgSO_4$, 1; KCl, 5.37; $KH_2PO_4$, 0.44; NaCl, 136.89; $Na_2HPO_4$, 0.34; D-glucose, 5.55; Hepes, 15 in DEPC-treated water (pH 7.3, 300 mOsm) containing 1 mg/mL protease XIV (Sigma, St. Louis, Mo.) for approximately 15 min at 37° C. The tissue was then washed four times in one volume low calcium aCSF and two times in HBSS. The cells were isolated by trituration with flame-polished Pasteur pipettes, dispersed on a dish and continuously perfused with HBSS at a rate of 1.5 mL/n. Cells were visualized using a Nikon inverted microscope and individual neurons were patched and harvested into the patch pipette by applying negative pressure. The content of the pipette was expelled into a siliconized microcentrifuge tube containing 5 μL of the following solution: 0.5 μL of 10× buffer (100 mM Tris-HCL, 500 mM KCl, 1% Triton-X 100; Promega, Madison, Wis.), 15 U RNasin (Promega), 0.5 μL 100 mM DTT and DEPC-treated water.

In addition, hypothalamic tissue was homogenized and total RNA extracted using the RNeasy kit (Qiagen, Valencia, Calif.) according to the manufacturer's protocol. The harvested cell solution and 25 ng of hypothalamic total RNA in 1 μL were denatured for 5 min at 65° C., cooled on ice for 5 min, and then single stranded cDNA was synthesized from cellular RNA by adding 50 U MuLV reverse transcriptase (Applied Biosystems, Foster City, Calif.), 1.5 μL 10× buffer, 2 μM $MgCl_2$, 0.2 μL deoxynucleotide triphosphates (dNTPs), 15 U RNasin, 10 mM DTT, 100 ng random hexamers and DEPC-treated water to a final volume of 20 μL. Cells and tissue RNA used as negative controls, were processed as described above but without reverse transcriptase. The reaction mixtures were incubated at 42° C. for 60 min, denatured at 99° C. for 5 min and cooled on ice for 5 min.

PCR was performed using 3 μL of cDNA template from each RT reaction in a 30 μL PCR reaction volume containing: 3 μL 10× buffer, 2.4 μL $MgCl_2$ (2 mM final concentration for TH, POMC, $GABA_B$-R2, PKCδ, adenylyl cyclase VII and GAPDH) or 3.6 μL $MgCl_2$ (3 mM final concentration for GAD), 0.2 mM dNTPs, 0.2 μM forward and reverse primers, 2 Units Taq DNA polymerase (Promega) and 0.22 μg TaqStart Antibody (Clontech, Palo Alto, Calif.). Taq DNA polymerase and TaqStart Antibody were combined and incubated at room temperature for 5 min, the remainder of the reaction contents were added to the tube and incubated at 94° C. for 2 min. Then, each reaction went through 60 cycles (35 cycles for GAPDH) of amplification according to the following protocols: 94° C., 45 sec; 55° C. (GAD), 57° C. (PKCδ), 58° C. ($GABA_B$-R2), 60° C. (TH and adenylyl cyclase VII), 61° C. (POMC), 63° C. (GAPDH) 45 sec; 72° C., 1 min 10 sec; with a final 72° C. extension for 5 min. Ten microliters of the PCR products were visualized with ethidium bromide on a 1.5% agarose gel.

All of the primers were synthesized by Invitrogen (Carlsbad, Calif.) and were as follows: Guinea pig GAD65; 207 bp product, forward primer 5'-GGCTCTGGTGATGGAATA-3' [SEQ ID NO: 1], reverse primer 5'-CAGAATCACGCTGTCTGTT-3' [SEQ ID NO: 2], Guinea pig TH; 223 bp product, forward primer 5'-TCCACGTTATACTGGTTCAC-3' [SEQ ID NO: 3], reverse primer 5'-TTGCATCACTGAAGCTCTC-3' [SEQ ID NO: 4]; Guinea pig $GABA_B$-R2; 241 bp product, forward primer 5'-TGTTTGTGCCAAAGCTCATC-3' [SEQ ID NO: 5] reverse primer 5'-GTGTCTTGCAGTTGCATAGT-3' [SEQ ID NO: 6], Guinea pig POMC (accession number S78260); 344 bp product, forward primer (bases 40–60) 5'-CTGGCCTTGCTGCTTCAGAT-3' [SEQ ID NO: 7] reverse primer (bases 383–363) 5'-ATGGAGTAGGAGCGCTTGTC-3' [SEQ ID NO: 8]; Guinea pig GAPDH; 212 bp product (accession number CPU51572), forward primer 5'-CATCCACTGGTGCTGCCAAG-3' [SEQ ID NO: 9], reverse primer 5'-GTCCTCGGTGTAGCCCAAGA-3' [SEQ ID NO: 10]. Human protein kinase Cδ; 251 bp product (accession number L07861) forward primer (bases 1127–1147) 5'-AAAGGCAGCTTCGGGAAGGT-3' [SEQ ID NO: 11], reverse primer (bases 1377–1357) 5'-TGGATGTGGTACATCAGGTC-3' [SEQ ID NO: 12]. Guinea pig adenylyl cyclase VII; 235 bp product, forward primer 5'-CTGTTCGGCAAGTTTGACCAG-3' [SEQ ID NO: 13], reverse primer 5'-TGACGCCACACAGCACATT-3' [SEQ ID NO: 14].

17β-Estradiol and SERMs Rapidly Attenuate the GABA$_B$ Response in Hypothalamic Dopamine and Pro-Opiomelanocortin (POMC) Neurons:

The following data demonstrate that 17β-estradiol and SERMs rapidly attenuate a baclofen-induced GABA$_B$ response in hypothalamic neurons, which indicates that these compounds affect neurotransmission through non-transcriptional events. Whole cell recordings were made in arcuate neurons (n=195) from ovariectomized female guinea pigs. FIG. 1 is a schematic illustrating the protocol for drug administration in the whole-cell patch, voltage clamp studies ($V_{hold}$=−60 mV). After seals were formed and the whole-cell configuration was obtained, slices were perfused with TTX (1 μM) for 5 min. The first GABA$_B$ receptor-mediated response was generated by perfusing the GABA$_B$ agonist baclofen (at EC$_{50}$ concentration of 5 μM) until a steady-state outward current was obtained (first response, R1). After baclofen wash out, the current returned to its predrug resting level. The cells were then treated with 17β-estradiol and/or other drugs for 15 min, and baclofen (5 μM) was perfused again, and a second response (R2) was measured. The effects of 17β-estradiol and/or other drugs on the baclofen response are expressed as a percentage of R2 over R1. A subgroup of these neurons (n=55) was identified using dual labeling immunocytochemistry (data and images not shown). This revealed that 41% of the cells were TH-positive (i.e. dopamine neurons) and 39% were β-endorphin-positive (i.e. POMC neurons). Moreover, based on dual immunocytochemical staining and in situ hybridization for GAD$_{65}$ a subgroup of arcuate dopamine neurons co-express GABA (Rønnekleiv, unpublished findings), which was substantiated by the scRT-PCR data (see below). For the electrophysiology analysis, only cells with gigaohm or better seals were included in this study. The mean resting membrane potential was −54.3±0.4 mV at a 0 pA holding current, and the mean input resistance was 1.9±0.3 GΩ. Moreover, fifty percent of A12 dopamine neurons exhibited a T-type Ca$^{2+}$ current and a hyperpolarization-activated, cation current ($I_h$) (Loose et al., 1990). Seventy-one percent of the POMC neurons exhibited $I_h$ and a transient outward K$^+$ current ($I_A$) (Kelly et al., 1990). Therefore, the passive membrane properties measured with whole-cell patch recording is similar to results obtained using single electrode voltage clamp recordings (Loose et al., 1990; Kelly et al., 1990).

The whole-cell recording method used to measure the rapid effects of 17β-estradiol on the activation of the G protein-coupled, inwardly-rectifying K$^+$ channel (GIRK) conductance by the GABA$_B$ receptor agonist baclofen. 17β-estradiol rapidly attenuates both μ-opioid and GABA$_B$ receptor-mediated responses in hypothalamic arcuate neurons (Lagrange et al., 1994; Lagrange et al., 1996; Lagrange et al., 1997). Therefore, for measuring 17β-estradiol modulation of the GABA$_B$ response an EC$_{50}$ concentration (5 μM) of baclofen was used according to the protocol depicted in FIG. 1. A robust outward current was measured in response to baclofen that subsided after washout (FIG. 5 graph A and FIG. 6). The application of baclofen 20 min later elicited the same robust response, suggesting that desensitization and run-down were not occurring in response to successive applications of 5 μM baclofen. However, if 17β-estradiol (100 nM) was applied during the interim period (i.e. after the washout of the first application of baclofen), there was a significant (p<0.005) decrease of 41% in the response to a second application of baclofen (FIG. 5 graph B and FIG. 6). Current/voltage relationships generated before and during the application of 100 nM 17β-estradiol showed that this steroid did not change the reversal potential for the baclofen-mediated response: control $E_{baclofen}$=−88.8±3.6 mV, n=13; versus after 17β-estradiol $E_{baclofen}$=−85.4±3.9 mV, n=12 (FIGS. 3A and 3B). The effects of 17β-estradiol were stereospecific such that the biologically inactive stereoisomer 17β-estradiol (100 nM) had no effect on the baclofen response (FIG. 5 graph C and FIG. 6). Furthermore, the effects of 17β-estradiol were blocked by the anti-estrogen ICI 182, 780, when co-perfused with 17β-estradiol (FIG. 6). Treatment with ICI 182, 780 alone had no effect on the baclofen response (data not shown).

This previously unidentified estrogen receptor was determined to be membrane associated by using the membrane impermeable estrogen conjugate 17β-estradiol-BSA. 17β-estradiol-BSA (100 nM) was fully efficacious in inhibiting the baclofen response indicating that this estrogen receptor-mediated response is initiated at the plasma membrane (FIG. 5 graph D and FIG. 6). The integrity of the 17β-estradiol-BSA preparation was verified by performing a 17β-estradiol radioimmunoassay of the slice perfusate. No unbound 17β-estradiol was found in the media (data not shown) indicating that 17β-estradiol-BSA conjugate did not contain contaminating free 17β-estradiol.

The previously unidentified, membrane associated estrogen receptor was characterized by using several SERMs. Tamoxifen (1 μM) was inactive (p>0.05 versus control) and did not attenuate the effects of 17β-estradiol on the baclofen activation of GIRK (R2/R1 for 17β-estradiol: 58.6±3.4%, n=10; versus tamoxifen+17β-estradiol: 60.4±6.6%, n=5). However, 4-OH tamoxifen (1 μM) did partially mimic the actions of 17β-estradiol by blocking the baclofen response by 25% (FIG. 6). With reference to FIG. 6, 17β-estradiol (100 nM) attenuated the GABA$_B$ receptor-mediated outward current by 41%. The inhibitory effects of 17β-estradiol on the baclofen response were blocked by the estrogen receptor antagonist ICI 182, 780 (1 μM). Bovine Serum Albumin-conjugated Estrogen (17β-estradiol-BSA, 100 nM), 4-OH tamoxifen (1 μM), raloxifene (1 μM), GW5638 (1 μM) and compound 8 (10 nM) also inhibited the baclofen response, but 17α-estradiol (1 μM) had no effect. Bars represent the mean±S.E.M. of 4–11 cells tested per group (*p<0.005, p<0.01, *p<0.05, versus vehicle-control group). Because 4-OH tamoxifen always exists as an E/Z mixture of olefin isomers (Katzenellenbogen et al., 1985), it is possible that only one of the isomers is active at mediating this novel estrogen response. Raloxifene (1 μM), another SERM with a hydroxylated aromatic ring, completely mimicked the actions of 17β-estradiol in terms of efficacy in the suppression of the baclofen response (FIG. 6). In contrast, the non-hydroxylated SERM GW-5638, which structurally resembles the triphenylethylene core of tamoxifen, was found to be significantly more efficacious than 17β-estradiol at inhibiting GIRK channel activation by baclofen (FIG. 6).

Compound 8 is a SERM Devoid of Nuclear ER Activity that Selectively Attenuates Rapid Responses:

All of the above mentioned compounds are high affinity ligands for the nuclear estrogen receptors, which complicates the interpretation of the observed pharmacology and makes it difficult to exclude unequivocally a role for nuclear estrogen receptors. However, compound 8 (example 4) has approximately one million-fold reduced binding affinity for the nuclear estrogen receptor (ER)α or ERβ compared to that of 17β-estradiol (Table 1). Moreover, unlike 4-OH tamoxifen, compound 8 is geometrically stable and does not exist as a mixture of E/Z olefin isomers. In addition, compound 8 has no uterotropic actions even at five times the dose of 17β-estradiol (FIGS. 6A and 6B), confirming in vivo that 8 has no 4-OH tamoxifen-like estrogenic activity mediated by the nuclear estrogen receptors. However, in the whole cell electrophysiological assay, 10 nM 8 was as efficacious as 100 nM 17β-estradiol in attenuating the $GABA_B$ response (FIG. 6).

TABLE 1

Relative binding affinities (RBA) of ligands to full length (ER)α or (ER)β*

| Ligand | Relative binding affinity (ER)α | Relative binding affinity (ER)β |
|---|---|---|
| 17β-estradiol | 100 | 100 |
| 4-hydroxytamoxifen | 36 | 43 |
| GW-5638 | 5 | 8 |
| Compound 8 (example 4) | $4.3 \times 10^{-6}$ | $9.0 \times 10^{-6}$ |

*Relative binding affinities are expressed as a percentage of the potency of 17β-estradiol. Under the conditions described in Example 22, 17β-estradiol was found to have an $IC_{50}$ of 5 nM for (ER)α and 3 nM for (ER)β.

The Rapid Effect of 17β-Estradiol on the $GABA_B$ Response Involves Protein Kinase A (PKA):

The involvement of specific signaling proteins in the 17β-estradiol mediated modulation of $GABA_B$ was determined by blocking different pathways. For example, if activation of the PKA pathway is involved, then the effect of 17β-estradiol on $GABA_B$ responses should be blocked by inhibiting PKA and mimicked by stimulating PKA. Thus, selective PKA inhibitors and activators were used to demonstrate that the PKA is involved. For example, as shown in FIG. 8 graph A and FIG. 9, forskolin (10 μM) could mimic the actions of 17β-estradiol to attenuate the $GABA_B$ response. On the other hand, the specific PKA inhibitor H89 (10 μM) blocked the 17β-estradiol induced suppression of the $GABA_B$ response (FIG. 8 graph B and FIG. 9).

The involvement of PKA in 17β-estradiol modulation of $GABA_B$ responses was further confirmed by the effect of the specific PKA inhibitory peptide PKI (protein kinase A Inhibitor 6–22 Amide, 20 μM) or the non-hydrolyzable cAMP analog Rp-cAMP (200 μM) that blocks PKA activation on neurons. After ~15 min of dialysis with PKI or Rp-cAMP, the 17β-estradiol-induced reduction of the $GABA_B$ response was abolished (FIG. 8 graph C and FIG. 9). Cholera toxin (CTX), which is a bacterial exotoxin secreted by vibrio cholerae, elevates intracellular cAMP levels in a variety of tissues by ADP-ribosylating the G-protein Gs thereby stimulating adenylyl cyclase activity in an apparently irreversible manner. Intracellular dialysis with the active unit of CTX into individual cells occluded the rapid inhibition of $GABA_B$ response by estrogen (FIG. 8 graph D and FIG. 9). These results indicate that the suppression of the $GABA_B$ response by 17β-estradiol requires the activation of PKA. FIG. 9 summarizes the effects of the PKA drugs tested. The PKA activator forskolin could mimic the effects of 17β-estradiol, the specific PKA inhibitors, H89 (10 μM), Rp-cAMPS and PKAI could block the effects. CTX-A could occlude the attenuation of the baclofen response by 17β-estradiol, but the denatured CTX-A could not. Bars represent the mean±S.E.M. of 4–11 cells tested per group (*** p<0.005, * and # p<0.05, versus vehicle-control; CTX-A+17β-estradiol versus denatured CTX-A+17β-estradiol, p<0.05).

Attenuation of the $GABA_B$ Response Involves Protein Kinase C☐(PKCδ)☐

PKC also is involved in 17β-estradiol modulation of $GABA_B$ response, as demonstrated by the effects of several selective PKC inhibitors. The first inhibitor, bisindolymaleimide (BIS), is a selective inhibitor of PKC that does not distinguish between the conventional, novel and atypical isoforms of PKC. The second, Gö6976, is a selective inhibitor of the conventional PKC isoforms (Martiny-Baron et al., 1993; Way et al., 2000). Treatment of neurons with BIS nearly eliminated the effects of 17β-estradiol (FIG. 10 graph A and FIG. 11). In contrast, Gö6976 treatment was without effect (FIG. 11). Indeed, after replacing intracellular EGTA with 10 mM 1,2-bis-(o-aminophenoxyethane)-N,N,N',N'-tetraacetic acid (BAPTA), a calcium buffer with similar $Ca^{2+}$ affinity as EGTA but a much faster on rate, the estrogen inhibition of the $GABA_B$ response was still observed (FIG. 10 graph B and FIG. 11). Because conventional isoforms of PKC are unlikely to be active with this level of calcium buffering, these results further support a role for a $Ca^{2+}$-independent, novel PKC isoform in mediating the effects of estrogen. Finally, the selective PKCδ inhibitor rottlerin (5 μM) completely blocked 17β-estradiol's ability to inhibit the $GABA_B$ response in hypothalamic neurons (FIG. 10, graph C and FIG. 11). FIG. 11 summarizes the effects of the PKC inhibitors tested. Bars represent the mean±S.E.M. of 4–11 cells tested per group (* p<0.005, p<0.01, * p<0.05 versus vehicle-control).

Inhibition of the $GABA_B$ Response by 17β-Estradiol Involves $G\alpha_q$:

Additional results demonstrate that the inhibition of the baclofen induced $GABA_B$ response by 17β-estradiol involves the messenger protein $G\alpha_q$. Although the specific PKC inhibitor BIS blocked the 17β-estradiol effect, forskolin (10 μM) was found to mimic the effects of estrogen in the presence of BIS blockade (FIG. 10 graph D and FIG. 11). Thus, the action of PKC is upstream of the activation of PKA. Indeed, the estrogen receptor-mediated inhibition of the $GABA_B$ response depended on the activation of $G\alpha_q$, as indicated by treating arcuate neurons with a peptide (11 amino acids) that mimics the C-terminal binding site of $G\alpha_q$ (Akhter et al., 1998). This peptide blocks the interaction between G protein coupled receptors and $G\alpha_q$ proteins. In cells dialyzed with this peptide (200 μM), the 17β-estradiol-mediated reduction of the $GABA_B$ response was significantly blocked (FIG. 12 graph A and FIG. 13) when compared to cells dialyzed with a control peptide (11 amino acids) that mimics the C-terminal domain of $G\alpha_s$ (FIG. 12 graph B and FIG. 13). Therefore, $G\alpha_q$ plays a primary role in 17β-estradiol-mediated rapid inhibition.

Moreover, the activation of phospholipase C (PLC), a well known $G\alpha_q$ effector, also plays a role. Indeed, the activation of PLCβ is required for the estrogen-induced inhibition of $GABA_B$ response as indicated by the treatment of neurons with the broad spectrum PLC inhibitor U73122 (10 μM). When U73122 (10 μM) was perfused in the extracellular-bathing media, the estrogen-mediated reduction of $GABA_B$ response was blocked (FIG. 12 graph C and FIG. 13), however the less active PLC inhibitor U73343 at the same concentration had no effect (FIG. 12 graph D and FIG. 13). With reference to FIG. 13, Bars represent the mean±S.E.M. of 4–11 cells tested per group (* p<0.005,  p<0.01 versus vehicle-control; U73122+17β-estradiol versus U73343+17β-estradiol, p<0.05; Gq peptide+17β-estradiol versus Gs peptide+17β-estradiol, p<0.05).

The Attenuation of the $GABA_B$ Response does not Involve Mitogen Activated Protein (MAP) Kinase:

Inhibition of MAP kinase activity does not prevent estrogen modulation of the baclofen response. Recent studies have shown that 17β-estradiol rapidly activates the MAP kinase pathway in primary neuronal cortical cultures and in organotypic cerebrocortical explant cultures (Watters et al., 1997; Singh et al., 1999; Singh et al., 2000). However, treatment with MAP kinases inhibitors PD98059 (10 μM, in the pipette) or U0126 (5 μM), did not affect 17β-estradiol inhibition of baclofen responses (R2/R1 for 17β-estradiol: 58.6±3.4%, n=10; versus PD98059+17β-estradiol: 66.1±11.8%, n=5).

Expression of $GABA_B$ Receptor, PKCδ and Adenylate Cyclase VII Transcripts in Arcuate (GABA, Dopamine and POMC) Neurons:

The expression of $GABA_B$ receptor, PKCδ and adenylate cyclase VII transcripts in arcuate neurons was determined using single-cell RT-PCR from seventy-five acutely dispersed arcuate neurons. The results demonstrated that 90% of the neurons expressed $GAD_{65}$ transcripts including TH-expressing and POMC-expressing neurons (data not shown). Most importantly, 92% of the neurons expressed $GABA_B$ R2 transcripts, which correlates with the 90% response rate to baclofen. Furthermore, single cell RT-PCR results demonstrate that dopamine and POMC neurons express PKCδ and adenylyl cyclase VII transcripts. In one group of cells (n=22), PKCδ and adenylyl cyclase VII transcripts were expressed in the majority (70%) of TH neurons (FIG. 14A), including those that co-express $GAD_{65}$. TH and GAD were co-localized in 60% of this population of neurons. Due to limited amount of cDNA from individual neurons, POMC expression was determined in another group of cells (n=29), demonstrating that PKCδ and adenylyl cyclase VII transcripts were expressed in the majority (75%) of POMC neurons, including those that co-express $GAD_{65}$ (FIG. 14B). POMC and GAD were co-localized in 28% of this population of neurons. Therefore, the single cell RT-PCR data confirm the electrophysiological findings that dopamine and POMC neurons express the critical transcripts for rapid estrogen signaling. GAPDH transcripts were analyzed in the same cells as an internal control for the reverse transcriptase (RT) reaction. One cell contained no RT as a negative control (−RT). Basal hypothalamic tissue RNA was also reverse transcribed in the presence of RT (tissue controls, +). A tissue control without RT (−) was included in each trial. In addition, the following controls were included: Hank's balanced salt solution (HBSS) from the dispersed cellular milieu and a water blank, both of which were negative following RT-PCR (data not shown).

A Unique Membrane Estrogen Receptor Mediates the Rapid Effects of 17β-Estradiol:

The foregoing results demonstrate that a membrane estrogen receptor has been identified. For example, estrogen suppresses the action of the $GABA_B$ receptor agonist baclofen to activate GIRK channels in GABA, POMC, and dopamine neurons. This 17β-estradiol effect is rapid, with measurable suppression occurring within minutes after addition of 17β-estradiol. The kinetics of this response indicates mediation of the response by a membrane 17β-estradiol receptor instead of one of the classical nuclear estrogen receptors (ER)α or (ER)β, which operate by transcription regulation.

The pharmacology observed for this rapid estrogen response further supports the involvement of a novel transmembrane estrogen receptor. The membrane impermeable 17β-estradiol-BSA conjugate gives an identical response to free 17β-estradiol, as would be expected for a membrane associated receptor wherein the hormone-binding site of the receptor is accessible from the extracellular surface of the plasma membrane. The 17β-estradiol response is stereospecific with respect to the configuration of the D-ring hydroxyl group; 17β-estradiol elicits the rapid response whereas 17α-estradiol is inactive. This is notable because 17α-estradiol functions as an agonist of the nuclear estrogen receptors, albeit with slightly reduced potency compared to 17β-estradiol (Barkhem et al., 1998). The SERMs 4-OH tamoxifen, raloxifene, and GW-5638 all behave like 17β-estradiol in mediating this response whereas the steroidal antiestrogen ICI-182,780 antagonizes the 17β-estradiol response. Most importantly, the novel SERM 8 that is devoid of estrogen (or antiestrogen) activity with the nuclear estrogen receptors is a stronger activator of this rapid 17β-estradiol response than 17β-estradiol even at a 10-fold lower concentration. Moreover, this membrane ER has a subnanomolar affinity for estrogen as indicated by pharmacological (Schild) analysis (Lagrange et al., 1997). These results demonstrate that the pharmacology of this rapid response is different, and in the case of 8, separable from that of the nuclear estrogen receptors (Razandi et al., 1999; Levin, 2001; Chambliss and Shaul, 2002).

Recently, Toran-Allerand and colleagues (Toran-Allerand et al., 2002) have identified a high affinity, saturable estrogen receptor, "ERX," that is associated with caveoloar-like microdomains in developing neocortical neurons. This membrane-associated receptor is coupled to the activation of mitogen-activated protein kinases (MAPKs), extracellular-signal related kinase (ERK)1 and ERK2, which appear to be important for the development and survival of neurons (Watters et al., 1997; Singh et al., 1999; Singh et al., 2000; Fitzpatrick et al., 2002). ERX also has a distinct pharmacology in that 17α-estradiol is equipotent as 17β-estradiol in activating the MAP kinase pathway (Toran-Allerand et al., 2002; Wade et al., 2001). However, as demonstrated herein no effects were observed for 17α-estradiol on the $GABA_B$ response, or the μ-opioid response, which is coupled to the same family of GIRK channels in hypothalamic neurons (Lagrange et al., 1997). Similarly, Gu and Moss (Gu and Moss, 1996) found that 17α-estradiol did not mimic the actions of 17β-estradiol in the hippocampus to potentiate the glutamate (kainate)-mediated currents in CA1 pyramidal neurons. Likewise, Mermelstein et al. (1996) found that 17α-estradiol was much less efficacious than 17β-estradiol in reducing L-type calcium currents in neostriatal neurons. Therefore, the membrane estrogen receptor that modulates channel activity in neurons via the PKC-PKA pathway is pharmacologically distinct from the receptor that is coupled to activation of ERK½ that promotes growth and survival.

17β-Estradiol Activates PKCδ and PKA to Alter the Coupling of GPCRs to $K^+$ Channels in Hypothalamic Neurons:

The data detailed herein demonstrate that the signal transduction pathway for the rapid response to estrogen in hypothalamic neurons follows that depicted in FIG. 15. With reference to FIG. 15, the sequence of events are: (1) 17β-estradiol binds to a novel transmembrane estrogen receptor; (2) ligand binding activates $G\alpha_q$; (3) activated $G\alpha_q$ in turn activates PLC; (4) activated PLC liberates DAG; (5) free DAG stimulates PKCδ; (6) PKCδ activates adenylyl cyclase (VII); (7) cAMP levels are elevated; (8) cAMP stimulates PKA; (9) PKA phosphorylates membrane targets critical for $K^+$ channel function.

Further support for the pathway shown in FIG. 15 is found in that protein kinase pathways affect $GABA_B$ receptor-mediated signaling in CNS neurons. Activation of protein kinase C suppresses the $GABA_B$ receptor-activation of GIRK channels in the hippocampal CA1 pyramidal neurons (Dutar and Nicoll, 1988) and attenuates the $GABA_B$ receptor-mediated inhibition of norepinephrine release from cerebellar slices (Taniyama et al., 1992).

Currently, there are 12 known members of the PKC family (Way et al., 2000). The family is divided into three groups based on sequence homology and biochemical regulation. Class A, or conventional PKCs (PKCα, βI, β II and γ) are the well-known, $Ca^{2+}$-dependent PKCs. Class B, or novel PKCs (PKCδ, ε, θ and η), are $Ca^{2+}$ independent. Finally, Class C PKCs, or atypical PKCs (PKCζ and τ/λ), are the most divergent class. Atypical PKCs are also $Ca^{2+}$ independent and do not require diacylglycerol for activation (Way et al., 2000). The rapid, $GABA_B$ suppressing effects of estrogen in hypothalamic neurons were sensitive to the broad spectrum PKC inhibitor BIS, but not to Gö6976, implicating the involvement of a PKC not belonging to the conventional PKC class. In addition, estrogen's inhibition of the $GABA_B$ response was not altered by inclusion of 10 mM BAPTA in the intracellular recording patch pipette, providing confirming that the $Ca^{2+}$-dependent, conventional PKCs are not involved. However, the selective PKCδ inhibitor rottlerin blocked the actions of 17β-estradiol suggesting that this novel class PKC is a mediator of the rapid 17β-estradiol response. Moreover, the scRT-PCR data on the expression of PKCδ transcripts in arcuate neurons described herein further implicate PKCδ in the 17β-estradiol-mediated inhibition of the $GABA_B$ response. Likewise, PKCδ is involved in the estrogen-mediated inhibition of $K^+$ channels and fluid retention in female distal colonic epithelial cells, although the upstream signaling pathway is not known (Doolan et al., 2000).

PKC Activation is Upstream of PKA Activation:

PKC activation in the 17β-estradiol mediated inhibition of the $GABA_B$ is upstream of PKA activation. For example, internal perfusion of BIS completely blocked the inhibition of the baclofen response by 17β-estradiol, but did not attenuate the inhibition of the baclofen response by forskolin applied via bath perfusion. PKC is known to activate adenylyl cyclases (Jacobowitz et al., 1993; Yoshimura and Cooper, 1993; Lin and Chen, 1998); moreover, when adenylyl cyclase (AC) is activated by PKC, instead of by $G\alpha_s$ or forskolin, it is resistant to inhibition by $G\alpha_i$ (Pieroni et al., 1993). To date, nine AC isozymes have been cloned (AC types I–IX). Notably, AC VII has a potential binding site for PKCδ that is not present in the sequences of the other adenylyl cyclases, which would allow PKCδ to directly phosphorylate AC VII (Nelson et al., 2003). GABA neurons in the cortex, hippocampus, striatum and cerebellum are immunoreactive for AC VII (Mons et al., 1998), and, as disclosed herein, hypothalamic GABA, TH and POMC neurons express AC VII transcripts.

$G\alpha_q$ Mediates the Inhibition of the $GABA_B$ Response by 17β-Estradiol Through PLC:

The results described herein show that a membrane ER is specifically coupled to the messenger $G\alpha_q$, and that this messenger protein is involved in the inhibition of the $GABA_B$ response by 17β-estradiol. This conclusion is confirmed by results observed when intracellular dialysis with a peptide fragment of $G\alpha_q$ blocked the receptor interaction with G protein. This $G\alpha_q$ peptide has been used to block $G\alpha_q$ signaling pathways in cortical pyramidal neurons (Carr et al., 2002). In addition, the estrogen-mediated reduction of the $GABA_B$ response was significantly reduced by the phospholipase C inhibitor U73122 compared to cells perfused with the less active inhibitor U73343. Thus, the messenger $G\alpha_q$ is involved in the inhibition of the $GABA_B$ response by 17β-estradiol.

Most PKCs are activated by diacylglycerol and some require the presence of $Ca^{2+}$. Thus, PKCs are downstream of the phospholipase C (PLC)-inositol triphosphate/diacylglycerol signaling cascade. Because different forms of PLC can be activated by various messengers including $G\alpha_q$, $G\beta\gamma$ (PLCβ), and tyrosine kinases (PLCγ), the PKC family is involved in a diverse array of signaling cascades (Tanaka and Nishizuka, 1994; Battaini, 2001).

Example 23

This example describes the identification of estrogen receptor antagonists and the determination of antagonist potency using Schild analysis. The general protocol for this analysis is disclosed by Lagrange et al., 1997. Cumulative concentration-response curves are generated by applying increasing concentrations of the selective estrogen receptor agonist, compound 8, in the whole cell electrophysiological assay described above. Increasing concentrations of baclofen are applied until the drug-induced outward current reaches a new steady level. The $EC_{50}$ values for both baclofen and compound 8 are calculated using SigmaPlot (Jandel Scientific, Costa Madre, Calif.) software to determine the best fit to the logistic equation. Cells are then superfused with 1 nM solution of the potential estrogen receptor antagonist. Increasing concentrations of compound 8 (as applied in generating the initial concentration-response curve above) are then applied to generate a second response curve. The cells are then treated with a 2 nm solution of the potential antagonist and the concentration response curve repeated. This process is repeated with increasing concentrations of the potential antagonist to generate multiple concentration response curves. Linear regression fit of the data {log(Dose Ratio−1) versus−log [antagonist concentration]} yields a slope of −1.0 when compound 8 and the proposed antagonist bind to the previously unidentified membrane associated estrogen receptor disclosed herein.

Example 24

This example describes the evaluation of the cardioprotective activity of the disclosed compounds and provides a method for identifying novel cardioprotective selective estrogen receptor modulators. Apolipoprotein E-deficient C57/B1J (apo E KO) mice (available from Taconic Farms), 4–7 weeks of age, are ovariectomized. The animals are randomized by weight into groups (n=12–15 mice per group). The mice are treated with the disclosed compound or 17β-estradiol sulfate (at 1 mg/kg/day) in the diet using a protocol wherein the amount of consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The mice are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

Total cholesterol and triglycerides are determined using enzymatic methods with commercially available kits from Boehringer Mannheim and Wako Biochemicals, respectively. Separation and quantification of plasma lipoproteins are performed, and each lipoprotein fraction is quantified by multiplying the total cholesterol value by the relative percent area of each respective chromatogram peak.

Aortic atherosclerosis is quantified by carefully isolating the aortas and placing the vessels in formalin fixative for 48–72 h before handling. Atherosclerotic lesions are identified using Oil Red O staining. The vessels are briefly destained, and then imaged. The lesions are quantified en face along the aortic arch and lesion assessment is performed on the vessels, specifically on the region contained within the aortic arch from the proximal edge of the brachiocephalic trunk to the distal edge of the left subclavian artery. Aortic atherosclerosis data can be expressed as percent lesion involvement strictly within this defined luminal area.

Example 25

This example describes the evaluation of prophylactic neuroprotection using the disclosed compounds in response to oxygen deprivation/reperfusion, and provides a method for identifying novel neuroprotective selective estrogen receptor modulators. Female Mongolian gerbils (available from, for example, Charles River Laboratories, Kingston, N.Y.) after acclimation, are anesthetized with isoflurane and ovariectomized (day 0). Beginning the following morning (day 1), gerbils are treated subcutaneously with either vehicle (10% EtOH/corn oil), 17β-estradiol (1 mg/kg, sc) or a compound disclosed herein. Prior to day 6, the gerbils are fasted overnight (to facilitate consistent ischemic injury) and then subjected to global ischemia surgery. The surgery proceeds by anesthetizing the gerbils with isoflurane, visualizing the common carotid arteries via a mid-line neck incision and simultaneously occluding both arteries for 5 minutes with micro-aneurysm clips. Following occlusion, the clips are removed to allow cerebral reperfusion and the neck incision is closed with wound clips. On day 12, gerbils are exposed to a lethal dose of $CO_2$, the brains frozen on dry ice and stored at −80° C.

The degree of neuronal protection is evaluated by in situ hybridization analysis of neurogranin mRNA. Briefly, 20 μM coronal cryostat sections are collected on gelatin-coated slides, dried and stored at −80° C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 μL ($6 \times 10^6$ DPM/slide) of an antisense or sense (control) riboprobe for Neurogranin ($^{35}$S-UTP-labeled NG-241; bases 99–340) in a 50% formamide hybridization mix and incubated overnight at 55° C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 μg/ml) and washed (2×30 min) at 67° C. in 0.1×SSC to remove nonspecific label. After dehydration, the slides are opposed to BioMax (BMR-1; Kodak) X-ray film overnight.

The level of neurogranin hybridization signal is used to quantitatively assess the degree of neuronal loss in the CA1 region after injury and to evaluate the efficacy of 17β-estradiol and the disclosed compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 μm apart) per animal are averaged and statistically evaluated. Numerical values are reported as the mean±S.E.M. One-way analysis of variance is used to test for differences in the level of neurogranin mRNA and all statements of non-difference in the results section imply that $p>0.05$.

Example 26

This example describes the evaluation of cognition enhancement achieved using the disclosed compounds. Ovariectomized rats (n=50) are habituated to an 8-arm radial arm maze for 10-min periods on each of 5 consecutive days. Animals are water-deprived prior to habituation and testing. A 100 μL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups: (1) Negative controls: injected with 10% DMSO/sesame oil vehicle once daily for 6 days (1 μg/kg, subcutaneous). (2) Positive controls: injected with 17β-estradiol benzoate for 2 days and tested 4 days after the second injection (17β-estradiol benzoate at 10 μg/0.1 mL per rat). (3) 17β-estradiol will be injected daily for 6 days (20 μg/kg, subcutaneous). (4) Test compound: injected daily for 6 days (doses may vary). All injections will begin after testing on the last day of acquisition. The last injection for groups 1, 3, and 4 will take place 2 h before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

VII. REFERENCES

The following references can be referred to in the specification and each one is specifically herein incorporated by reference.

Akema T, Chiba A, Kimura F (1990) On the relationship between noradenergic stimulatory and GABAergic inhibitory systems in the control of luteinizing hormone secretion in female rats. Neuroendo 52: 566–572.

Akhter S A, Luttrell L M, Rockman H A, Iaccarino G, Lefkowitz R J, Koch W J (1998) Targeting the receptor-Gq interface to inhibit in vivo pressure overload myocardial hypertrophy. Science 280: 574–577.

Barkhem T, Carlsson B, Nilsson Y, Enmark E, Gustafsson J Å, Nilsson S (1998) Differential response of estrogen receptor α and estrogen receptor β to partial estrogen agonists/antagonists. Mol Pharm 54: 105–112.

Battaini F (2001) Protein kinase C isoforms as therapeutic targets in nervous system disease states. Pharmacol Res 44: 353–361.

Björklund A, Lindvall O (1984) Dopamine-containing systems in the CNS. In: Handbook of Chemical Neuroanatomy: Classical Transmitters in the CNS, Part 1 (Björklund A, Hökfelt T, eds), pp 55–122. Amsterdam: Elsevier.

Carr D B, Cooper D C, Ulrich S L, Spruston N, Surmeier D J (2002) Serotonin receptor activation inhibits sodium current and dendritic excitability in prefrontal cortex via a protein kinase C-Dependent mechanism. J Neurosci 22: 6846–6855.

Chambliss K L, Shaul P W (2002) Estrogen modulation of endothelial nitric oxide synthase. Endocr Rev 23: 665–686.

Dave J R, Rubinstein N, Eskay R L (1985) Evidence that β-endorphin binds to specific receptors in rat peripheral tissues and stimulates the adenylate cyclase-adenosine 3',5'-monophosphate system. Endocrinology 117: 1389–1396.

Demotes-Mainard J, Arnauld E, Vincent J D (1990) Estrogens modulate the responsiveness of in vivo recorded striatal neurons to iontophoretic application of dopamine in rats: Role of $D_1$ and $D_2$ receptor activation. J Neuroendocrinol 2: 825–832.

Doolan C M, Condliffe S B, Harvey B J (2000) Rapid non-genomic activation of cytosolic cyclic AMP-dependent protein kinase activity and $[Ca^{2+}]_i$ by 17β-oestradiol in female rat distal colon. Br J Pharmacol 129: 1375–1386.

Dutar P, Nicoll R A (1988) Pre- and postsynaptic GABA(B) receptors in the hippocampus have different pharmacological properties. Neuron 1: 585–591.

Ferin M, Van Vugt D, Wardlaw S (1984) The hypothalamic control of the menstrual cycle and the role of endogenous opioid peptides. Recent Prog Horm Res 40: 441–485.

Fitzpatrick J L, Mize A L, Wade C B, Harris J A, Shapiro R A, Dorsa D M (2002) Estrogen-mediated neuroprotection against β-amyloid toxicity requires expression of estrogen receptor α or β and activation of the MAPK pathway. J Neurochem 82: 674–682.

Gu Q, Moss R L (1996) 17β-estradiol potentiates kainate-induced currents via activation of the cAMP cascade. J Neurosci 16: 3620–3629.

Gu Q, Moss R L (1998) Novel mechanism for non-genomic action of 17β-estradiol on kainate-induced currents in isolated rat CA1 hippocampal neurones. J Physiol (Lond) 506: 745–754.

Harrison N L, Majewska M D, Harrrington J W, Barker J L (1987) Structure-activity relationships for steroid interaction with the gamma-aminobutyric acid$_A$ receptor complex. J Pharm Exp Ther 241: 346–353.

Herbison A E (1997) Estrogen regulation of GABA transmission in rat preoptic area. Brain Res Bull 44: 321–326.

Herbison A E, Horvath T L, Naftolin F, Leranth C (1995) Distribution of estrogen receptor-immunoreactive cells in monkey hypothalamus: Relationship to neurones containing luteinizing hormone-releasing hormone and tyrosine hydroxylase. Neuroendo 61: 1–10.

Herbison A E, Skynner M J, Sim J A (2001) Lack of detection of estrogen receptor-α transcripts in mouse gonadotropin-releasing hormone neurons. Endocrinology 142: 493.

Hökfelt T, Mårtensson R, Björklund A, Kleinau S, Goldstein M (1984) Distributional maps of tyrosine-hydroxylase-immunoreactive neurons in the rat brain. In: Handbook of Chemical Neuroanatomy (Björklund A, Hökfelt T, eds), pp 277–379. B. V.: Elsevier.

Jacobowitz O, Chen J, Premont R T, Iyengar R (1993) Stimulation of specific types of Gs-stimulated adenylyl cyclases by phorbol ester treatment. J Biol Chem 268: 3829–3832.

Jarry H, Leonhardt S, Wuttke W (1995) The inhibitory effect of β-endorphin on LH release in ovariectomized rats does not involve the preoptic GABAergic system. Exp Clin Endocrinol Diabetes 103: 317–323.

Katzenellenbogen J A, Carlson K E, Katzenellenbogen B S (1985) Facile geometric isomerization of phenolic non-steroidal estrogens and antiestrogens: Limitations to the interpretation of experiments characterizing the activity of individual isomers. J Steroid Biochem 22: 589–596.

Kelly M J, Lagrange A H, Wagner E J, Rønnekleiv O K (1999) Rapid effects of estrogen to modulate G protein-coupled receptors via activation of protein kinase A and protein kinase C pathways. Steroids 64: 64–75.

Kelly M J, Loose M D, Rønnekleiv O K (1990) Opioids hyperpolarize β-endorphin neurons via mu-receptor activation of a potassium conductance. Neuroendo 52: 268–275.

Kelly M J, Loose M D, Rønnekleiv O K (1992) Estrogen suppresses mu-opioid and $GABA_B$-mediated hyperpolarization of hypothalamic arcuate neurons. J Neurosci 12: 2745–2750.

Kelly M J, Rønnekleiv O K (1994) Electrophysiological analysis of neuroendocrine neuronal activity in hypothalamic slices. In: Methods in Neurosciences: Pulsatility in Neuroendocrine Systems (Levine J E, ed), pp 47–67. San Diego: Academic Press, Inc.

Kelly M J, Rønnekleiv O K, Eskay R L (1984) Identification of estrogen-responsive LHRH neurons in the guinea pig hypothalamus. Brain Res Bull 12: 399–407.

Kelly M J, Wagner E J (1999) Estrogen modulation of G-protein-coupled receptors. Trends Endocrinol Metab 10: 369–374.

Lagrange A H, Rønnekleiv O K, Kelly M J (1994) The potency of mu-opioid hyperpolarization of hypothalamic arcuate neurons is rapidly attenuated by 17β-estradiol. J Neurosci 14: 6196–6204.

Lagrange A H, Rønnekleiv O K, Kelly M J (1995) Estradiol-17β and mu-opioid peptides rapidly hyperpolarize GnRH neurons: A cellular mechanism of negative feedback? Endocrinology 136: 2341–2344.

Lagrange A H, Rønnekleiv O K, Kelly M J (1997) Modulation of G protein-coupled receptors by an estrogen receptor that activates protein kinase A. Mol Pharmacol 51: 605–612.

Lagrange A H, Wagner E J, Rønnekleiv O K, Kelly M J (1996) Estrogen rapidly attenuates a $GABA_B$ response in hypothalamic neurons. Neuroendo 64: 114–123.

Lambert J J, Belelli D, Hill-Venning C, Peters J A (1995) Neurosteroids and $GABA_A$ receptor function. Trends Pharmacol Sci 16: 295–303.

Leranth C, MacLusky N J, Brown T J, Chen E C, Redmond D E, Jr., Naftolin F (1992) Transmitter content and afferent connections of estrogen-sensitive progestin receptor-containing neurons in the primate hypothalamus. Neuroendo 55: 667–682.

Levin E R (2001) Invited Review: Cell localization, physiology, and nongenomic actions of estrogen receptors. J Appl Physiol 91: 1860–1867.

Lin W-W, Chen. B C (1998) Distinct PKC isoforms mediate the activation of cPLA2 and adenylyl cyclase by phorbol ester in RAW264.7 macrophages. Br J Pharmacol 125: 1601–1609.

Loose M D, Rønnekleiv O K, Kelly M J (1990) Membrane properties and response to opioids of identified dopamine neurons in the guinea pig hypothalamus. J Neurosci 10: 3627–3634.

Loose M D, Rønnekleiv O K, Kelly M J (1991) Neurons in the rat arcuate nucleus are hyperpolarized by $GABA_B$ and mu-opioid receptor agonists: Evidence for convergence at a ligand-gated potassium conductance. Neuroendo 54: 537–544.

Martiny-Baron G, Kazanietz M G, Mischak H, Blumberg P M, Kochs G, Hug H, Marme D, Schachtele C (1993) Selective inhibition of protein kinase C isozymes by the indolocarbazole Gö6976. J Biol Chem 268: 9194–9197.

McEwen B S (2001) Estrogens effects on the brain: Multiple sites and molecular mechanisms. J Appl Physiol 91: 2785–2801.

Mermelstein P G, Becker J B, Surmeier D J (1996) Estradiol reduces calcium currents in rat neostriatal neurons via a membrane receptor. J Neurosci 16: 595–604.

Mitsushima D, Marzban F, Luchansky L L, Burich A J, Keen K L, Durning M, Golos T G, Terasawa E (1996) Role of glutamic acid decarboxylase in the prepubertal inhibition of the luteinizing hormone releasing hormone release in female rhesus monkeys. J Neurosci 16: 2563–2573.

Mons N, Yoshimura M, Ikeda H, Hoffman P L, Tabakoff B (1998) Immunological assessment of the distribution of type VII adenylyl cyclase in brain. Brain Res 788: 251–261.

Morrell J I, McGinty J F, Pfaff D W (1985) A subset of □-endorphin or dynorphin-containing neurons in the medial basal hypothalamus accumulates estradiol. Neuroendo 41: 417–426.

Neill J D (1980) Neuroendocrine regulation of prolactin secretion. Front Neuroendo 6: 129–155.

Nelson E J, Hellevuo K, Yoshimura M, Tabakoff B (2003) Ethanol-induced phosphorylation and potentiation of the activity of type 7 adenylyl cyclase: Involvement of PKC delta. J Biol Chem 278: 4552–4560.

Paradiso K, Zhang J, Steinbach J H (2001) The C terminus of the human nicotinic alpha 4 beta 2 receptor forms a binding site required for potentiation by an estrogenic steroid. J Neurosci 21: 6561–6568.

Pieroni J P, Jacobowitz O, Chen J, Iyengar R (1993) Signal recognition and integration by Gs-stimulated adenylyl cyclases. Curr Opin Neurobiol 3: 345–351.

Qiu et al., (2003) J. Neurosci. 23: 9529–9540.

Razandi M, Pedram A, Greene G L, Levin E R (1999) Cell membrane and nuclear estrogen receptors (ERs) originate from a single transcript: Studies of ERα and ERβ expressed in Chinese hamster ovary cells. Mol Endo 13: 307–319.

Rupprecht R, Holsboer F (1999) Neuroactive steroids: mechanisms of action and neuropsychopharmacological perspectives. Trends Neurosci 22: 410–416.

Seltzer A M, Donoso A O (1992) Restraining action of GABA on estradiol-induced LH surge in the rat: GABA activity in brain nuclei and effects of GABA mimetics in the medial preoptic nucleus. Neuroendo 55: 28–34.

Sherwin B B (2003) Estrogen and cognitive functioning in women. Endocr Rev 24: 133–151.

Simonian S X, Spratt D P, Herbison A E (1999) Identification and characterization of estrogen receptor α-containing neurons projecting to the vicinity of the gonadotropin-releasing hormone perikarya in the rostral preoptic area of the rat. J Comp Neurol 411: 346–358.

Singh M, Setalo G J, Guan X, Frail D E, Toran-Allerand C D (2000) Estrogen-induced activation of the mitogen-activated protein kinase cascade in the cerebral cortex of estrogen receptor-alpha knock-out mice. J Neurosci 20: 1694–1700.

Singh M, Setalo Jr G, Guan X, Warren M, Toran-Allerand C D (1999) Estrogen-induced activation of mitogen-activated protein kinase in cerebral cortical explants: Convergence of estrogen and neurotrophin signaling pathways. J Neurosci 19: 1179–1188.

Stearns V, Ullmer L, Lopez J F, Smith Y, Isaacs C, Hayes D (2002) Hot flushes. Lancet 360: 1851–1861.

Sullivan K A, Witkin J W, Ferin M, Silverman A J (1995) Gonadotropin-releasing hormone neurons in the rhesus macaque are not immunoreactive for the estrogen receptor. Brain Res 685: 198–200.

Takano K, Asano S, Yamashita N (1994) Activation of G protein-coupled $K^+$ channels by dopamine in human GH-producing cells. Am J Physiol 266: E318–E325.

Tanaka C, Nishizuka Y (1994) The protein kinase C family for neuronal signaling. Annu Rev Neurosci 17: 551–567.

Taniyama K, Niwa M, Kataoka Y, Yamashita K (1992) Activation of protein kinase C suppresses the gamma-aminobutyric acid B receptor-mediated inhibition of the vesicular release of noradrenaline and acetylcholine. J Neurochem 58: 1239–1245.

Toran-Allerand C D, Guan X, MacLusky N J, Horvath T L, Diano S, Singh M, Connolly E S, Jr., Nethrapalli I S, Tinnikov A A (2002) ER-X: A novel, plasma membrane-associated, putative estrogen receptor that is regulated during development and after ischemic brain injury. J Neurosci 22: 8391–8401.

Valverde M A, Rojas P, Amigo J, Cosmelli D, Orio P, Bahamonde M I, Mann G E, Vergara C, Latorre R (1999) Acute activation of Maxi-K channels (hSlo) by estradiol binding to the β subunit. Science 285: 1929–1931.

Wade C B, Robinson S, Shapiro R A, Dorsa D M (2001) Estrogen receptor (ER)alpha and ERbeta exhibit unique pharmacologic properties when coupled to activation of the mitogen-activated protein kinase pathway. Endocrinology 142: 2336–2342.

Wagner E J, Bosch M A, Kelly M J, Rønnekleiv O K (1999) A powerful $GABA_B$ receptor-mediated inhibition of GABAergic neurons in the arcuate nucleus. NeuroReport 10: 2681–2687.

Wagner E J, Manzanares J, Moore K E, Lookingland K J (1994) Neurochemical evidence that estrogen-induced suppression of kappa-opioid-receptor-mediated regulation of tuberoinfundibular dopaminergic neurons is prolactin-independent. Neuroendo 59: 197–201.

Wagner E J, Reyes-Vazquez C, Rønnekleiv O K, Kelly M J (2000) The role of intrinsic and agonist-activated conductances in determining the firing patterns of preoptic area neurons in the guinea pig. Brain Res 879: 29–41.

Wagner E J, Rønnekleiv O K, Bosch M A, Kelly M J (2001) Estrogen biphasically modifies hypothalamic GABAergic function concomitantly with negative and positive control of luteinizing hormone release. J Neurosci 21: 2085–2093.

Watson R E, Langub M C, Landis J W (1992) Further evidence that most luteinizing hormone-releasing hormone neurons are not directly estrogen-responsive: Simultaneous localization of luteinizing hormone-releasing hormone and estrogen receptor immunoreactivity in the guinea-pig brain. J Neuroendocrinol 4: 311–317.

Watters J J, Campbell J S, Cunningham M J, Krebs E G, Dorsa D M (1997) Rapid membrane effects of steroids in neuroblastoma cells: Effects of estrogen on mitogen activated protein kinase signalling cascade and c-fos immediate early gene transcription. Endocrinology 138: 4030–4033.

Way K J, Chou E, King G L (2000) Identification of PKC-isoform-specific biological actions using pharmacological approaches. Trends Pharmacol Sci 21: 181–187.

Wetzel C H, Hermann B, Behl C, Pestel E, Rammes G, Zieglgansberger W, Holsboer F, Rupprecht R (1998) Functional antagonism of gonadal steroids at the 5-hydroxytryptamine type 3 receptor. Mol Endocrinol 12: 1441–1451.

Yoshimura M, Cooper D M (1993) Type-specific stimulation of adenylyl cyclase by protein kinase C. J Biol Chem 268: 4604–4607.

Zhu Y, Rice C D, Pang Y, Pace M, Thomas P (2003) Cloning, expression, and characterization of a membrane progestin receptor and evidence it is an intermediary in meiotic maturation of fish oocytes. Proc Natl Acad Sci USA 100: 2231–2236.

It will be apparent to those skilled in the art that various modifications and variations can be made in the present compounds, compositions and methods without departing from the scope or spirit of the disclosure. Other embodiments of the compounds, compositions and methods will be apparent to those skilled in the art from consideration of the specification and practice of the procedures disclosed herein. It is intended that the specification and examples be considered as exemplary only, with a true scope and spirit of the invention being indicated by the following claims.

What is claimed:

1. A compound according to the formula:

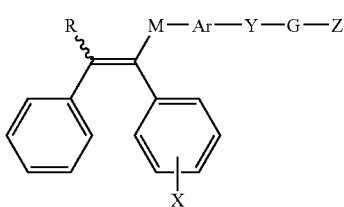

wherein R is H or a lower aliphatic group; M is an amide or sulfonamide group; Ar is an aromatic group; X is a hydrogen, hydroxy, alkoxy, or a halogen; Y is a heteroatom; G is a linker group; and Z is hydroxy or a charged moiety.

2. The compound according to claim 1, wherein the compound has the formula

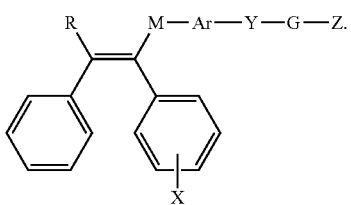

3. The compound according to claim 1, wherein the compound has the formula

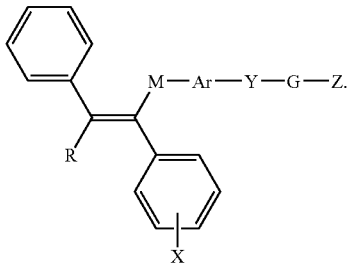

4. The compound according to claim 1, wherein Ar is a phenyl group.

5. The compound according to claim 1, wherein the compound has the formula

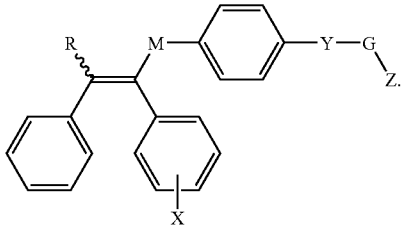

6. The compound according to claim 1, wherein the compound has the formula

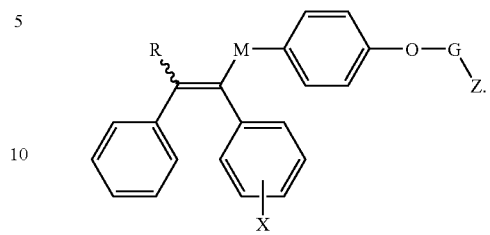

7. The compound according to claim 1, wherein M is an amide group.

8. The compound according to claim 7, wherein the compound has the formula

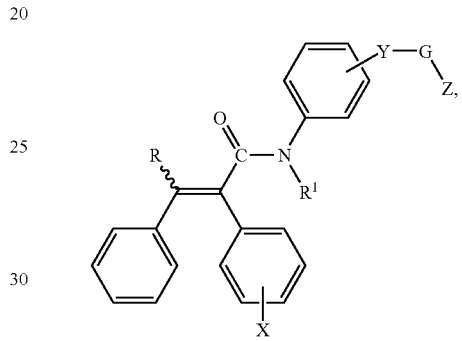

wherein $R^1$ is hydrogen, lower alkyl or an aralkyl group.

9. The compound according to claim 1, wherein G is a lower alkyl group.

10. The compound according to claim 1, wherein Z is a anionic group.

11. The compound according to claim 1, wherein Z is a cationic group.

12. The compound according to claim 1, wherein Z is an amino or a carboxy group.

13. The compound according to claim 1, wherein Y is oxygen and -G-Z has a formula selected from the group consisting of

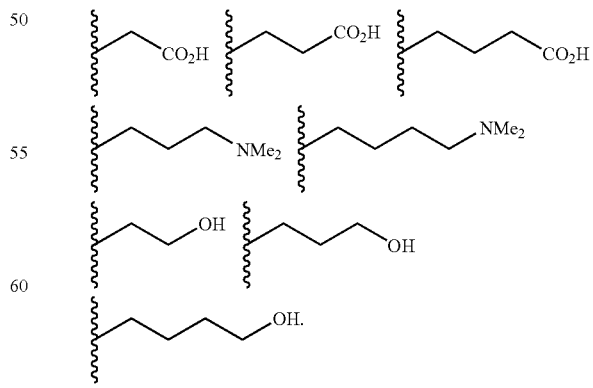

14. The compound according to claim 1, wherein R is hydrogen or lower alkyl.

15. A compound according to the formula:

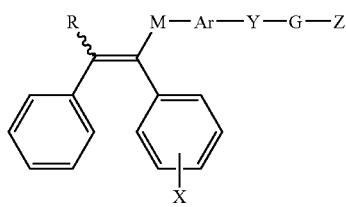

wherein R is H or a lower aliphatic group; M is a ketone, amide or sulfonamide group; AR is an aromatic group; X is a hydroxy group; Y is a heteroatom; G is a linker group; and Z hydroxy or a charged moiety.

16. The compound according to claim 1, wherein X is hydrogen.

17. The compound according to claim 1, wherein the compound has the formula

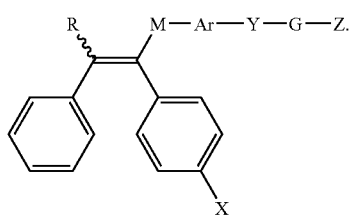

18. The compound according to claim 1, wherein the compound has the formula

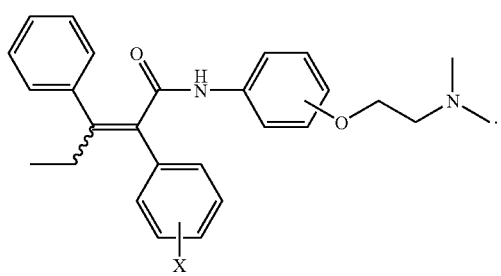

19. The compound according to claim 1, wherein the compound has the formula

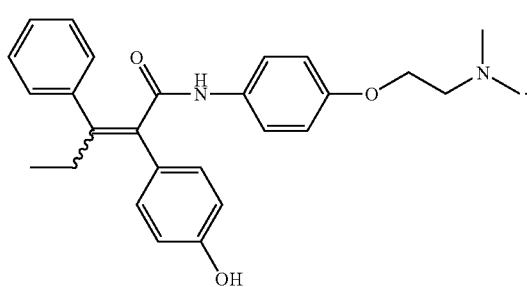

20. The compound according to claim 1, wherein the compound has the formula

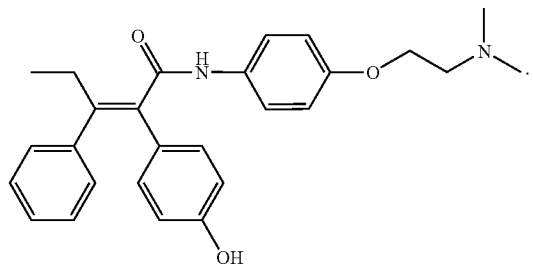

21. A composition, comprising a pharmaceutically effective amount of a compound or a pharmaceutically acceptable salt of the compound according to the formula:

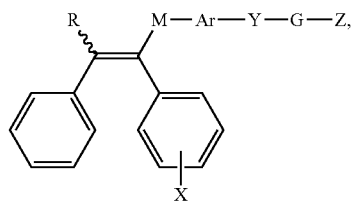

wherein R is H or a lower aliphatic group; M is an amide or sulfonamide group; Ar is an aromatic group; X is a hydrogen, hydroxy, alkoxy, or a halogen; Y is a heteroatom; G is a linker group; and Z is hydroxy or a charged moiety; and a pharmaceutical carrier.

22. The composition according to claim 21, wherein the compound has the formula

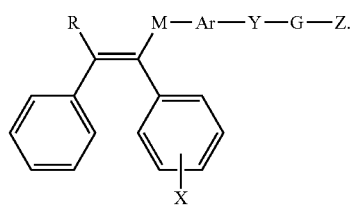

23. The composition according to claim 21, wherein the compound has the formula

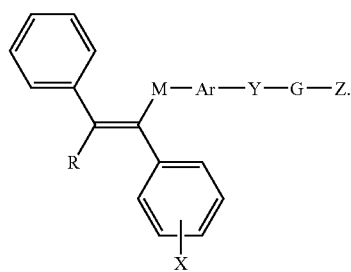

24. The composition according to claim 21, wherein the compound has the formula

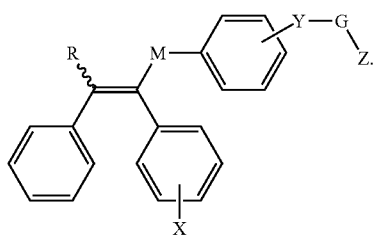

25. The composition according to claim 21, wherein the compound has the formula

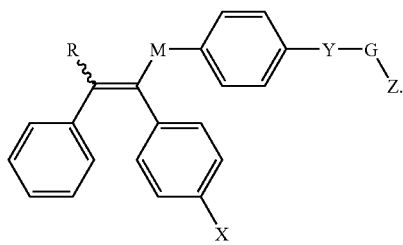

26. A composition, comprising a pharmaceutically effective amount of a compound or a pharmaceutically acceptable salt of the compound according to the formula:

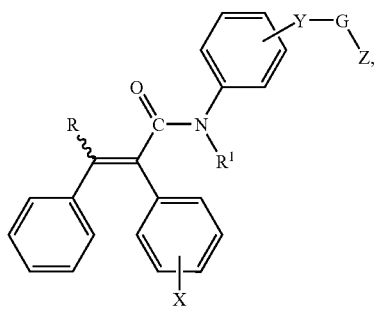

wherein $R^1$ is hydrogen, lower alkyl or an aralkyl group.

wherein R is H or a lower aliphatic group; Ar is an aromatic group; X is a hydrogen, hydroxy, alkoxy, or a halogen; Y is a heteroatom; G is a linker group; and Z is hydroxy or a charged moiety; and a pharmaceutical carrier.

27. The composition according to claim 21, wherein the compound has the formula

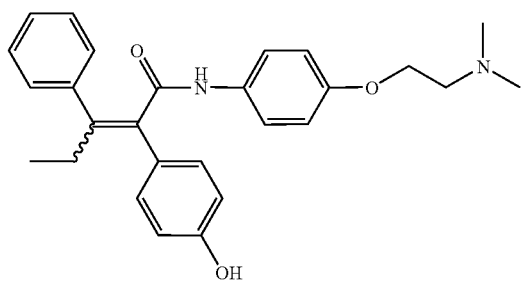

28. The composition according to claim 21, wherein the compound has the formula

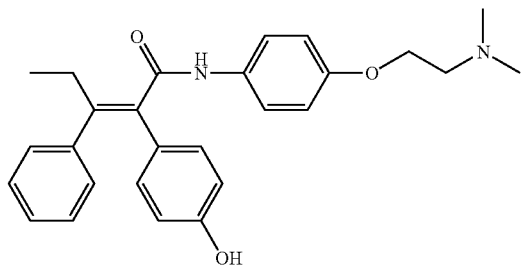

* * * * *